(12) United States Patent
Kotake et al.

(10) Patent No.: US 6,255,285 B1
(45) Date of Patent: Jul. 3, 2001

(54) PHENETHYLAMINE DERIVATIVES

(75) Inventors: Ken-ichiro Kotake; Toshiro Kozono; Tsutomu Sato; Hisanori Takanashi, all of Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/485,620

(22) PCT Filed: Aug. 14, 1998

(86) PCT No.: PCT/JP98/03627

§ 371 Date: Feb. 15, 2000

§ 102(e) Date: Feb. 15, 2000

(87) PCT Pub. No.: WO99/09053

PCT Pub. Date: Feb. 25, 1999

(30) Foreign Application Priority Data

Aug. 15, 1997 (JP) .................................. 9-255879
May 28, 1998 (JP) ................................ 10-186802

(51) Int. Cl.$^7$ .......................... A61K 38/05; A61K 38/06; C07K 5/06; C07K 5/08
(52) U.S. Cl. ................... 514/18; 514/19; 514/20; 514/616; 514/620; 514/626; 530/331; 562/443; 562/444; 562/445; 562/448; 562/450; 564/153; 564/155; 564/158; 564/164; 564/165; 564/196
(58) Field of Search ................... 514/18, 19, 20, 514/616, 620, 626; 530/331, 345; 562/443, 444, 445, 448, 450; 564/153, 155, 158, 164, 165, 196

(56) References Cited

U.S. PATENT DOCUMENTS 6,013,633 * 1/2000 Balasubramanium et al. ........ 514/18

FOREIGN PATENT DOCUMENTS

| 0647656 | 4/1995 | (EP) . |
| 7138284 | 5/1995 | (JP) . |
| 9403483 | 2/1994 | (WO) . |
| 9640208 | 12/1996 | (WO) . |
| 9748713 | 12/1997 | (WO) . |
| 9921846 | 5/1999 | (WO) . |

OTHER PUBLICATIONS

Inouye et al. New Synthetic Substrates for Pepsin. Biochemistry, vol. 5, No. 7, pp. 2473–2483, Jul. 1966.*
Terada et al. Action of Pepsin on Synthetic Substrates. J. Biochem. vol. 70, No. 1, pp. 133–142, 1971.*
Smith et al. Toward Antibody–directed Enzyme Prodrug Therapy . . . J. Biol. Chem. vol. 272, No. 25, pp. 15804–15816, Jun. 20, 1997.*
Takanashi et al., "GM–109: A Novel, Selective Motlilin Receptor Antagonist in the Smooth Muscle of the Rabbit Small Intestine", *The Journal of Pharmacology and Experimental Therapeutics*, vol.273, No.2, pp.624–628, (1995).
Poitras et al., "Motilin Synthetic Analogues and Motilin Receptor Antagonists", *Biochemical and Biophysical Research Communications*, vol.205, No.1, pp.449–454, (1994).
Depoortere et al., "Antagonistic properties of [Phe3, Leu13] porcine motilin", *European Journal of Pharmacology*, vol.286, pp.241–247, (1995).

* cited by examiner

Primary Examiner—Jeffrey E. Russel
(74) Attorney, Agent, or Firm—Browdy and Neimark

(57) ABSTRACT

The present invention has as its object providing phenethylamine derivatives that typically function as a motilin receptor antagonist and which are useful as medicines. The invention provides compounds represented by the general formula (1):

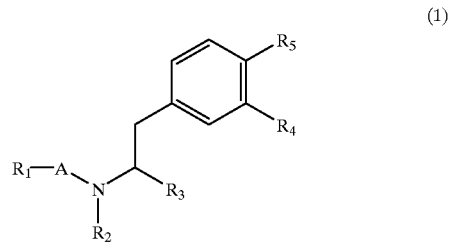

(1)

(wherein A is typically an amino acid residue, $R_1$ is typically $R_6$—CO—, $R_2$ is typically a hydrogen atom, $R_3$ is typically —CO—$R_7$, $R_4$ is typically an alkyl group, $R_5$ is typically a hydroxyl group, $R_6$ is typically an alkyl group, and $R_7$ is typically an amino group).

14 Claims, No Drawings

PHENETHYLAMINE DERIVATIVES

CROSS REFERENCE TO RELATED APPLICATION

The present application is the national stage under 35 U.S.C. 371 of PCT/JP98/03627, filed Aug. 14, 1998.

1. Technical Field

This invention relates to phenethylamine derivatives that typically function as a motilin receptor antagonist and which are useful as medicines.

2. Background Art

Motilin, which is one of the gastrointestinal hormones, is a straight-chained peptide consisting of 22 amino acids and is well known to be responsible for regulating the motility of the gastrointestinal tract in animals including human. It has been reported that exogenously administered motilin causes contractions in humans and dogs that are similar to interdigestive migrating contractions, thus promoting gastric emptying (Itoh et al., Scand. J. Gastroenterol., 11, 93–110 (1976); Peeters et al., Gastroenterology 102, 97–101 (1992)). Hence, erythromycin derivatives which are an agonist of motilin are under development as gastrointestinal tract motor activity enhancer (Satoh et al., J. Pharmacol. Exp. Therap., 271, 574–579 (1994); Lartey et al., J. Med. Chem., 38, 1793–1798 (1995); Drug of the Future, 19, 910–912 (1994)).

Peptide and polypeptide derivatives have been reported as antagonists of motilin receptors (Depoortere et al., Eur. J. Pharmacol., 286, 241–247 (1995); Poitras et al., Biochem. Biophys. Res. Commun., 205, 449–454 (1994); Takanashi et al., J. Pharmacol. Exp. Ther., 273, 624–628 (1995)). These derivatives are used as a pharmacological tool in the study of the action of motilin on the motility of the gastrointestinal tract and in the research and development of medicines in the field of the art contemplated by the invention.

Motilin receptors had been known to exist principally in the duodenum but recently it has been shown that they also exist in the large intestine, or the lower part of the gastrointestinal tract (William et al., Am. J. Physiol., 262, G50–G55 (1992)), and this indicates the possibility that motilin is involved not only in the motility of the upper part of the gastrointestinal tract but also in the motility of its lower part.

Reports have also been made of the cases of hypermotilinemia in patients with irritable bowel syndrome who were manifesting diarrhea and in patients with irritable bowel syndrome who were under stress (Preston et al., Gut, 26, 1059–1064 (1985); Fukudo et al., Tohoku J. Exp. Med., 151, 373–385 (1987)) and this suggests the possibility that increased blood motilin levels are involved in the disease. Other diseases that have been reported to involve hypermotilinemia include crohn's disease, ulcerative colitis, pancreatitis, diabetes mellitus, obesity, malabsorption syndrome, bacterial diarrhea, atrophic gastritis and postgastroenterectomy syndrome. The antagonists of motilin receptors have the potential to ameliorate irritable bowel syndrome and other diseased states accompanied by increased blood motilin levels.

DISCLOSURE OF INVENTION

An object of the invention is to provide phenethylamine derivatives that function as an antagonist of motilin receptors and which are useful as medicines.

The present inventors conducted repeated intensive studies in an attempt to develop compounds having an outstanding motilin receptor antagonistic action. As a result, they found that phenethylamine derivatives represented by the general formula (1) were an excellent antagonist of motilin receptors. The present invention has been accomplished on the basis of this finding.

Thus, the present invention provides compounds represented by the general formula (1), hydrates thereof or pharmaceutically acceptable salts thereof:

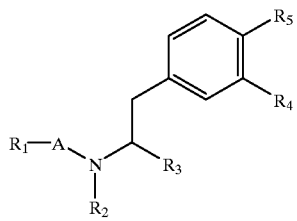

(1)

(wherein A is an amino acid residue or an Nα-substituted amino acid residue, provided that A binds with —NR$_2$— to form an amide;

R$_1$ is R$_6$—CO—, an optionally substituted straight-chained or branched alkyl group having 2–7 carbon atoms, an optionally substituted straight-chained or branched alkenyl group having 3–8 carbon atoms, or an optionally substituted straight-chained or branched alkynyl group having 3–8 carbon atoms;

R$_2$ is a hydrogen atom or an optionally substituted straight-chained or branched alkyl group having 1–3 carbon atoms;

R$_3$ is —CO—R$_7$, an optionally substituted straight-chained or branched alkyl group having 1–5 carbon atoms, an optionally substituted straight-chained or branched alkenyl group having 2–5 carbon atoms or an optionally substituted straight-chained or branched alkynyl group having 2–5 carbon atoms;

R$_4$ is a hydrogen atom, a straight-chained or branched alkyl group having 1–6 carbon atoms, a straight-chained or branched alkenyl group having 2–6 carbon atoms, a straight-chained or branched alkynyl group having 2–6 carbon atoms, or the general formula (2):

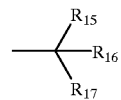

(2)

R$_5$ is a hydrogen atom or —OR$_8$;

R$_6$ is an optionally substituted straight-chained or branched alkyl group having 1–6 carbon atoms, an optionally substituted straight-chained or branched alkenyl group having 2–7 carbon atoms, an optionally substituted alkynyl group having 2–7 carbon atoms, a cycloalkyl group having 3–7 carbon atoms that may be fused to a benzene ring or a heterocyclic ring, an optionally substituted aromatic ring having 6–12 carbon atoms, an optionally substituted saturated or unsaturated heterocyclic ring having 3–12 carbon atoms, —N(R$_9$)R$_{10}$ or —OR$_{11}$;

R$_7$ is a hydrogen atom, an optionally substituted straight-chained or branched alkyl group having 1–5 carbon atoms, a cycloalkyl group having 3–7 carbon atoms, —N(R$_{12}$)R$_{13}$ or —OR$_{14}$;

$R_8$ is a hydrogen atom or a straight-chained alkyl group having 1–4 carbon atoms;

$R_9$ and $R_{10}$, which may be the same or different, each represent a hydrogen atom, an optionally substituted straight-chained or branched alkyl group having 1–5 carbon atoms, an optionally substituted straight-chained or branched alkenyl group having 2–6 carbon atoms, an optionally substituted straight-chained or branched alkynyl group having 2–6 carbon atoms, a cycloalkyl group having 3–6 carbon atoms that may be fused to a benzene ring or a heterocyclic ring, or an optionally substituted aromatic ring having 6–12 carbon atoms;

$R_{11}$ is an optionally substituted straight-chained or branched alkyl group having 1–5 carbon atoms, an optionally substituted straight-chained branched alkenyl group having 2–6 carbon atoms, an optionally substituted straight-chained or branched alkynyl group having 2–6 carbon atoms, a cycloalkyl group having 3–6 carbon atoms that may be fused to a benzene ring or a heterocyclic ring, or an optionally substituted aromatic ring having 6–12 carbon atoms;

$R_{12}$ and $R_{13}$, which may be the same or different, each represent a hydrogen atom, a straight-chained or branched alkyl group having 1–4 carbon atoms or a cycloalkyl group having 3–7 carbon atoms;

$R_{14}$ is a hydrogen atom, a straight-chained or branched alkyl group having 1–6 carbon atoms, or a cycloalkyl group having 3–7 carbon atoms;

$R_{15}$ is a hydrogen atom or a methyl group;

$R_{16}$ and $R_{17}$, are taken together and represent a cycloalkyl or cycloalkenyl group having 3–7 carbon atoms).

The present invention also provides a medicine containing a compound of the general formula (1) as an active ingredient. Further, the invention provides a motilin receptor antagonist containing said compound. The invention also provides a gastrointestinal motility suppressor containing said compound as an active ingredient. Further, the invention provides a therapeutic of hypermotilinemia containing said compound as an active ingredient.

In the definition of the compounds represented by the general formula (1), the amino acid residue as A may be of any types commonly known in the art, as exemplified by α-, β- and γ-amino acid residues. Specific examples include glycine (Gly), alanine (Ala), valine (Val), leucine (Leu), isoleucine (Ile), phenylalanine (Phe), tyrosine (Tyr), tryptophan (trp), histidine (His), asparagine (Asn), glutamine (Gln), aspartic acid (Asp), glutamic acid (Glu), lysine (Lys), serine (Ser), threonine (Thr), methionine (Met), proline (Pro), β-alanine (β-Ala), hydroxyproline (Hyp), citrulline (Cit), ornithine (Orn), phenylglycine (Phg), norvaline (Nva), aminoisobutyric acid (Aib), homophenylalanine (Hph), 2-thienylalanine (Thi), γ⁻ aminobutyric acid (γ-Abu), cyclohexylglycine (Chg), cyclohexylalanine (Cha), tert-leucine (Tle), aminoadipic acid (Aad), diaminobutyric acid (Dab), homoserine (Hse), aminobutyric acid (Abu), 2-aminobenzoic acid (2-Abz), thioproline (Thz), 1,2,3,4-tetrahydroisoquinoline-3-carboxylic acid (Tic), 1,2,3,4-tetrahydroisoquinoline-1-carboxylic acid (Tiq), 1-aminocyclopropanecarboxylic acid (Apc), 1-aminocyclobutanecarboxylic acid, 1-aminocyclopentanecarboxylic acid and 1-aminocyclohexanecarboxylic acid (Ahc); preferred are valine (Val), leucine (Leu), isoleucine (Ile), phenylalanine (Phe), tyrosine (Tyr), tryptophan (Trp), phenylglycine (Phg), hydroxyproline (Hyp), homophenylalanine (Hph), cyclohexylglycine (Chg), cyclohexylalanine (Cha), tert-leucine (Tle) and 2-thienylalanine; more preferred are valine (Val), leucine (Leu), isoleucine (Ile), phenylalanine (Phe), phenylglycine (Phg) and cyclohexylalanine (Cha). These amino acid residues and Nα-amino acid residues may be any of L-, D- and DL-forms, with the L-form being preferred.

The Nα-substituted amino acid residue as A is such that a hydrogen atom in the amino group in the α-position of any one of the above-mentioned α-amino acid residues is substituted. Examples of the substituent on the Nα-substituted amino acid residue include a straight-chained or branched alkyl group having 1–3 carbon atoms that may be substituted by a benzene ring and the like, and a methyl group is preferred.

Examples of the α-amino acid residue in the Nα-substituted amino acid residue as A include the amino acids mentioned above; preferred are Val, Leu, Ile, Phe, Tyr, Trp, Phg, Chg, Cha, Tle and Thi; more preferred are Val, Leu, Ile, Phe, Phg and Cha.

Examples of the Nα-substituted amino acid residue as A include N-methylvaline (N-Me-Val), N-methylleucine (N-Me-Leu), N-methylisoleucine (N-Me-Ile), N-methylphenylalanine (N-Me-Phe), N-methyltyrosine (N-Me-Tyr), N-methyltryptophan (N-Me-Trp), N-methylphenylglycine (N-Me-Phg), N-methylcyclohexylglycine (N-Me-Chg), N-methylcyclohexylalanine (N-Me-Cha), N-methyl-tert-leucine (N-Me-Tle), and N-methyl-2-thienylalanine (N-Me-Thi); preferred are N-Me-Val, N-Me-Leu, N-Me-Ile, N-Me-Phe, N-Me-Phg and N-Me-Cha; more preferred are N-Me-Val and N-Me-Phg.

The definition of $R_1$ includes $R_6$—CO—, in which $R_6$ may be an optionally substituted straight-chained or branched alkyl group having 1–6 carbon atoms, preferably a straight-chained or branched alkyl group having 1–5 carbon atoms, more preferably a straight-chained or branched alkyl group having 2–3 carbon atoms, with an ethyl group being particularly preferred.

In the definition of $R_6$—CO— as $R_1$, $R_6$ may be an optionally substituted straight-chained or branched alkenyl group having 2–7 carbon atoms, preferably a straight-chained or branched alkenyl group having 4–6 carbon atoms.

In the definition of $R_6$—CO— as $R_1$, $R_6$ may be an optionally substituted straight-chained or branched alkynyl group having 2–7 carbon atoms, preferably a straight-chained or branched alkynyl group having 4–6 carbon atoms.

In the definition of $R_6$—CO— as $R_1$, $R_6$ may be an optionally substituted straight-chained or branched alkyl group having 1–6 carbon atoms, an optionally substituted straight-chained or branched alkenyl group having 2–7 carbon atoms or an optionally substituted straight-chained or branched alkynyl group having 2–7 carbon atoms, and exemplary substituents include an amino group, a methylamino group, an ethylamino group, a dimethylamino group, a trimethylammonium group, a hydroxyl group, a carboxyl group, an aminocarbonyl group, an aminocarbonylamino group, a pyridylthio group, a methylthio group, a phenyl group, a 3-indolyl group, a 4-hydroxyphenyl group, a 2-thienyl group, a 2-furyl group, a 3-imidazolyl group and a cyclohexyl group; preferred are an amino group, a methylamino group, a phenyl group, a 3-indolyl group, a 4-hydroxyphenyl group, a 2-thienyl group, a 2-furyl group and a cyclohexyl group; more preferred are an amino group and a phenyl group. The above-mentioned alkyl, alkenyl and alkynyl groups may have one or more of the above-mentioned substituents, which may be the same or different.

In the definition of $R_6$—CO— as $R_1$, $R_6$ may be an optionally substituted straight-chained or branched alkyl group having 1–6 carbon atoms, preferably a straight-chained or branched alkyl group of 2–3 carbon atoms having one or more of the above-mentioned substituents, which may be the same or different; notably, a 1-amino-2-phenylethyl group, a 1-methylamino-2-phenylethyl group, a 1-amino-2-(3-indolyl)ethyl group, a 1-amino-2-(4-hydroxy) phenylethyl group, a 1-amino-2-(2-thienyl)ethyl group, a 1-amino-2-(2-furyl)ethyl group, a 1-amino-2-cyclohexylethyl group and a 2-phenylpropyl group are preferred, and a 1-amino-2-phenylethyl group is particularly preferred.

In the definition of $R_6$—CO— as $R_1$, $R_6$ may be an optionally substituted straight-chained or branched alkenyl group having 2–7 carbon atoms, preferably a straight-chained or branched alkenyl group of 4–6 carbon atoms having one or more of the above-mentioned substituents.

In the definition of $R_6$—CO— as $R_1$, $R_6$ may be an optionally substituted straight-chained or branched alkynyl group having 2–7 carbon atoms, preferably a straight-chained or branched alkynyl group of 4–6 carbon atoms having one or more of the above-mentioned substituents.

In the definition of $R_6$—CO— as $R_1$, $R_6$ may be a cycloalkyl group having 3–7 carbon atoms that may be fused to a benzene ring or a heterocyclic ring, and examples of the heterocyclic ring include aliphatic or aromatic 5- or 6-membered rings containing one or two hetero atoms selected from among O, N and S; specific examples include pyridine, pyrazine, furan, thiophene, pyrrole and imidazole.

In the definition of $R_6$—CO— as $R_1$, $R_6$ may be a cycloalkyl group having 3–7 carbon atoms that may be fused to a benzene ring or a heterocyclic ring, preferably a cycloalkyl group having 3–7 carbon atoms that is fused to a benzene ring, with a 1-benzocyclobutyl group being particularly preferred.

In the definition of $R_6$—CO— as $R_1$, $R_6$ may be an optionally substituted aromatic ring having 6–12 carbon atoms, as exemplified by a benzene ring and a naphthalene ring.

In the definition of $R_6$—CO— as $R_1$, $R_6$ may be an optionally substituted aromatic ring having 6–12 carbon atoms and exemplary substituents include a hydroxyl group, a methoxy group, a phenoxy group, a benzyloxy group, a tert-butyloxy group, an amino group, a methylamino group, a dimethylamino group, an ethylamino group, a carboxyl group, and a methoxycarbonyl group. The aromatic ring may have one or more of the above-mentioned substituents, which may be the same or different.

In the definition of $R_6$—CO— as $R_1$, $R_6$ may be an optionally substituted saturated or unsaturated heterocyclic ring having 3–12 carbon atoms, as exemplified by aliphatic or aromatic 5- to 10-membered monocyclic or fused rings containing one or more hetero atoms selected from among O, N and S; specific examples include pyrrolidine, piperidine, piperazine, tetrahydroisoquinoline, pyridine, pyrazine, furan, thiophene, pyrrole, imidazole, quinoline, indole, benzimidazole and benzofuran.

In the definition of $R_6$—CO— as $R_1$, $R_6$ may be an optionally substituted saturated or unsaturated heterocyclic ring having 3–12 carbon atoms and exemplary substituents include a hydroxyl group, a methoxy group, a phenoxy group, a benzyloxy group, a tert-butyloxy group, an amino group, a methylamino group, a dimethylamino group, an ethylamino group, a carboxyl group and a methoxycarbonyl group. The heterocyclic ring may have one or more of the above-mentioned substituents, which may be the same or different.

In the definition of $R_6$—CO— as $R_1$, $R_6$ may be an optionally substituted saturated or unsaturated heterocyclic ring having 3–12 carbon atoms, as exemplified by the above-mentioned heterocyclic rings that may have one or more of the above-mentioned substituents, which may be the same or different.

In the definition of $R_6$—CO— as $R_1$, $R_6$ may be —N($R_9$)$R_{10}$, in which $R_9$ and $R_{10}$ may each represent an optionally substituted straight-chained or branched alkyl group having 1–5 carbon atoms, preferably a straight-chained or branched alkyl group having 1–4 carbon atoms, more preferably a straight-chained alkyl group having 1–2 carbon atoms, with a methyl group being particularly preferred.

In the definition of $R_6$—CO— as $R_1$, $R_6$ may be —N($R_9$)$R_{10}$, in which $R_9$ and $R_{10}$ may each represent an optionally substituted straight-chained or branched alkenyl group having 2–6 carbon atoms, preferably a straight-chained or branched alkenyl group having 3–6 carbon atoms.

In the definition of $R_6$—CO— as $R_1$, $R_6$ may be —N($R_9$)$R_{10}$, in which $R_9$ and $R_{10}$ may each represent an optionally substituted straight-chained or branched alkynyl group having 2–6 carbon atoms, preferably a straight-chained or branched alkynyl group having 3–6 carbon atoms.

In the definition of $R_6$—CO— as $R_1$, $R_6$ may be —N($R_9$)$R_{10}$, in which $R_9$ and $R_{10}$ each represent an optionally substituted straight-chained or branched alkyl group having 1–5 carbon atoms, an optionally substituted straight-chained or branched alkenyl group having 2–6 carbon atoms or an optionally substituted straight-chained or branched alkynyl group having 2–6 carbon atoms. Exemplary substituents include an amino group, a hydroxyl group, a carboxyl group, an aminocarbonyl group, an aminocarbonylamino group, a pyridylthio group, a methylthio group, a phenyl group, a 3-indolyl group, a 4-hydroxyphenyl group, a 2-thienyl group, a 2-furyl group, a 3-imidazolyl group, and a cyclohexyl group; preferred are an amino group, a phenyl group, a 3-indolyl group, a 4-hydroxyphenyl group, a 2-thienyl group, a 2-furyl group and a cyclohexyl group; more preferred is a phenyl group. These alkyl, alkenyl and alkynyl groups may have one or more of the above-mentioned substituents, which may be the same or different.

In the definition of $R_6$—CO— as $R_1$, $R_6$ may be —N($R_9$)$R_{10}$, in which $R_9$ and $R_{10}$ may each represent an optionally substituted straight-chained or branched alkyl group having 1–5 carbon atoms, preferably a methyl group having one or more of the above-mentioned substituents, more preferably a benzyl group, a 3-indolylmethyl group, a p-hydroxybenzyl group, a 2-thienylmethyl group, a 2-furylmethyl group or a cyclohexylmethyl group, with a benzyl group being particularly preferred.

In the definition of $R_6$—CO— as $R_1$, $R_6$ may be —N($R_9$)$R_{10}$, in which $R_9$ and $R_{10}$ may each represent an optionally substituted straight-chained or branched alkenyl group having 2–6 carbon atoms, preferably a straight-chained or branched alkenyl group having 3–6 carbon atoms.

In the definition of $R_6$—CO— as $R_1$, $R_6$ may be —N($R_9$)$R_{10}$, in which $R_9$ and $R_{10}$ may each represent an optionally substituted straight-chained or branched alkynyl group having 2–6 carbon atoms, preferably a straight-chained or branched alkynyl group having 3–6 carbon atoms.

In the definition of $R_6$—CO— as $R_1$, $R_6$ may be —N($R_9$)$R_{10}$, in which $R_9$ and $R_{10}$ may each represent a cycloalkyl group having 3–6 carbon atoms that may be fused to a benzene ring or a heterocyclic ring, and the heterocyclic ring may be exemplified by aliphatic or aromatic 5- or 6-membered ring containing one or two hetero atoms selected from among O, N and S; specific examples of such heterocyclic ring include pyridine, pyrazine, furan, thiophene, pyrrole and imidazole.

In the definition of $R_6$—CO— as $R_1$, $R_6$ may be —N($R_9$)$R_{10}$, in which $R_9$ and $R_{10}$ may each represent a cycloalkyl group having 3–6 carbon atoms that may be fused to a benzene ring or a heterocyclic ring, and such cycloalkyl group is a cyclopropyl group, a cyclobutyl group, a cyclopentyl group or a cyclohexyl group.

In the definition of $R_6$—CO— as $R_1$, $R_6$ may be —N($R_9$)$R_{10}$, in which $R_9$ and $R_{10}$ may each represent a cycloalkyl group having 3–6 carbon atoms that may be fused to a benzene ring or a heterocyclic ring, as exemplified by a cycloalkyl group having 3–6 carbon atoms that may be fused to a benzene ring or one or more of the heterocyclic rings mentioned above.

In the definition of $R_6$—CO— as $R_1$, $R_6$ may be —N($R_9$)$R_{10}$, in which $R_9$ and $R_{10}$ may each represent an optionally substituted aromatic ring having 6–12 carbon atoms, as exemplified by a benzene ring and a naphthalene ring.

In the definition of $R_6$—CO— as $R_1$, $R_6$ may be —N($R_9$)$R_{10}$, in which $R_9$ and $R_{10}$ may each represent an optionally substituted aromatic ring having 6–12 carbon atoms, and exemplary substituents include a hydroxyl group, a methoxy group, a phenoxy group, a benzyloxy group, a tert-butyloxy group, an amino group, a methylamino group, a dimethylamino group, an ethylamino group, a carboxyl group and a methoxycarbonyl group. The aromatic ring may have one or more of these substituents, which may be the same or different.

While $R_9$ and $R_{10}$ in —N($R_9$)$R_{10}$ in $R_6$ in $R_6$—CO— as $R_1$ has the definitions set forth above, —N($R_9$)$R_{10}$ is preferably a benzylamino group or a benzylmethylamino group.

In the definition of $R_6$—CO— as $R_1$, $R_6$ may be —O$R_{11}$, in which $R_{11}$ may be an optionally substituted straight-chained or branched alkyl group having 1–5 carbon atoms, preferably a straight-chained or branched alkyl group having 1–4 carbon atoms, more preferably a straight-chained alkyl group having 1–2 carbon atoms, with a methyl group being particularly preferred.

In the definition of $R_6$—CO— as $R_1$, $R_6$ may be —O$R_{11}$, in which $R_{11}$ may be an optionally substituted straight-chained or branched alkenyl group having 2–6 carbon atoms, preferably a straight-chained or branched alkenyl group having 3–6 carbon atoms.

In the definition of $R_6$—CO— as $R_1$, $R_6$ may be —O$R_{11}$, in which $R_{11}$ may be an optionally substituted straight-chained or branched alkynyl group having 2–6 carbon atoms, preferably a straight-chained or branched alkynyl group having 3–6 carbon atoms.

In the definition of $R_6$—CO— as $R_1$, $R_6$ may be —O$R_{11}$, in which $R_{11}$ is an optionally substituted straight-chained or branched alkyl group having 1–5 carbon atoms, an optionally substituted straight-chained or branched alkenyl group having 2–6 carbon atoms or an optionally substituted straight-chained or branched alkynyl group having 2–6 carbon atoms. Exemplary substituents include an amino group, a hydroxyl group, a carboxyl group, an aminocarbonyl group, an aminocarbonylamino group, a pyridylthio group, a methylthio group, a phenyl group, a 3-indolyl group, a 4-hydroxyphenyl group, a 2-thienyl group, a 2-furyl group, a 3-imidazolyl group and a cyclohexyl group; preferred are an amino group, a phenyl group, a 3-indolyl group, a 4-hydroxyphenyl group, a 2-thienyl group, a 2-furyl group and a cyclohexyl group; more preferred is a phenyl group. The above-mentioned alkyl, alkenyl and alkynyl groups may have one or more of the above-mentioned substituents, which may be the same or different.

In the definition of $R_6$—CO— as $R_1$, $R_6$ may be —O$R_{11}$, in which $R_{11}$ may be an optionally substituted straight-chained or branched alkyl group having 1–5 carbon atoms, preferably a methyl group having one or more of the above-mentioned substituents, more preferably a benzyl group, a 3-indolylmethyl group, a p-hydroxybenzyl group, a 2-thienylmethyl group, a 2-furylmethyl group, and a cyclohexylmethyl group, with a benzyl group being particularly preferred.

In the definition of $R_6$—CO— as $R_1$, $R_6$ may be —O$R_{11}$, in which $R_{11}$ may be an optionally substituted straight-chained or branched alkenyl group having 2–6 carbon atoms, preferably a straight-chained or branched alkenyl group having 3–6 carbon atoms.

In the definition of $R_6$—CO— as $R_1$, $R_6$ may be —O$R_{11}$, in which $R_{11}$ may be an optionally substituted straight-chained or branched alkynyl group having 2–6 carbon atoms, preferably a straight-chained or branched alkynyl group having 3–6 carbon atoms.

In the definition of $R_6$—CO— as $R_1$, $R_6$ may be —O$R_{11}$, in which $R_{11}$ may be a cycloalkyl group having 3–6 carbon atoms that may be fused to a benzene ring or a heterocyclic ring, and the heterocyclic ring may be exemplified by an aliphatic or aromatic 5- or 6-membered ring containing one or two hetero atoms selected from among O, N and S. Specific examples of such heterocyclic ring include pyridine, pyrazine, furan, thiophene, pyrrole and imidazole.

In the definition of $R_6$—CO— as $R_1$, $R_6$ may be —O$R_{11}$, in which $R_{11}$ may be a cycloalkyl group having 3–6 carbon atoms that may be fused to a benzene ring or a heterocyclic ring, and the cycloalkyl group is a cyclopropyl group, a cyclobutyl group or a cyclopentyl group.

In the definition of $R_6$—CO— as $R_1$, $R_6$ may be —O$R_{11}$, in which $R_{11}$ may be a cycloalkyl group having 3–6 carbon atoms that may be fused to a benzene ring or a heterocyclic ring, as exemplified by a cycloalkyl group having 3–6 carbon atoms that may be fused to a benzene ring or one or more of the above-mentioned heterocyclic rings.

In the definition of $R_6$—CO— as $R_1$, $R_6$ may be —O$R_{11}$, in which $R_{11}$ may be an optionally substituted aromatic ring having 6–12 carbon atoms, as exemplified by a benzene ring and a naphthalene ring.

In the definition of $R_6$—CO— as $R_1$, $R_6$ may be —O$R_{11}$, in which $R_{11}$ may be an optionally substituted aromatic ring having 6–12 carbon atoms, and exemplary substituents include a hydroxyl group, a methoxy group, a phenoxy group, a benzyloxy group, a tert-butyloxy group, an amino group, a methylamino group, a dimethylamino group, an ethylamino group, a carboxyl group, and a methoxycarbonyl group. The aromatic ring may have one or more of the above-mentioned substituents, which may be the same or different.

In the definition of $R_6$—CO— as $R_1$, $R_6$ may be —O$R_{11}$, in which $R_{11}$ may be an optionally substituted aromatic ring having 6–12 carbon atoms, as exemplified by a benzene ring and a naphthalene ring that optionally have one or more of the above-mentioned substituents, which may be the same or different.

While $R_{11}$ in —O$R_{11}$ in $R_6$ in $R_6$—CO— as $R_1$ has the definitions set forth above, —O$R_8$ is preferably a benzyloxy group.

While $R_6$ in $R_6$—CO— as $R_1$ has the definitions set forth above, preferred examples of $R_6$ include a 1-amino-2-phenylethyl group, a 1-methylamino-2-phenylethyl group, a 1-amino-2-(3-indolyl)ethyl group, a 1-amino-2-(4-hydroxy)phenylethyl group, a 1-amino-2-(2-thienyl)ethyl group, a 1-amino-2-(2-furyl)ethyl group, a 1-amino-2- cyclohexylethyl group, a 2-phenylpropyl group, a 1-benzocyclobutyl group, a benzylamino group and a benzyloxy group, with a 1-amino-2-phenylethyl group being particularly prefered.

In its definition, $R_1$ may be an optionally substituted straight-chained or branched alkyl group having 2–7 carbon atoms, preferably a straight-chained or branched alkyl group having 3–4 carbon atoms, with a propyl group being particularly preferred.

In its definition, $R_1$ may be an optionally substituted straight-chained or branched alkenyl group having 3–8 carbon atoms, preferably a straight-chained or branched alkenyl group having 4–8 carbon atoms, more preferably a straight-chained or branched alkenyl group having 5–7 carbon atoms.

In its definition, $R_1$ may be an optionally substituted straight-chained or branched alkynyl group having 3–8 carbon atoms, preferably a straight-chained or branched alkynyl group having 3–7 carbon atoms, more preferably a straight-chained or branched alkynyl group having 5–7 carbon atoms.

In its definition, $R_1$ may be an optionally substituted straight-chained or branched alkyl group having 2–7 carbon atoms, an optionally substituted straight-chained or branched alkenyl group having 3–8 carbon atoms, or an optionally substituted straight-chained or branched alkynyl group having 3–8 carbon atoms. Exemplary substituents include an amino group, a methylamino group, an ethylamino group, a dimethylamino group, a hydroxyl group, a carboxyl group, an aminocarbonyl group, an aminocarbonylamino group, a pyridylthio group, a methylthio group, a phenyl group, a 3-indolyl group, a 4-hydroxyphenyl group, a 2-thienyl group, a 2-furyl group, a 3-imidazolyl group, and a cyclohexyl group; preferred are an amino group, a phenyl group, a 3-indolyl group, a 4-hydroxyphenyl group, a 2-thienyl group, a 2-furyl group, and a cyclohexyl group; more preferred are an amino group and a phenyl group. The above-described alkyl, alkenyl and alkynyl groups may have one or more of the above-mentioned substituents, which may be the same or branched.

The optionally substituted straight-chained or branched alkyl group as $R_1$ which has 2–7 carbon atoms is preferably a straight-chained or branched alkyl group of 3–4 carbon atoms that has one or more of the above-mentioned substituents, which may be the same or different. Preferred examples include a 2-amino-3-phenylpropyl group, a 2-amino-3-(3-indolyl)propyl group, a 2-amino-3-(4-hydroxy)phenylpropyl group, a 2-amino-3-(2-thienyl)propyl group, a 2-amino-3-(2-furyl)propyl group, a 2-amino-3-cyclohexylpropyl group, and a 3-phenylbutyl group, with a 2-amino-3-phenyhlpropyl group being particularly preferred.

The optionally substituted straight-chained or branched alkenyl group as $R_1$ which has 3–8 carbon atoms is preferably a straight-chained or branched alkenyl group of 4–8 carbon atoms that has one or more of the above-mentioned substituents.

The optionally substituted straight-chained or branched alkynyl groups as $R_1$ which has 2–7 carbon atoms is preferably a straight-chained or branched alkynyl group of 3–7 carbon atoms that has one or more of the above-mentioned substituents.

While $R_1$ has the definitions set forth above, it is preferably a phenylalanyl group, an N-Me phenylalanyl group, a β-(3-indolyl)alanyl group, a tyrosyl group, a β-(2-thienyl) alanyl group, a β-(2-furyl)alaninoyl group, a β-cyclohexylalanyl group, a 3-phenylbutyryl group, a 1-benzocyclobutylcarbonyl group, a benzylaminocarbonyl group or a benzyloxycarbonyl group, with a phenylalanyl group being particularly preferred.

In its definition, $R_2$ may be an optionally substituted straight-chained or branched alkyl group having 1–3 carbon atoms, as exemplified by a methyl group, an ethyl group, a propyl group and an isopropyl group; preferred are a methyl group and an ethyl group, and a methyl group is more preferred.

Exemplary substituents for the optionally substituted straight-chained or branched alkyl group as $R_2$ which has 1–3 carbon atoms include a phenyl group, a hydroxyl group, an amino group and a carboxyl group. The alkyl group may optionally have one or more of these substituents, which may be the same or different.

The optionally substituted straight-chained or branched alkyl group as $R_2$ which has 1–3 carbon atoms is preferably a methyl group.

While $R_2$ has the definitions set forth above, it is preferably a hydrogen atom or a methyl group.

In its definition, $R_3$ may be —CO—$R_7$, in which $R_7$ may be an optionally substituted straight-chained or branched alkyl group having 1–5 carbon atoms, preferably a straight-chained or branched alkyl group having 1–3 carbon atoms.

In its definition, $R_3$ may be —CO—$R_7$, in which $R_7$ may be an optionally substituted straight-chained or branched alkyl group having 1–5 carbon atoms, and exemplary substituents include a halogen, an amino group, a hydroxyl group and an alkoxy group, with halogen being preferred.

In its definition, $R_3$ may be —CO—$R_7$, in which $R_7$ may be an optionally substituted straight-chained or branched alkyl group having 1–5 carbon atoms, preferably a straight-chained or branched alkyl group having 1–3 carbon atoms and having one or more of the above-mentioned substituents which are the same as each other, more preferably a fluoromethyl group or a chloromethyl group.

In its definition, $R_3$ may be —CO—$R_7$, in which $R_7$ may be a cycloalkyl group having 3–7 carbon atoms, preferably a cycloalkyl group having 3–5 carbon atoms.

In its definition, $R_3$ may be —CO—$R_7$, in which $R_7$ may be N($R_{12}$)$R_{13}$, wherein $R_{12}$ and $R_{13}$ may be a straight-chained or branched alkyl group having 1–4 carbon atoms, preferably a straight-chained alkyl group having 1–2 carbon atoms, more preferably a methyl group.

In its definition, $R_3$ may be —CO—$R_7$, in which $R_7$ may be N($R_{12}$)$R_{13}$, wherein $R_{12}$ and $R_{13}$ may be a cycloalkyl group having 3–7 carbon atoms, preferably a cycloalkyl group having 3–5 carbon atoms.

In its definition, $R_3$ may be —CO—$R_7$, in which $R_7$ may be N($R_{12}$)$R_{13}$, wherein $R_{12}$ and $R_{13}$, which may be the same or different, are preferably a hydrogen atom or a methyl group.

While $R_{12}$ and $R_{13}$ in —N($R_{12}$)$R_{13}$ in $R_7$ in —CO—$R_7$ as $R_3$ have the definitions set forth above, —N($R_9$)$R_{10}$ is preferably an amino group or a methylamino group.

In its definition, $R_3$ may be —CO—$R_7$, in which $R_7$ may be —O$R_{14}$, wherein $R_{14}$ may be a straight-chained or branched alkyl group having 1–6 carbon atoms, preferably a straight-chained alkyl group having 1–2 carbon atoms, more preferably a methyl group.

In its definition, $R_3$ may be —CO—$R_7$, in which $R_7$ may be —O$R_{14}$, wherein $R_{14}$ may be a cycloalkyl group having 3–7 carbon atoms, which is a cyclopropyl group, a cyclobutyl group, a cyclopentyl group, a cyclohexyl group or a cycloheptyl group, with a cyclopropyl group being preferred.

While $R_{14}$ in —O$R_{14}$ in $R_7$ in —CO—$R_7$ as $R_3$ has the definitions set forth above, —O$R_{14}$ is preferably a hydroxyl group or a methoxy group.

While —CO—R₇ as R₃ has the definitions set forth above, it is preferably an amido group or an N-methylamido group.

In its definition, R₃ may be an optionally substituted straight-chained or branched alkyl group having 1–5 carbon atoms, preferably a straight-chained or branched alkyl group having 1–3 carbon atoms, with a methyl group being particularly preferred.

In its definition, R₃ may be an optionally substituted straight-chained or branched alkenyl group having 2–5 carbon atoms, preferably a straight-chained or branched alkenyl group having 2–3 carbon atoms.

In its definition, R₃ may be an optionally substituted straight-chained or branched alkynyl group having 2–5 carbon atoms, preferably a straight-chained alkynyl group having 2–3 carbon atoms.

In its definition, R₃ may be an optionally substituted straight-chained or branched alkyl group having 1–5 carbon atoms, an optionally substituted straight-chained or branched alkenyl group having 2–5 carbon atoms or an optionally substituted straight-chained or branched alkynyl group having 2–5 carbon atoms. Exemplary substituents include an amino group, an alkylamino group, a hydroxyl group, an alkoxy group, a carboxyl group, a halogen, etc., with an amino group being particularly preferred. The above-described alkyl, alkenyl and alkynyl groups may optionally have one or more of the above-mentioned substituents, which may be the same or different.

The optionally substituted straight-chained or branched alkyl group as R₃ which has 1–5 carbon atoms is preferably a methyl group and an aminomethyl group.

While R₃ has the definitions set forth above, it is preferably an amido group, an N-methylamido group, a methyl group or an aminomethyl group, with an amido group and a methyl group being particularly preferred.

In its definition, R₄ may be a straight-chained or branched alkyl group having 1–6 carbon atoms, preferably a straight-chained or branched alkyl group having 2–5 carbon atoms, more preferably a branched alkyl group having 3–5 carbon atoms, with a tert-butyl group being particularly preferred.

In its definition, R₄ may be a straight-chained or branched alkenyl group having 2–6 carbon atoms, preferably a straight-chained or branched alkenyl group having 3–5 carbon atoms, more preferably a branched alkenyl group having 3–5 carbon atoms.

In its definition, R₄ may be a straight-chained or branched alkynyl group having 2–6 carbon atoms, preferably a straight-chained or branched alkynyl group having 3–5 carbon atoms, more preferably a branched alkynyl group having 3–5 carbon atoms.

In its definition, R₄ may have the general formula (2), in which R₁₅ is preferably a methyl group.

In the general formula (2) as R₄, R₁₆ and R₁₇ are taken together and may form a cycloalkyl group having 3–7 carbon atoms, which is preferably a cycloalkyl group having 3–5 carbon atoms.

In the general formula (2) as R₄, R₁₆ and R₁₇ are taken together and may alternatively form a cycloalkenyl group having 3–7 carbon atoms, which is preferably a cycloalkenyl group having 4–6 carbon atoms.

The preferred examples of R₄ are an isopropyl group, a tert-butyl group, a 1,1-dimethylpropyl group, and a 1,1-dimethyl-2-propenyl group, with a tert-butyl group being particularly preferred.

In its definition, R₅ may represent —OR₁₂, in which R₁₂ may be a straight-chained alkyl group having 1–4 carbon atoms, preferably a methyl group and an ethyl group, more preferably a methyl group.

The preferred examples of R₅ are a hydroxyl group and a methoxy group, with a hydroxyl group being particularly preferred.

The preferred examples of the compound represented by the general formula (1):

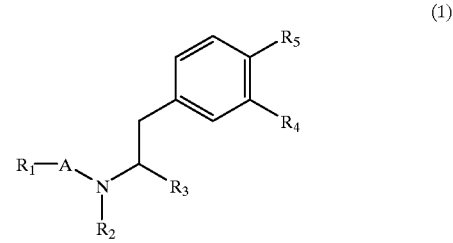

(1)

(where R₁, R₂, R₃, R₄ and R₅ have the same meanings as defined above) are: Phe-Hyp-Tyr(3-tBu)-NH₂, Phe-Thz-Tyr(3-tBu)-NH₂, Phe-Pro-Tyr(3-tBu)-NH₂, Phe-Phg-Tyr(3-tBu)-NH₂, Phe-Phg-Phe(3-tBu-4-methoxy)-NH₂, Phe-N-Me-Phg-Tyr(3-tBu)-NH₂, Phe-N-Me-D-Phg-Tyr(3-tBu)-NH₂, Phe-Phe-Tyr(3-tBu)-NH₂, Phe-Cha-Tyr(3-tBu)-NH₂, Phe-Chg-Tyr(3-tBu)-NH₂, Phe-Tle-Tyr(3-tBu)-NH₂, Phe-Val-Tyr(3-tBu)-NH₂, Phe-Leu-Tyr(3-tBu)-NH₂, Phe-Tyr-Tyr(3-tBu)-NH₂, Phe-Hph-Tyr(3-tBu)-NH₂, Phe-Thi-Tyr(3-tBu)-NH₂, Phe-Ile-Tyr(3-tBu)-NH₂, Phe-Thr-Tyr(3-tBu)-NH₂, Phe-Trp-Tyr(3-tBu)-NH₂, Tyr-Phg-Tyr(3-tBu)-NH₂, Phg-Phg-Tyr(3-tBu)-NH₂, Trp-Phg-Tyr(3-tBu)-NH₂, Cha-Phg-Tyr(3-tBu)-NH₂, Hph-Phg-Tyr(3-tBu)-NH₂, N-(α-methylhydrocinnamyl)-Phg-Tyr(3-tBu)-NH₂, Phe-N-Me-Val-Tyr(3-tBu)-NH₂, N-(α-methylhydrocinnamyl)-N-Me-D-Phg-Tyr(3-tBu)-NH₂, Phe-Val-N-Me-Tyr(3-tBu)-NH₂, Phe-Phg-Tyr(3-tBu)-NHMe, Phg-Phg-Tyr(3-tBu)-OH, N-(3-phenylbutyryl)-Phg-Tyr(3-tBu)-NH₂, N-(benzylaminocarbonyl)-N-Me-D-Phe-Tyr(3-tBu)-NH₂, N-(benzyloxycarbonyl)-Phg-Tyr(3-tBu)-NH₂, N-(benzyloxycarbonyl)-N-Me-Val-Tyr(3-tBu)-NH₂, N-(S)-3-phenylbutyryl-Phg-Tyr(3-tBu)-NH₂, N-((R)-3-phenylbutyryl)-Phg-Tyr(3-tBu)-NH₂, L-α-(3-methyl-2-butenyl)glycyl-N-Me-Val-Tyr(3-tBu)-NH₂, α-(4-pentynyl)glycyl-N-Me-Val-Tyr(3-tBu)-NH₂, N-(2-amino-3-phenylpropyl)-Phg-Tyr(3-tBu)-NH₂, N-(2-amino-3-phenylpropyl)-Val-Tyr(3-tBu)-NH₂, N-[2-(3-tert-butyl-4-hydroxyphenyl)-1-methylethyl]-3-methyl-2-(N-methyl-N-phenylalanylamino)butanamide, Phe-N-Me-Val-N-Me-Tyr(3-tBu)-NH₂, and N-[2-(3-tert-butyl-4-hydroxyphenyl)-1-methylethyl]-3-methyl-2-[N-methyl-N-(N-Me-phenylalanyl)amino]butanamide, and the more preferred examples are: Phe-Phg-Tyr(3-tBu)-NH₂, Phe-N-Me-D-Phg-Tyr(3-tBu)-NH₂, Phe-Phe-Tyr(3-tBu)-NH₂, Phe-Cha-Tyr(3-tBu)-NH₂, Phe-Val-Tyr(3-tBu)-NH₂, Phe-Leu-Tyr(3-tBu)-NH₂, Phe-Tyr-Tyr(3-tBu)-NH₂, Phe-Hph-Tyr(3-tBu)-NH₂, Phe-Ile-Tyr(3-tBu)-NH₂, Trp-Phg-Tyr(3-tBu)-NH₂, Cha-Phg-Tyr(3-tBu)-NH₂, Phe-N-Me-Val-Tyr(3-tBu)-NH₂, Phe-Val-N-Me-Tyr(3-tBu)-NH₂, Phe-Phg-Tyr(3-tBu)-NHMe, N-(benzylaminocarbonyl)-N-Me-D-Phe-Tyr(3-tBu)-NH₂, N-(S)-3-phenyl-butyryl-Phg-Tyr(3-tBu)-NH₂, N-(2-amino-3-phenylpropyl)-Phg-Tyr(3-tBu)-NH₂, N-(2-amino-3-phenylpropyl)-Val-Tyr(3-tBu)-NH₂, N-[2-(3-tert-butyl-4-hydroxyphenyl)-1-methylethyl]-3-methyl-2-(N-methyl-N-phenylalanylamino)butanamide, Phe-N-Me-Val-N-Me-Tyr(3-tBu)-NH₂, and N-[2-(3-tert-butyl-4-hydroxyphenyl)-1-methylethyl]-3-methyl-2-[N-methyl-N-(N-Me-phenylalanyl)amino]butanamide.

Salt-forming acids include inorganic acids such as hydrochloric acid, hydrobromic acid, hydroiodic acid, sulfuric acid and phosphoric acid, as well as organic acids such as acetic acid, oxalic acid, maleic acid, fumaric acid, citric acid, tartaric acid, methanesulfonic acid and trifluoroacetic acid.

The compounds of the present invention can occur as optical isomers and the respective optical isomers and mixtures thereof are all included within the scope of the invention.

The compounds of the invention can also be obtained as hydrates.

BEST MODE FOR CARRYING OUT THE INVENTION

The compounds represented by the general formula (1)

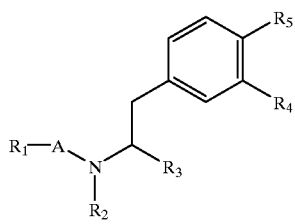

(1)

(where A, $R_1$, $R_2$, $R_3$, $R_4$ and $R_5$ respectively have the same meanings as defined above) are amino acid derivatives containing dipeptides or tripeptides and can be produced by either the solid-phase process or the liquid-phase process. In the production by the solid-phase process, an automatic organic synthesizer is typically used but it may be replaced by a manual procedure.

Almost all amino acids that compose the compounds of the invention are commercially available and readily purchasable. Those which are not commercially available can be produced by well-known established methods such as the Strecker synthesis, the Bucherer method, the acetamide malonate ester method, and the method of alkylating a glycine ester of which amino group is protected.

To produce p-hydroxy-m-substituted phenylalanine esters, tyrosine esters [Tyr-OR$_{14}$ (where $R_{14}$ has the same meaning as defined above)] which are either commercially available or obtainable by esterifying tyrosine are subjected to conventional procedures of organic synthesis, for example, the Friedel-Crafts reaction in the presence of proton acids or Lewis acids so that the substituent $R_4$ (which is a special case of the foregoing definition where $R_4$ is an alkyl group, an alkenyl group or an alkynyl group; this restriction applies to the present paragraph) is introduced in m-position. Note that the substituent $R_4$ need not be introduced only at this stage but may be introduced at any stage of the production.

If the α-amino group in the p-hydroxy-m-substituted phenylalanine ester is O-alkylated after protection with, for example, a benzyloxycarbonyl, one can obtain a product in which $R_8$ in —$OR_8$ is an alkyl group. If $R_5$ in the product is a hydrogen atom or an alkoxy group, it is subsequently Nα-alkylated to give a product where $R_2$ is an alkyl group. The hydroxyl group as $R_5$ is N-alkylated after protection with, for example, a benzyl group or any other group that can be readily removed at a later stage, and then deprotected to give a product where $R_2$ is an alkyl group and $R_5$ is a hydroxyl group.

Depending on $R_3$, a desired structure can be obtained by performing various conversions using ester groups of substituted phenylalanine esters in which the amino acid group and others are appropriately protected.

Take, for example, the case where $R_3$ is an amide; the α-amino group protected substituted phenylalanine ester is directly reacted with the amine $HN(R_{12})R_{13}$ or condensed with the amine $HN(R_{12})R_{13}$ after being converted to a carboxylic acid in the useful manner, whereby the ester is converted to an α-amino group protected substituted phenylalanine amide.

If $R_3$ is a substituted alkyl group, the α-amino group protected substituted phenylalanine ester is reduced to an aldehyde or an alcohol which, in turn, are converted to a halogen-substituted alkyl group, a hydroxyalkyl group, an aminoalkyl group, a methyl group, and so forth.

Almost all types of Nα-substituted amino acids are commercially available and readily purchasable; those which are not commercially available can be produced by well-known established methods such as the one of reacting α-bromocarboxylic acid units with a primary amine (J. Med. Chem., 37, 2678 (1994)) and the one of treating an amino group protected amino acid or an ester thereof with a base and an alkylating agent to effect its N-alkylation.

The Nα-amino group, as well as β-Ala and γ-Abu amino groups in amino acids can efficiently be protected with a fluorenyl methyloxycarbonyl (Fmoc) group, a tert-butoxycarbonyl (Boc) group, a benzyloxycarbonyl (Z) group and the like. A group that is preferably used to protect amino groups in solid-phase synthesis is an Fmoc group. Functional groups in side chains can be protected in various ways with various groups; the carboxyl group in the Asp, Glu or Aad residue is protected as a tert-butyl ester (OtBu); the hydroxyl group in the Ser, Thr or Tyr residue is protected with a tert-butyl (tBu) group; the hydroxyl group in the Hse residue is protected with a triphenylmethyl (Trt) group; the imidazolyl group in the His residue, the side-chain amino group in the Dab, Orn or Lys residue or the indole group in the tryptophan residue is protected with a Boc group. Note that amino acid residues can be protected with other protective groups.

Various methods may be used to activate the carboxyl group and they include: the use of benzotriazol-1-yl-oxy-tris(dimethylamino)phosphonium hexafluorophosphate (BOP); the use of O-(7-azabenzotriazol-1-yl)-1,1,3,3-tetramethyluronium hexafluorophosphate (HATU); the use of diisopropyl carbodiimide (DIC); N-ethyl-N'-3-dimethylaminopropyl carbodiimide (WSCI); the use of dicyclohexyl carbodiimide (DCC); the use of diphenylphosphorylazide (DPPA); the combination of one of these reagents with 1-hydroxybenzotriazole (HOBT) or N-hydroxysuccinimide (HONSu); the mixed acid anhydride method using isobutyl chloroformate etc.; the use of an amino acid in which the α-carboxyl group is in the form of a pentafluorophenyl ester (OPfp), an amino acid in which the α-carboxyl group is in the form of a p-nitrophenyl ester (ONP), or an amino acid in which the α-carboxyl group is in the form of an N-hydroxysuccinimide ester (OSu); the combination of one of these amino acids with HOBT. If necessary, a base such as triethylamine (TEA), diisopropylethylamine (DIEA), N-methylmorpholine (NMM) or 4-dimethylaminopyridine (DMAP) may be added to accelerate the reaction.

A compound in which $R_1$ is $N(R_9)R_{10}$—CO— (where $R_9$ and $R_{10}$ have the same meanings as defined above) can be produced via various processes including the mixing, under stirring, of an amino acid (A) with a reagent such as N,N'-carbonyldiimidazole, phosgene, triphosgene or p-nitrophenyl chlorocarbonate, followed by addition of $HN(R_9)R_{10}$, as well as the reacting of dipeptide units with $R_9(R_{10})N=C=O$ or $R_9(R_{10})NC(=O)Cl$.

A compound in which $R_1$ is $R_{11}O$—CO— can be produced via various processes including the coupling of a substituted phenylalanine amide with N—$(CO_2R_{11})$-amino acid and the reacting of the amino group in an amino acid (A) moiety with $ClCO_2R_{11}$.

To produce a compound in which $R_1$ is an alkyl group, an alkenyl group or an alkynyl group, a corresponding alkyl halide or aldehyde having the substituent protected as required is used to alkylate the amino group in an amino acid (A) moiety in the usual manner, optionally followed by deprotection.

The compounds of the invention can also be produced by applying the specific methods of production to be described in the examples that follow.

The subject application claims priority on the basis of Japanese Patent Application Nos. 255879/1997 and 186802/1998 and all disclosures in their specifications shall be incorporated herein by reference.

EXAMPLES

On the pages that follow, the production of the compounds of the invention is described more specifically by reference to examples, to which the invention is by no means limited. In the following examples, unless otherwise noted, the amino acid residues and Nα-amino acid residues are in the L-form.

In order to demonstrate the utility of the compounds of the invention, representative examples of them were subjected to pharmacological tests on the motilin receptor antagonistic action and the results are described under Tests. The chemical structural formulae or chemical names of the compounds produced in the examples are set forth in Tables A-1 to A-7 and Tables B-1 to B-11.

TABLE A-1

| Example No. | Structural formula or chemical name |
|---|---|
| 1 | Phe-Hyp-Tyr(3-tBu)-NH$_2$ |
| 2 | Phe-Tic-Tyr(3-tBu)-NH$_2$ |
| 3 | Phe-Thz-Tyr(3-tBu)-NH$_2$ |
| 4 | Phe-2-Abz-Tyr(3-tBu)-NH$_2$ |
| 5 | Phe-Phg-Tyr(3-tBu)-NH$_2$ |
| 6 | Phe-D-Hyp-Tyr(3-tBu)-NH$_2$ |
| 7 | Phe-Pro-Tyr(3-tBu)-NH$_2$ |
| 8 | Phe-D-Pro-Tyr(3-tBu)-NH$_2$ |
| 9 | Phe-Phg-Phe(3-tBu-4-methoxy)-NH$_2$ |
| 10 | Phe-Phe-Tyr(3-tBu)-NH$_2$ |
| 11 | Phe-Val-Tyr(3-tBu)-NH$_2$ |
| 12 | Phe-Phg-Tyr-NH$_2$ |
| 13 | Phe-Ala-Tyr(3-tBu)-NH$_2$ |
| 14 | Phe-Leu-Tyr(3-tBu)-NH$_2$ |
| 15 | Val-Phg-Tyr(3-tBu)-NH$_2$ |
| 16 | Leu-Phg-Tyr(3-tBu)-NH$_2$ |
| 17 | Phe-Gly-Tyr(3-tBu)-NH$_2$ |

TABLE A-2

| Example No. | Structural formula or chemical name |
|---|---|
| 18A | Phe-N-Me-Phg-Tyr(3-tBu)-NH$_2$ |
| 18B | Phe-N-Me-D-Phg-Tyr(3-tBu)-NH$_2$ |
| 19 | N-benzyl-N-(4-pyridylthioacetyl)-Phg-Tyr(3-tBu)-NH$_2$ |
| 20 | Phe-Phg-tYR(3-tBu)-OH |
| 21 | Phe-Tyr-Tyr(3-tBu)-NH$_2$ |
| 22 | Phe-Hph-Tyr(3-tBu)-NH$_2$ |
| 23 | Phe-Thi-Tyr(3-tBu)-NH$_2$ |
| 24 | Phe-β-Ala-Tyr(3-tBu)-NH$_2$ |
| 25 | Phe-γ-Abu-Tyr(3-tBu)-NH$_2$ |
| 26 | Phe-Aib-Tyr(3-tBu)-NH$_2$ |
| 27 | Phe-Ile-Tyr(3-tBu)-NH$_2$ |
| 28 | Phe-Chg-Tyr(3-tBu)-NH$_2$ |
| 29 | Phe-Cha-Tyr(3-tBu)-NH$_2$ |
| 30 | Phe-Tle-Tyr(3-tBu)-NH$_2$ |
| 31 | Phe-Asp-Tyr(3-tBu)-NH$_2$ |
| 32 | Phe-Glu-Tyr(3-tBu)-NH$_2$ |
| 33 | Phe-Aad-Tyr(3-tBu)-NH$_2$ |

TABLE A-3

| Example No. | Structural formula or chemical name |
|---|---|
| 34 | Phe-Asn-Tyr(3-tBu)-NH$_2$ |
| 35 | Phe-Gln-Tyr(3-tBu)-NH$_2$ |
| 36 | Phe-Cit-Tyr(3-tBu)-NH$_2$ |
| 37 | Phe-Dab-Tyr(3-tBu)-NH$_2$ |
| 38 | Phe-Orn-Tyr(3-tBu)-NH$_2$ |
| 39 | Phe-Lys-Tyr(3-tBu)-NH$_2$ |
| 40 | Phe-Ser-Tyr(3-tBu)-NH$_2$ |
| 41 | Phe-Hse-Tyr(3-tBu)-NH$_2$ |
| 42 | Phe-Thr-Tyr(3-tBu)-NH$_2$ |
| 43 | Phe-Abu-Tyr(3-tBu)-NH$_2$ |
| 44 | Phe-Nva-Tyr(3-tBu)-NH$_2$ |
| 45 | Phe-Met-Tyr(3-tBu)-NH$_2$ |
| 46 | Phe-His-Tyr(3-tBu)-NH$_2$ |
| 47 | Phe-Trp-Tyr(3-tBu)-NH$_2$ |
| 48 | Phe-Tiq-Tyr(3-tBu)-NH$_2$ |
| 49 | N-(4-pyridylthioacetyl)-Phg-Tyr(3-tBu)-NH$_2$ |
| 50 | N-(1-benzocyclobutanecarbonyl)-Phg-Tyr-(3-tBu)-NH$_2$ |

TABLE A-4

| Example No. | Structural formula or chemical name |
|---|---|
| 51 | N-(2-indolecarbonyl)-Phg-Tyr(3-tBu)-NH$_2$ |
| 52 | Tyr-Phg-Tyr(3-tBu)-NH$_2$ |
| 53 | Phg-Phg-Tyr(3-tBu)-NH$_2$ |
| 54 | Thi-Phg-Tyr(3-tBu)-NH$_2$ |
| 55 | Trp-Phg-Tyr(3-tBu)-NH$_2$ |
| 56 | His-Phg-Tyr(3-tBu)-NH$_2$ |
| 57 | N-((±)-3-phenylbutyryl)-Phg-Tyr(3-tBu)-NH$_2$ |

TABLE A-4-continued

| Example No. | Structural formula or chemical name |
|---|---|
| 58 | N-(2-biphenylcarbonyl)-Phg-Tyr(3-tBu)-NH$_2$ |
| 59 | β-Ala-Phg-Tyr(3-tBu)-NH$_2$ |
| 60 | Aib-Phg-Tyr(3-tBu)-NH$_2$ |
| 61 | Ile-Phg-Tyr(3-tBu)-NH$_2$ |
| 62 | Chg-Phg-Tyr(3-tBu)-NH$_2$ |
| 63 | Cha-Phg-Tyr(3-tBu)-NH$_2$ |
| 64 | Tle-Phg-Tyr(3-tBu)-NH$_2$ |
| 65 | Asp-Phg-Tyr(3-tBu)-NH$_2$ |
| 66 | Aad-Phg-Tyr(3-tBu)-NH$_2$ |
| 67 | Asn-Phg-Tyr(3-tBu)-NH$_2$ |

TABLE A-5

| Example No. | Structural formula or chemical name |
|---|---|
| 68 | Gln-Phg-Tyr(3-tBu)-NH$_2$ |
| 69 | Cit-Phg-Tyr(3-tBu)-NH$_2$ |
| 70 | Dab-Phg-Tyr(3-tBu)-NH$_2$ |
| 71 | Lys-Phg-Tyr(3-tBu)-NH$_2$ |
| 72 | Ser-Phg-Tyr(3-tBu)-NH$_2$ |
| 73 | Hse-Phg-Tyr(3-tBu)-NH$_2$ |
| 74 | Thr-Phg-Tyr(3-tBu)-NH$_2$ |
| 75 | Abu-Phg-Tyr(3-tBu)-NH$_2$ |
| 76 | Nva-Phg-Tyr(3-tBu)-NH$_2$ |
| 77 | Met-Phg-Tyr(3-tBu)-NH$_2$ |
| 78 | Pro-Phg-Tyr(3-tBu)-NH$_2$ |
| 79 | Hyp-Phg-Tyr(3-tBu)-NH$_2$ |
| 80 | Tic-Phg-Tyr(3-tBu)-NH$_2$ |
| 81 | Tiq-Phg-Tyr(3-tBu)-NH$_2$ |
| 82 | 2-Abz-Phg-Tyr(3-tBu)-NH$_2$ |
| 83 | Hph-Phg-Tyr(3-tBu)-NH$_2$ |
| 84 | N-(α-methylhydrocinnamoyl)-Phg-Tyr(3-tBu)-NH$_2$ |

TABLE A-6

| Example No. | Structural formula or chemical name |
|---|---|
| 85 | N-(α-methylcinnamoyl)-Phg-Tyr(3-tBu)-NH$_2$ |
| 86 | N-(3-quinolinecarbonyl)-Phg-Tyr(3-tBu)-NH$_2$ |
| 87 | N-(3-furanacryloyl)-Phg-Tyr(3-tBu)-NH$_2$ |
| 88 | Phe-D-Phg-Tyr(3-tBu)-NH$_2$ |
| 89 | Phe-N-Me-Val-Tyr(3-tBu)-NH$_2$ |
| 90 | N-(α-methylhydrocinnamoyl)-N-Me-B-Phg-Tyr(3-tBu)-NH$_2$ |
| 91 | Phe-Val-N-Me-Tyr(3-tBu)-NH$_2$ |
| 92 | Phe-Phg-Tyr(3-tBu)-NHMe |
| 93 | Phe-Apc-Tyr(3-tBu)-NHMe |
| 94 | Phe-Ahc-Tyr(3-tBu)-NHMe |
| 95 | N-acetyl-transHyp(O-benzyl)-Tyr(3-tBu)-NHMe |
| 96 | Phe-Cha-Phe(3-tBu)-NH$_2$ |
| 97 | N-(benzylaminocarbonyl)-N-Me-D-Phg-Tyr-(3-tBu)-NH$_2$ |
| 98 | N-(benzyloxycarbonyl)-Phg-Tyr(3-tBu)-NHMe |
| 99 | N-(benzyloxycarbonyl)-N-Me-Val-Tyr(3-tBu)-NH$_2$ |
| 100 | N-((R)-3-phenylbutyryl)-Phg-Tyr(3-tBu)-NH$_2$ |
| 101 | N-((S)-3-phenylbutyryl)-Phg-Tyr(3-tBu)-NH$_2$ |
| 102 | N-((R)-3-phenylbutyryl)-D-Phg-Tyr(3-tBu)-NH$_2$ |

TABLE A-7

| Example No. | Structural formula or chemical name |
|---|---|
| 103 | N-((S)-3-phenylbutyryl)-D-Phg-Tyr(3-tBu)-NH$_2$ |
| 104 | L-α-(3-methyl-2-butenyl)glycyl-N-Me-Val-Tyr-(3-tBu)-NH$_2$ |
| 105 | α-(4-pentynyl)glycyl-N-Me-Val-Tyr(3-tBu)-NH$_2$ |
| 106 | α-(2-butynyl)glycyl-N-Me-Val-Tyr(3-tBu)-NH$_2$ |
| 107 | N-((S)-3-phenylbutyryl)-N-Me-Val-Tyr(3-tBu)-NH$_2$ |
| 108 | N-((R)-3-phenylbutyryl)-N-Me-Val-Tyr(3-tBu)-NH$_2$ |
| 109 | N-(β-aminohydrocinnamoyl)-N-Me-Val-Tyr(3-tBu)-NH$_2$ |
| 110 | N-(2-amino-3-phenylpropyl)-Phg-Tyr(3-tBu)-NH$_2$ |
| 111 | N-(2-amino-3-phenylpropyl)-N-Me-Phg-Tyr(3-tBu)-NH$_2$ |
| 112 | N-(phenylpyruvinoyl)-N-Me-Val-Tyr(3-tBu)-NH$_2$ |
| 113 | N-phenyl-Gly-N-Me-Val-Tyr(3-tBu)-NH$_2$ |
| 114 | N-Me-N-phenyl-Gly-N-Me-Val-Tyr(3-tBu)-NH$_2$ |
| 115 | N-(3-phenylbutyl)-Val-Tyr(3-tBu)-NH$_2$ |
| 116 | N-(2-amino-3-phenylpropyl)-Val-Tyr(3-tBu)-NH$_2$ |
| 117 | 2-[(2-amino-3-phenylpropyl)amino]-N-[2-amino-1-[(3-tert-butyl-4-hydroxyphenyl)methyl)ethyl]-3-methylbutanamide |
| 118 | N-[2-(3-tert-butyl-4-hydroxyphenyl)-1-methylethyl]-3-methyl-2-(N-methyl-N-phenylalanylamino)butanamide |
| 119 | Phe-N-Me-Val-N-Me-Tyr(3-tBu)-NH$_2$ |
| 120 | N-[2-(3-tert-butyl-4-hydroxyphenyl)-1-methylethyl]-3-methyl-2-(N-methyl-N-Me-phenylalanylamino)butanamide |
| 121 | N-[2-(3-tert-butyl-4-hydroxyphenyl)-1-methylethyl]-N-Me-3-methyl-2-(N-methyl-N-phenylalanylamino)butanamide |

TABLE B-1
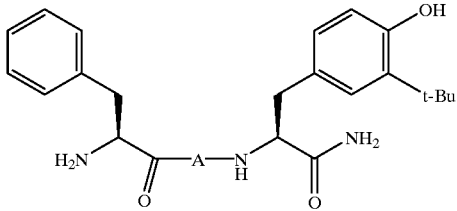
| Ex. No. | A | Ex. No. | A | Ex. No. | A |
|---|---|---|---|---|---|
| 1 | 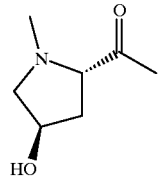 | 8 | 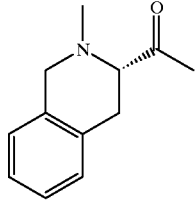 | 18B | 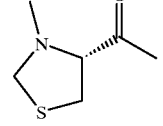 |
| 2 | 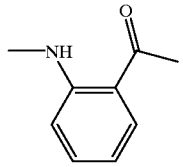 | 10 | 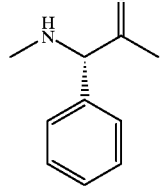 | 21 | 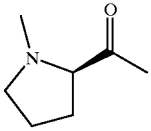 |
| 3 | 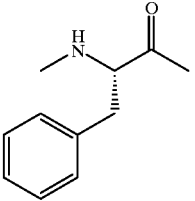 | 11 | 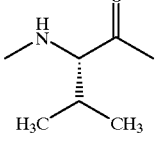 | 22 | 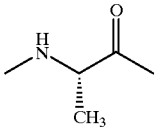 |
| 4 | 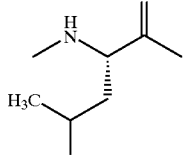 | 13 | 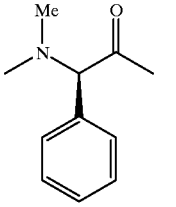 | 23 | 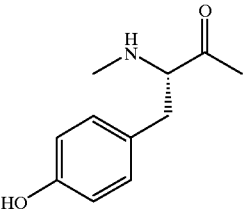 |
| 5 | 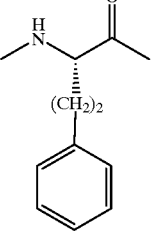 | 14 | 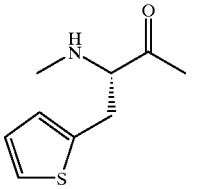 | 24 | 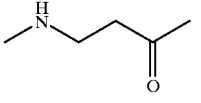 |

TABLE B-1-continued

| Ex. No. | A | Ex. No. | A | Ex. No. | A |
|---|---|---|---|---|---|
| 6 | (2S,4R)-4-hydroxy-1-methylpyrrolidine-2-carbonyl | 17 | N-methylglycyl (sarcosyl) | 25 | 4-(methylamino)butanoyl |
| 7 | (S)-1-methylpyrrolidine-2-carbonyl | 18A | (S)-N,N-dimethylphenylglycyl | 26 | 2-(methylamino)-2-methylpropanoyl |

TABLE B-2

| Ex. No. | A | Ex. No. | A | Ex. No. | A |
|---|---|---|---|---|---|
| 27 | (S)-N-methylisoleucyl | 34 | (S)-N-methylasparaginyl | 41 | (S)-N-methylhomoseryl |
| 28 | (S)-N-methyl-cyclohexylglycyl | 35 | (S)-N-methylglutaminyl | 42 | (S)-N-methylthreonyl |

TABLE B-2-continued

| Ex. No. | A | Ex. No. | A | Ex. No. | A |
| --- | --- | --- | --- | --- | --- |
| 29 | CH₂-cyclohexyl | 36 | (CH₂)₃-C(O)NH₂ | 43 | CH₂CH₃ (Abu) |
| 30 | CH₂-C(CH₃)₃ (tert-Leu side chain) | 37 | CH₂CH₂NH₂ | 44 | (CH₂)₂CH₃ (Nva) |
| 31 | CH₂-CO₂H (Asp) | 38 | (CH₂)₃NH₂ (Orn) | 45 | (CH₂)₂SCH₃ (Met) |
| 32 | (CH₂)₂-CO₂H (Glu) | 39 | (CH₂)₄NH₂ (Lys) | 46 | CH₂-imidazole (His) |
| 33 | (CH₂)₃-CO₂H | 40 | CH₂OH (Ser) | 47 | CH₂-indole (Trp) |

TABLE B-3
| Ex. No. | A | R5 | R4 |
|---|---|---|---|
| 9 | | OCH3 | t-Bu |
| 12 | | OH | H |
| 48 | | OH | t-Bu |
| 88 | | OH | t-Bu |
| 89 | | OH | t-Bu |
TABLE B-3-continued
| Ex. No. | A | R5 | R4 |
|---|---|---|---|
| 96 | | H | t-Bu |
TABLE B-4
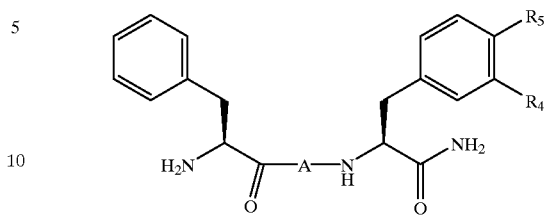
| Ex. No. | R1' | RA |
|---|---|---|
| 90 | | CH3 |
| 97 | | CH3 |
| 102 | | H |

TABLE B-4-continued
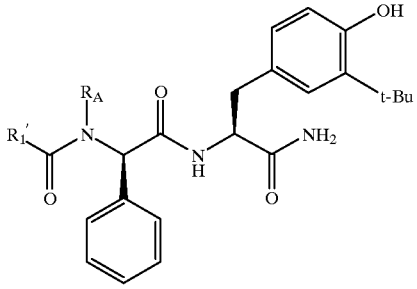
| Ex. No. | R₁' | R_A |
|---|---|---|
| 103 | 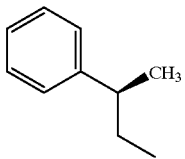 | H |
TABLE B-5
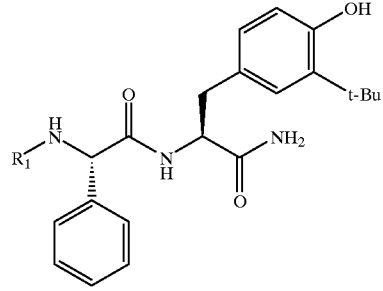
| Ex. No. | R₁ | Ex. No. | R₁ | Ex. No. | R₁ |
|---|---|---|---|---|---|
| 15 | 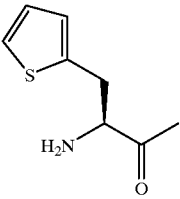 | 54 | 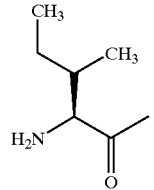 | 61 | 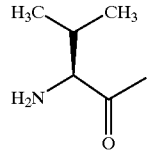 |
| 16 | 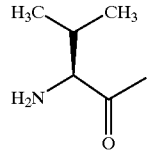 | 55 | 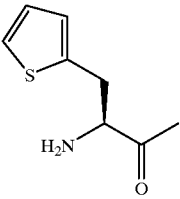 | 62 | 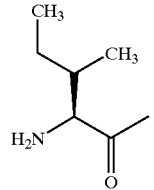 |

TABLE B-5-continued
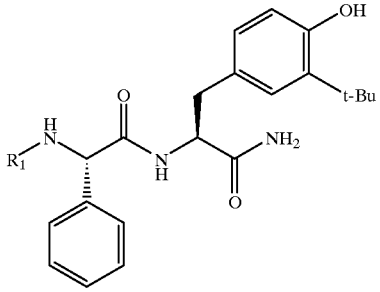
| Ex. No. | R₁ | Ex. No. | R₁ | Ex. No. | R₁ |
|---|---|---|---|---|---|
| 49 | 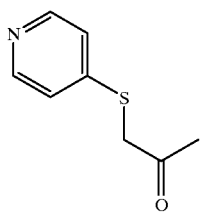 | 56 | 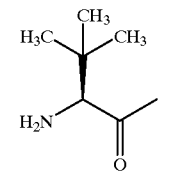 | 63 | 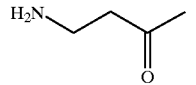 |
| 50 | 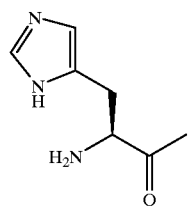 | 57 | 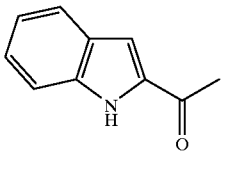 | 64 | 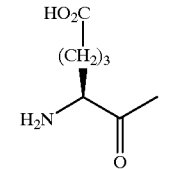 |
| 51 | 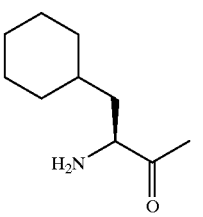 | 58 | 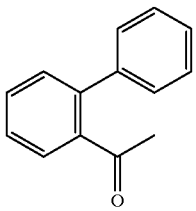 | 65 | 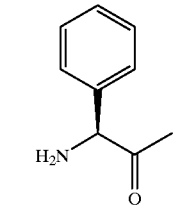 |
| 52 | 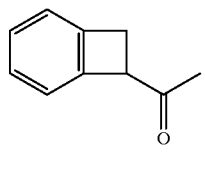 | 59 | 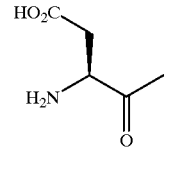 | 66 | 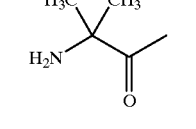 |
| 53 | 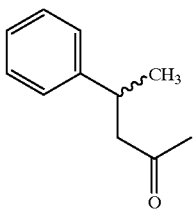 | 60 | 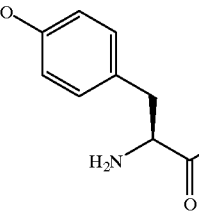 | 67 | 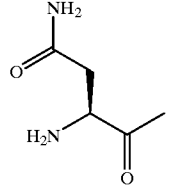 |

TABLE B-6
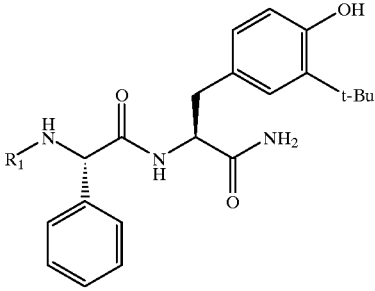
| Ex. No. | R₁ | Ex. No. | R₁ | Ex. No. | R₁ |
|---|---|---|---|---|---|
| 68 | 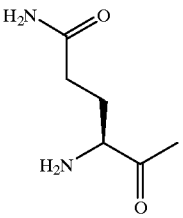 | 75 | 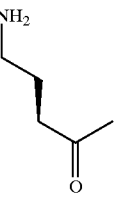 | 82 | 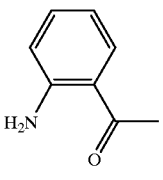 |
| 69 | 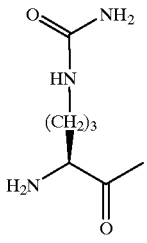 | 76 | 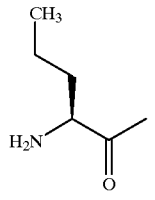 | 83 | 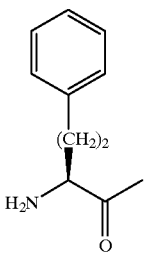 |
| 70 | 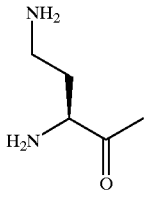 | 77 | 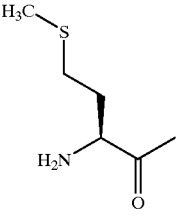 | 84 | 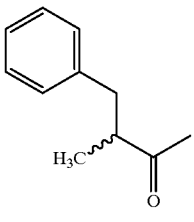 |
| 71 | 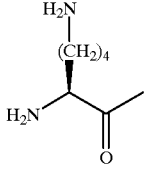 | 78 | 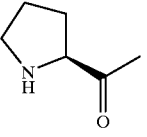 | 85 | 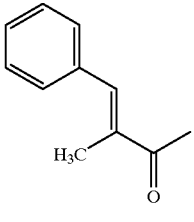 |
| 72 | 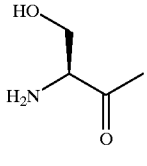 | 79 | 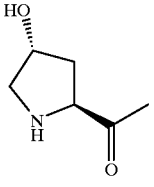 | 86 | 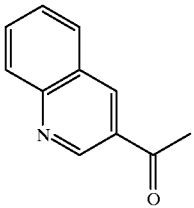 |

TABLE B-6-continued
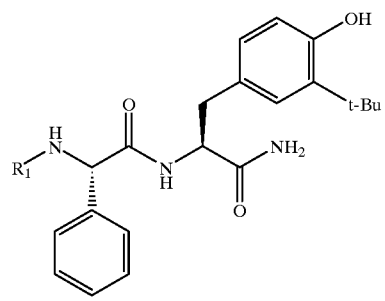
| Ex. No. | R₁ | Ex. No. | R₁ | Ex. No. | R₁ |
|---|---|---|---|---|---|
| 73 | 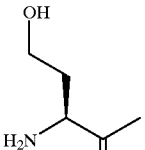 | 80 | 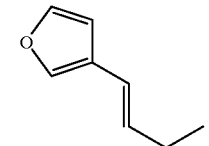 | 87 | 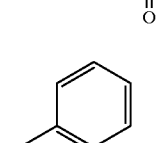 |
| 74 | 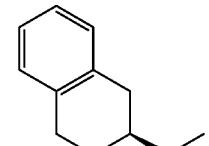 | 81 | 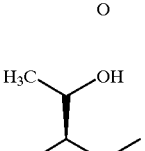 | | |
TABLE B-7
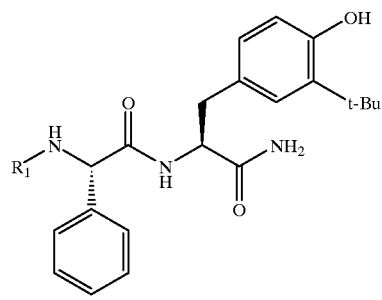
| Ex. No. | R₁ |
|---|---|
| 100 |  |
TABLE B-7-continued
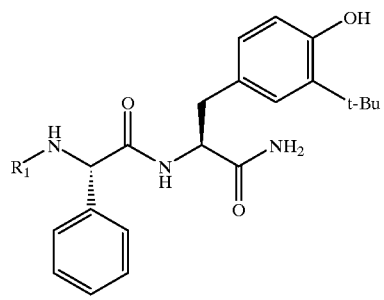
| Ex. No. | R₁ |
|---|---|
| 101 |  |

TABLE B-7-continued

[Structure: R₁-NH-CH(phenyl)-C(O)-NH-CH(CH₂-C₆H₃(OH)(t-Bu))-C(O)NH₂]

| Ex. No. | R₁ |
|---|---|
| 110 | CH(NH₂)(CH₂CH₃)-CH₂-phenyl |

TABLE B-8

[Structure: R₁-N(Me)-CH(iPr)-C(O)-NH-CH(CH₂-C₆H₃(OH)(t-Bu))-C(O)NH₂]

| Ex. No. | R₁ | Ex. No. | R₁ |
|---|---|---|---|
| 99 | benzyl-O-C(O)-CH₂- | 109 | phenyl-CH(NH₂)-CH₂-C(O)-CH₂- |
| 104 | (CH₃)₂C=CH-CH₂-CH(NH₂)-C(O)-CH₂- | 112 | phenyl-CH₂-C(O)-C(O)-CH₃ |
| 105 | HC≡C-CH₂-CH₂-CH₂-CH(NH₂)-C(O)-CH₃ | 113 | phenyl-NH-CH₂-C(O)-CH₃ |
| 106 | H₃C-C≡C-CH₂-CH(NH₂)-C(O)-CH₃ | 114 | phenyl-N(CH₃)-CH₂-C(O)-CH₃ |
| 107 | phenyl-CH(CH₃)-CH₂-C(O)-CH₃ (R) | | |
| 108 | phenyl-CH(CH₃)-CH₂-C(O)-CH₃ (S) | | |

TABLE B-9
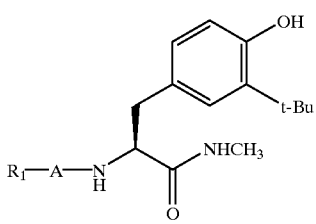
| Ex. No. | R₁—A— |
|---|---|
| 92 | 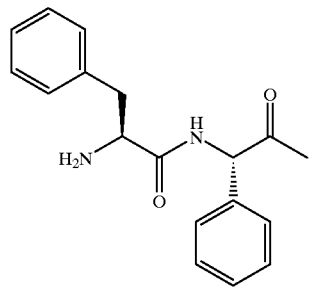 |
| 93 | 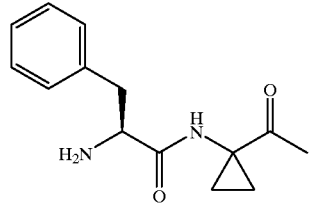 |
| 94 | 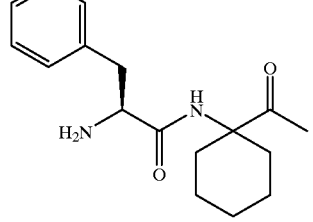 |
| 95 | 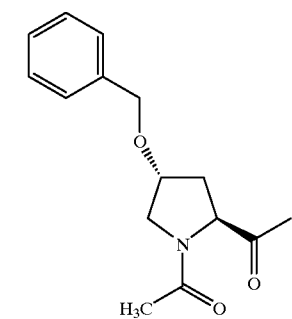 |
TABLE B-9-continued
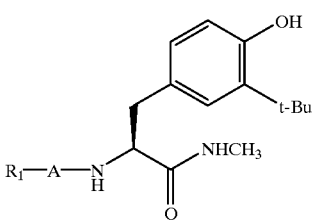
| Ex. No. | R₁—A— |
|---|---|
| 98 | 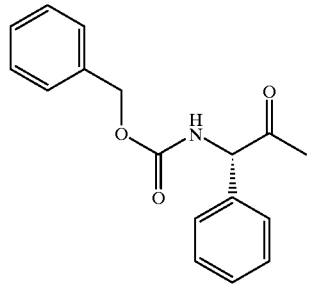 |
TABLE B-10
| Ex. No. | $R_1''$ | $R_A$ | $R_2$ | $R_3$ |
|---|---|---|---|---|
| 91 | H | H | CH₃ | —CONH₂ |
| 118 | H | CH₃ | H | CH₃ |
| 119 | H | CH₃ | CH₃ | —CONH₂ |
| 120 | CH₃ | CH₃ | H | CH₃ |
| 121 | H | CH₃ | CH₃ | CH₃ |

TABLE B-11

| Ex. No. | Structural Formula |
|---|---|
| 19 | |
| 20 | |
| 111 | |
| 115 | |
| 116 | |

TABLE B-11-continued

| Ex. No. | Structural Formula |
|---|---|
| 117 | 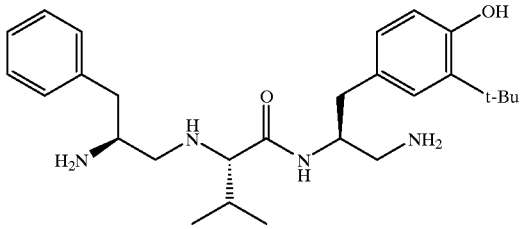 |

In the following examples, HPLC retention times (RT in minutes) were measured by either one of the following methods a–e.

Method a: HPLC was performed with HITACHI L-6300 using Waters μBONDASPHERE 5μ C18 300 Å (300 angstroms, 3.9×150 mm) as a column. The eluting solution A was 0.1% trifluoroacetic acid (TFA) in distilled water and the eluting solution B was 0.1% TFA in acetonitrile (MeCN). The linear gradient was created by 0–70% of solution B for 35 minutes at a flow rate of 1 ml/min. The detection wavelength was 280 nm (UV).

Method b: Same as method a, except that the linear gradient was created by 0–60% of solution B for 30 minutes at a flow rate of 1 ml/min.

Method c: Same as method a, except that the linear gradient was created by 20–60% of solution B for 40 minutes at a flow rate of 1 ml/min.

Method d: Same as method a, except that Waters μBONDASPHERE 5μ C18 100 Å (100 angstroms, 3.9×150 mm) was used as a column.

Method e: Same as method a, except that HPLC was performed with SHIMADZU LC-10AD.

If necessary, the crude product was purified by HPLC which was performed with Waters 600E or Gilson 306 using YMC-Pack ODS (120 angstroms, 250×20 mm I.D.) as a column. The eluting solution A was 0.1% TFA in distilled water and the eluting solution B was 0.1% TFA in MeCN. The linear gradient was created at a flow rate of 10 ml/min, and the detection wavelength was 280 nm (UV).

Mass spectra (MA) were taken by EI-MS using SHIMADZU GCMS-QP1000 or GCMS-QP5050A or by FAB-MS using JASCO 70-250SEQ.

NMR was measured by the following method f or g.
Method f: Burucher DX-500 (500 MHz) was used as a measuring instrument.
Method g: JEOL JNM-EX-270 (270 MHz) was used as a measuring instrument.

Various commercial resins can conveniently be used as a solid phase and they include Rink Amide Resin of NovaBiochem, Fmoc-2,4-dimethoxy-4'-(carboxymethyloxy)benzhydrylamine linked to Aminomethyl Resin of Bachem, and Wang Resin of Watanabe Kagaku K.K., which were used as appropriate in the following examples.

Coupling in solid-phase synthesis can conveniently be performed by the following first to fifth methods, which were used as appropriate in the following examples.

Method 1: Using 1.5–2 equivalents of an acid component (e.g. amino acid, Nα-substituted amino acid or carboxylic acid), 3 equivalents of BOP and 3 equivalents of HOBT (relative to resin), 3 ml of N,N-dimethylformamide (DMF) for 0.1 mmol of resin, and 6 equivalents of NMM, shaking was done for 1.5–2 hours.

Method 2: Using 1.5–2 equivalents of an acid component and 3 equivalents of HATU (relative to resin), 3 ml of DMF for 0.1 mmol of resin, and 6 equivalents of NMM, shaking was done for 1.5–2 hours.

Method 3: Using 1.5–2 equivalents of an acid component and 3 equivalents of HOBT (relative to resin), 3 ml of DMF for 0.1 mmol of resin, and 3.2 equivalents of DIC, shaking was done for 2 hours.

Method 4: Using 5 equivalents of an acid component and 0.1 equivalent of DMAP (relative to resin), 3 ml of DMF for 0.1 mmol of resin, and 5 equivalents of DIC, shaking was done for 4 hours.

Method 5: Using 2 equivalents of an active ester (e.g. Pfp ester) of an acid component and 3 equivalents of HOBT (relative to resin), and 3 ml of DMF for 0.1 mmol of resin, shaking was done for 2 hours.

For constructing Nα-substituted amino acid residues, the sixth method described below is convenient and was used in the following examples as appropriate.

Method 6: Using 10 equivalents of a substituted or unsubstituted bromoacetic acid, 3 ml of DMF for 0.1 mmol of resin, and 13 equivalents of DIC, shaking was done for 30 minutes; after filtering, reacylation was done under the same conditions and repeated washing was effected with DMF; 60 equivalents of an amine dissolved in dimethyl sulfoxide (DMSO) was added to the mixture, which was shaken for 2 hours.

The following is a specific procedure of solid-phase synthesis. The reaction vessel is charged with a solid-phase resin, such as Rink Amide Resin, which is swollen by addition of a suitable solvent such as DMF; subsequently, 20% piperidine/DMF is added and repeated washing is effected with DMF. To the washed mixture, an acid component is coupled by method 1. Using either one of the first to sixth coupling methods, the procedure is repeated as many times as the acid components to be coupled. The order of steps of deprotecting and cleaving the resin product is not fixed and they may be interchanged or performed simultaneously. The step of cleavage is completed by shaking in an aqueous solution of 95% TFA at room temperature for 30–45 minutes. After the end of the cleavage step, the resin is filtered off and the filtrate is concentrated and dried under reduced pressure to give a phenethylamine derivative in crude form.

The following is a specific method that may be employed to deprotect amino acids in solid-phase synthesis. If the resin is used in an amount of 0.025–0.1 mmol, an Fmoc group can be removed by a process consisting of the steps of adding 5 ml of 20% piperidine/DMF for 0.1 mmol of the resin, shaking for 5 minutes, filtering, then adding another 5 ml of 20% piperidine/DMF, shaking for 20–30 minutes, filtering and repeated washing with DMF. If the resin is used in an amount of 0.2 mmol, an Fmoc group can be removed by a process consisting of the steps of adding 7 ml of 20% piperidine/DMF, for 5 minutes, filtering, then adding another 7 ml of 20% piperidine/DMF, filtering and repeated washing with DMF. Boc, tBu and Trt groups can be removed in the cleavage step, with deprotection and cleavage being effected simultaneously.

Example 1

Phe-Hyp-Tyr(3-tBu)-NH$_2$ (1) Synthesis of Tyr(3-tBu)-OMe

To a solution of 25.0 g (0.108 mol) of Tyr-OMe.HCl in 500 ml of tert-butyl acetate, 18 ml (0.204 mol) of 70% HClO$_4$ was added and the mixture was stirred at room temperature for 4 days. The reaction mixture was concentrated under reduced pressure and the resulting residue was dissolved in 400 ml of ethyl acetate; thereafter, the solution was poured into 800 ml of a saturated aqueous solution of NaHCO$_3$ and the mixture was stirred. The organic layer was taken out and washed first with a saturated aqueous solution of NaHCO$_3$, then with saturated brine, dried with anhydrous sodium sulfate, and the solvent was distilled off under reduced pressure. To the resulting residue, 500 ml of ether was added and the mixture was stirred overnight at room temperature. The precipitating crystals were recovered by filtration to give Tyr(3-tBu)-OMe in the amount of 10.9 g (40%).

NMR(method g,DMSO-d6): δ 1.39(9H,s), 1.85(3H,brs), 2.81(1H,dd,J=14.0,7.6 Hz), 3.02(1H,dd,J=14.0,5.1 Hz), 3.70(1H,dd,J=7.6,5.1 Hz), 3.73(3H,s), 6.57(1H,d,J=8.2 Hz), 6.86(1H,dd,J=8.2,1.8 Hz), 7.04(1H,d,J=1.8 Hz).

(2) Synthesis of Fmoc-Tyr(3-tBu)-OH

To a solution of 2.0 g (8.0 mmol) of Tyr(3-tBu)-OMe in 40 ml of methanol, 8.8 ml (8.8 mmol) of 1 N aqueous sodium hydroxide was added dropwise under cooling with ice and the mixture was stirred for 2 hours, followed by stirring at room temperature for additional 4 hours. The reaction mixture was concentrated under reduced pressure and 1 N HCl was added under cooling with ice for pH adjustment to 9; to the reaction being maintained at pH 8–9, a solution of 3.0 g (8.8 mmol) of Fmoc-OSu in 1,4-dioxane (40 ml) and a saturated aqueous solution of sodium hydrogencarbonate were alternately added dropwise and the mixture was stirred at room temperature for 1 day. After being rendered acidic with hydrochloric acid, the reaction mixture was extracted with ethyl acetate and the ethyl acetate layer was dried with anhydrous magnesium sulfate and concentrated under reduced pressure. The resulting crude product was subjected to silica gel column chromatography (eluting solvents were ethyl acetate:n-hexane=1:1 and acetic acid supplemented ethyl acetate:n-hexane=1:1); to remove the acetic acid used in eluting, the fractions were washed with water, dried with anhydrous magnesium sulfate and concentrated under reduced pressure to give Fmoc-Tyr(3-tBu)-OH in the amount of 2.3 g (yield: 61%).

NMR(method g,CDCl$_3$): δ 1.38(9H,s), 3.09(2H,m), 4.19 (1H,m), 4.39(2H,d,J=7 Hz), 4.64(1H,m), 5.19(1H,d,J=8 Hz), 6.58(1H,d,J=8 Hz), 6.84(1H,d,J=8 Hz), 7.05(1H,brs), 7.26–7.77(8H,m).

(3) Synthesis of Phe-Hyp-Tyr(3-tBu)-NH$_2$

A reaction vessel was charged with 222 mg (0.1 mmol) of Rink Amide Resin (0.45 mmol/g); after being swelled with DMF, the resin was treated with piperidine to remove Fmoc. Subsequently, Fmoc-Tyr(3-tBu)-OH was coupled by method 1. After filtering and washing with DMF, the resin was treated with piperidine to remove Fmoc. Subsequently, Fmoc-Hyp-OH was coupled by method 2. After filtering and washing with DMF, the resin was treated again with piperidine to remove Fmoc. Subsequently, Boc-Phe-OH was coupled by method 2. After the end of the reaction, filtering, washing with DMF and washing with methylene chloride (DCM) were performed and cleavage was effected with 3 ml of a 95% aqueous solution of TFA. The reaction mixture was concentrated under reduced pressure and the residue was dissolved in 2 ml of DMF, followed by HPLC purification. The active fractions were collected, concentrated and freeze-dried to yield a TFA salt of the titled compound in the amount of 23.2 mg.

HPLC (method b):RT17.15; FAB-MS: 497(M+H$^+$); NMR (method f,DMSO-d6): δ 1.32(9H,s), 1.75(1H,ddd,J=13,8,5 Hz), 2.00(1H,dd,J=13,8 Hz), 2.76(1H,dd,J=14,8 Hz), 2.86 (1H,dd,J=14,6 Hz), 2.92(1H,dd,J=14,7 Hz), 3.09(1H,dd,J=14,6 Hz), 3.18(1H,dd,J=10,4 Hz), 3.54(1H,d,J=10 Hz), 4.25 (1H,brs), 4.29–4.38(2H,m), 4.46(1H,dd,J=8,8 Hz), 5.13(1H, d,J=3 Hz), 6.65(1H,d,J=8 Hz), 6.88(1H,dd,J=8,2 Hz), 7.01 (1H,d,J=2 Hz), 7.02(1H,s), 7.23–7.43(6H,m), 7.89(1H,d,J=8 Hz), 8.09(3H,brs), 9.09(1H,s).

Example 2

Phe-Tic-Tyr(3-tBu)-NH$_2$

Substituting Fmoc-Tic-OH for the Fmoc-Hyp-OH used in Example 1(3), the procedure of Example 1 was repeated to yield a TFA salt of the titled compound in the amount of 34.4 mg.

HPLC (method b):RT21.56; FAB-MS: 543(M+H$^+$); NMR (method g,DMSO-d6): δ 1.30(9H,s), 2.58–3.24(6H,m), 4.27–4.85(5H,m), 6.56–7.41(14H,m), 7.81–8.36(4H,m), 9.09–9.11(1H,m).

Example 3

Phe-Thz-Tyr(3-tBu)-NH$_2$

Substituting Fmoc-Thz-OH for the Fmoc-Hyp-OH used in Example 1(3), the procedure of Example 1 was repeated to yield a TFA salt of the titled compound in the amount of 20.2 mg.

HPLC (method b):RT19.31; FAB-MS: 499 (M+H$^+$); NMR(method g,DMSO-d6): δ 1.32(9H,s), 2.70–3.15(6H, m), 4.16(1H,d,J=9 Hz), 4.39(1H,m), 4.62(1H,m), 4.82(1H, t,J=7 Hz), 5.02(1H,d,J=9 Hz), 6.64(1H,d,J=8 Hz), 6.82–7.41 (9H,m), 8.00–8.13(4H,m), 9.10(1H,s).

Example 4

Phe-2-Abz-Tyr(3-tBu)-NH$_2$

Substituting Fmoc-2-ABz-OH for the Fmoc-Hyp-OH used in Example 1(3), the procedure of Example 1 was repeated to yield a TFA salt of the titled compound in the amount of 6.9 mg.

HPLC (method b):RT20.99; FAB-MS: 503(M+H$^+$); NMR (method g,DMSO-d6): δ 1.29(9H,s), 2.81–3.10(4H,m), 4.28 (1H,m), 4.52(1H,m), 6.64(1H,d,J=8 Hz), 6.94(1H,d,J=8 Hz), 7.14–7.68(11H,m), 8.14(1H,d,J=8 Hz), 8.31(2H,brs), 8.67(1H,d,J=8 Hz), 9.10(1H,s), 11.27(1H,s).

Example 5

Phe-Phg-Tyr(3-tBu)-NH$_2$

Substituting Fmoc-Phg-OH for the Fmoc-Hyp-OH used in Example 1(3), the procedure of Example 1 was repeated (except that Fmoc-Phg-OH and Boc-Phe-OH were coupled by method 1) to yield a TFA salt of the titled compound in the amount of 17.7 mg.

HPLC (method b):RT19.52; FAB-MS: 517(M+H$^+$); NMR (method f,DMSO-d6): δ 1.32(9H,s), 2.74(1H,dd,J=14,8 Hz), 2.89(1H,dd,J=14,5 Hz), 2.92(1H,dd,J=14,8 Hz), 3.07 (1H,dd,J=14,5 Hz), 4.17(1H,brs), 4.39(1H,ddd,J=8,8,5 Hz), 5.60(1H,d,J=8 Hz), 6.65(1H,d,J=8 Hz), 6.87(1H,dd,J=8,1 Hz), 6.98(1H,s), 7.06(1H,d,J=1 Hz), 7.10–7.50(11H,m), 8.09(3H,brs), 8.48(1H,d,J=8 Hz), 9.06(1H,d,J=8 Hz), 9.09 (1H,s).

Example 6

Phe-D-Hyp-Tyr(3-tBu)-NH$_2$ (1) Synthesis of Fmoc-D-Hyp-OH 262 mg (2.0 mmol) of D-Hyp-OH was dissolved in 5 ml of a saturated aqueous solution of sodium hydrogencarbonate under stirring and a mixture of 742 mg (2.2 mmol) of Fmoc-OSu and 10 ml of 1,4-dioxane was added dropwise under cooling with ice; thereafter, and the mixture was stirred at room temperature for 3 days. In the meantime, a saturated aqueous solution of sodium hydrogencarbonate was added as appropriate to keep the pH of the reaction mixture at 8–9. After being rendered acidic with hydrochloric acid under cooling with ice, the reaction mixture was subjected to extraction with ethyl acetate. The ethyl acetate layer was washed with water and saturated brine, dried with anhydrous magnesium sulfate and concentrated under reduced pressure. The resulting crude product was purified by silica gel column chromatography (eluting solvents were chloroform and acetic acid supplemented chloroform:methanol=10:1); to remove the acetic acid used in eluting, the fractions were once concentrated under reduced pressure and dissolved again in ethyl acetate; thereafter, the solution was washed with water, dried with anhydrous magnesium sulfate and concentrated under reduced pressure to give a colorless powder in the amount of 660 mg (93%).

NMR(method g,DMSO-d6): δ 1.89–2.29(2H,m), 3.26–3.56(3H,m), 4.10–4.47(4H,m), 5.15(1H,brs), 7.28–7.94(8H,m), 12.64(1H,brs).

(2) Synthesis of Phe-D-Hyp-Tyr(3-tBu)-NH$_2$

A reaction vessel was charged with 213 mg (0.1 mmol) of Rink Amide Resin (0.47 mmol/g); after being swelled with DMF, the resin was treated with pyridine to remove Fmoc. Subsequently, Fmoc-Tyr(3-tBu)-OH was coupled by method 1. After filtering and washing with DMF, the resin was treated with piperidine to remove Fmoc. Subsequently, Fmoc-D-Hyp-OH was coupled by method 2. After filtering and washing with DMF, the resin was treated with piperidine to remove Fmoc. Subsequently, Fmoc-Phe-OH was coupled by method 2. After filtering and washing with DMF, the resin was treated again with piperidine to remove Fmoc. After the end of the reaction, filtering, washing with DMF and washing with DCM were performed and cleavage was effected with 3 ml of a 95% aqueous solution of TFA. The reaction mixture was concentrated under reduced pressure and the residue was dissolved in 2 ml of DMF, followed by HPLC purification. The active fractions were collected, concentrated and freeze-dried to yield a TFA salt of the titled compound in the amount of 21.5 mg. HPLC (method d):RT16.68.

FAB-MS: 497(M+H$^+$); NMR(method g,DMSO-d6): δ 1.32(9H,s), 1.45–1.76(2H,m), 2.62–3.09(4H,m), 3.59–4.78 (6H,m), 5.14(1H,brs), 6.64(1H,d,J=8 Hz), 6.82(1H,d,J=6 Hz), 7.00(1H,s), 7.13(2H,s), 7.23–7.36(5H,m), 8.16(3H, brs), 8.41(1H,d,J=9 Hz), 9.08(1H,s).

Example 7

Phe-Pro-Tyr(3-tBu)-NH$_2$

Substituting Fmoc-Pro-OH.AcOEt for the Fmoc-D-Hyp-OH used in Example 6(2), the procedure of Example 6(2) was repeated to yield a TFA salt of the titled compound in the amount of 27.0 mg.

HPLC (method b):RT18.87; FAB-MS: 481(M+H$^+$); NMR (method g,DMSO-d6): δ 1.32(9H,s), 1.38–2.10(4H,m), 2.75 (1H,dd,J=14,9 Hz), 2.84–3.85(5H,m), 4.25–4.49(3H,m), 6.64(1H,d,J=8 Hz), 6.82–7.35(9H,m), 7.70–8.30(4H,m), 9.09(1H,s).

Example 8

Phe-D-Pro-Tyr(3-tBu)-NH$_2$

Substituting Fmoc-D-Pro-OH.AcOEt for the Fmoc-D-Hyp-OH used in Example 6(2), the procedure of Example 6(2) was repeated to yield a TFA salt of the titled compound in the amount of 33.6 mg.

HPLC (method b):RT19.87; FAB-MS: 481 (M+H$^+$); NMR(method g,DMSO-d6): δ 1.31(9H,s), 1.41–2.04(4H, m), 2.55–3.51(6H,m), 4.15–4.70(3H,m), 6.61–6.67(1H,m), 6.80–6.83(1H,m), 6.98–7.01(1H,m), 7.12–7.34(7H,m), 8.02–8.39(4H,m), 9.08(1H,s).

Example 9

Phe-Phg-Phe(3-tBu-4-methoxy)-NH$_2$ (1) Synthesis of Z-Tyr(3-t-Bu)-OMe

To a solution of Tyr(3-tBu)-OMe (1.1 g) in H$_2$O (10 ml), 0.7 g (6.57 mmol) of NaHCO$_3$ and 0.92 ml (6.57 mmol) of Z-Cl were added under cooling with ice and the mixture was stirred at room temperature for 1 hour. The reaction mixture was diluted with ethyl acetate and washed with water and saturated brine. The organic layer was dried with anhydrous sodium sulfate and concentrated under reduced pressure. The resulting residue was subjected to silica gel column chromatography (eluting solvent; ethyl acetate:n-hexane= 1:2) to give Z-Tyr(3-t-Bu)-OMe in the amount of 1.44 g (85%).

NMR(method g,CDCl$_3$): δ 1.36(9H,s), 3.04(2H, brd,J= 5.6 Hz), 3.72(3H,s), 4.57–4.68(1H,m), 4.97(1H,brs), 5.10 (2H,s), 5.20(1H, brd,J=7.9 Hz), 6.55(1H,d,J=7.9 Hz), 6.78 (1H,dd,J=2.0,7.9 Hz), 6.95(1H,d,J=2.0 Hz), 7.26–7.41(5H, m).

(2) Synthesis of Z-Phe(3-tBu-4-methoxy)-OMe

To a solution of Z-Tyr(3-tBu)-OMe (0.4 g) in acetone (3 ml), 0.22 g (1.56 mmol) of K$_2$CO$_3$ and 0.65 ml (10.4 mmol) of methyl iodide were added at room temperature and the mixture was heated under reflux for 5 hours. The reaction mixture was concentrated under reduced pressure and the resulting residue was subjected to silica gel column chromatography (eluting solvent; ethyl acetate:n-hexane=1:2) to give Z-Phe(3-tBu-4-methoxy)-OMe in the amount of 0.10 g (24%).

NMR(method g,CDCl$_3$): δ 1.33(9H,s), 3.05(2H, brd,J= 5.6 Hz), 3.72(3H,s), 3.81(3H,s), 4.57–4.68(1H,m), 5.10(2H, s), 5.19(1H, brd,J=7.9 Hz), 6.76(1H,d,J=8.2 Hz), 6.90(1H, dd,J=2.0,8.2 Hz), 6.96(1H,d,J=2.0 Hz), 7.26–7.40(5H,m).

(3) Synthesis of Phe(3-tBu-4-methoxy)-OMe

To a solution of Z-Phe(3-tBu-4-methoxy)-OMe (0.17 g) in methanol (2 ml), 10% palladium carbon (0.02 g) was added at room temperature and the mixture was stirred in a hydrogen atmosphere for 20 hours. The reaction mixture was filtered and the filtrate was concentrated under reduced pressure; the resulting residue was subjected to silica gel column chromatography (eluting solvent was ethyl acetate) to give Phe(3-tBu-4-methoxy)-OMe in the amount of 88 mg (77%).

EI-MS: 265(M$^+$); NMR(method g,CDCl$_3$): δ 1.35(9H,s), 2.81(1H,dd,J=13.6,7.8 Hz), 3.02(1H,dd,J=13.6,5.0 Hz), 3.67–3.71(1H,m), 3.73(3H,s), 3.81(3H,s), 6.80(1H,d,J=8.2 Hz), 7.00(1H,dd,J=2.0,8.2 Hz), 7.05(1H,d,J=2.0 Hz).

(4) Synthesis of Fmoc-Phe(3-tBu-4-methoxy)-OH

To a solution of 87 mg (0.33 mmol) of Phe(3-tBu-4-methoxy)-OMe in 2 ml of methanol, 0.4 ml (0.4 mmol) of 1 N aqueous sodium hydroxide was added dropwise under cooling with ice and the mixture was stirred for 1 hour, followed by stirring for additional 3 hours at room temperature. The reaction mixture was concentrated under reduced pressure and adjusted to pH 9 by addition of 1 N hydrochloric acid and a saturated aqueous solution of sodium hydrogencarbonate. To the thus adjusted reaction mixture, a solution of 122 mg (0.36 mmol) of Fmoc-OSu in 2 ml of 1,4-dioxane was added dropwise and the mixture was stirred for 3 hours at room temperature. The reaction mixture was rendered acidic with hydrochloric acid and extracted with ethyl acetate; the ethyl acetate layer was dried with anhydrous magnesium sulfate and concentrated under reduced pressure. The resulting crude product was purified by preparative thin-layer chromatography (developing solvents were CHCl$_3$ and CHCl$_3$:methanol=4:1) to give Fmoc-Phe(3-tBu-4-methoxy)-OH in the amount of 125 mg (80%).

NMR(method g,CDCl$_3$): δ 1.33(9H,s), 2.99–3.21(2H,m), 3.76(3H,s), 4.12(1H,m), 4.32(2H,m), 4.57(1H,brs), 5.25 (1H,d,J=6 Hz), 6.74(1H,d,J=8 Hz), 6.95(1H,d,J=8 Hz), 7.06 (1H,brs), 7.22–7.74(8H,m).

(5) Synthesis of Phe-Phg-Phe(3-tBu-4-methoxy)-NH$_2$

Substituting Fmoc-Phe(3-tBu-4-methoxy)-OH for the Fmoc-Tyr(3-tBu)-OH used in Example 5 and using 213 mg (0.1 mmol) of Rink Amide Resin (0.47 mmol/g) as a resin, the procedure of Example 5 was repeated to yield a TFA salt of the titled compound in the amount of 18.8 mg.

HPLC (method e):RT22.70; FAB-MS: 531(M+H$^+$); NMR (method f,DMSO-d6): δ 1.30(9H,s), 2.78(1H,dd,J=14,9 Hz), 2.90(1H,dd,J=14,8 Hz), 2.94(1H,dd,J=14,5 Hz), 3.04 (1H,dd,J=14,5 Hz), 3.69(3H,s), 4.17(1H,brs), 4.43(1H,ddd, J=14,9,8 Hz), 5.60(1H,d,J=8 Hz), 6.82(1H,d,J=8 Hz), 7.01 (1H,s), 7.06(1H,dd,J=8,1 Hz), 7.15(1H,d,J=1 Hz), 7.17–7.48(11H,m), 8.08(3H,brs), 8.54(1H,d,J=8 Hz), 9.06 (1H,d,J=8 Hz).

Example 10

Phe-Phe-Tyr(3-tBu)-NH$_2$

Substituting Fmoc-Phe-OH for the Fmoc-Phg-OH used in Example 5 and using 213 mg (0.1 mmol) of Rink Amide Resin (0.47 mmol/g) as a resin, the procedure of Example 5 was repeated to yield a TFA salt of the titled compound in the amount of 20.5 g.

HPLC (method e):RT19.41; FAB-MS: 531(M+H$^+$); NMR (method f,DMSO-d6): δ 1.31(9H,s), 2.74(1H,dd,J=14,8 Hz), 2.82(1H,dd,J=14,9 Hz), 2.87(1H,dd,J=14,9 Hz), 2.89 (1H,dd,J=14,5 Hz), 3.03(1H,dd,J=14,4 Hz), 3.10(1H,dd,J=14,4 Hz), 4.00(1H,brs), 4.40(1H,ddd,J=8,8,5 Hz), 4.61(1H, ddd,J=9,8,4 Hz), 6.65(1H,d,J=8 Hz), 6.87(1H,dd,J=8,2 Hz), 7.00–7.10(2H,m), 7.15–7.28(10H,m), 7.30(1H,s), 7.98(3H, brs), 8.23(1H,d,J=8 Hz), 8.66(1H,d,J=8 Hz), 9.07(1H,s).

Example 11

Phe-Val-Tyr(3-tBu)-NH$_2$

Substituting Fmoc-Val-OH for the Fmoc-Phg-OH used in Example 5 and using 213 mg (0.1 mmol) of Rink Amide Resin (0.47 mmol/g) as a resin, the procedure of Example 5 was repeated to yield a TFA salt of the titled compound in the amount of 28.4 mg.

HPLC (method e):RT18.68; FAB-MS: 483(M+H$^+$); NMR (method f,DMSO-d6): δ 0.83(3H,d,J=7 Hz), 0.84(3H,d,J=7 Hz), 1.31(9H,s), 1.96(1H,dqq,J=7,6,6 Hz), 2.71(1H,dd,J=14,9 Hz), 2.86(1H,dd,J=14,6 Hz), 2.88(1H,dd,J=14,8 Hz), 3.03(1H,dd,J=14,5 Hz), 4.13(1H,brs), 4.25(1H,dd,J=9,6 Hz), 4.40(1H,ddd,J=9,8,6 Hz), 6.65(1H,d,J=8 Hz), 6.88(1H, dd,J=8,2 Hz), 6.99(1H,s), 7.05(1H,d,J=2 Hz), 7.13–7.25 (5H,m), 7.35(1H,s), 8.05(1H,d,J=8 Hz), 8.07(3H,brs), 8.43 (1H,d,J=9 Hz), 9.08(1H,s).

Example 12

Phe-Phg-Tyr-NH$_2$

Substituting Fmoc-Tyr(tBu)-OH for the Fmoc-Tyr(3-tBu)-OH used in Example 5 and using 213 mg (0.1 mmol) of Rink Amide Resin (0.47 mmol) as a resin, the procedure of Example 5 was repeated to yield a TFA salt of the titled compound in the amount of 21.7 mg.

HPLC (method e):RT13.40; FAB-MS: 461(M+H$^+$); NMR (method f,DMSO-d6): δ 2.73(1H,dd,J=14,8 Hz), 2.89(1H, dd,J=14,5 Hz), 2.93(1H,dd,J=14,8 Hz), 3.07(1H,dd,J=14,5 Hz), 4.17(1H,dd,J=8,5 Hz), 4.39(1H,ddd,J=8,8,5 Hz), 5.59 (1H,d,J=8 Hz), 6.63(2H,d), 6.99(1H,s), 7.03(2H,d), 7.20–7.50(11H,m), 8.05(3H,brs), 8.45(1H,d,J=8 Hz), 9.06 (1H,d,J=8 Hz), 9.16(1H,s).

Example 13

Phe-Ala-Tyr(3-tBu)-NH$_2$

Substituting Fmoc-Ala-OH.H$_2$O for the Fmoc-D-Hyp-OH used in Example 6(2), the procedure of Example 6(2) was repeated (except that Fmoc-Ala-OH.H$_2$O and Fmoc-Phe-OH were coupled by method 1) to yield a TFA salt of the titled compound in the amount of 27.8 mg.

HPLC (method e):RT17.82; FAB-MS: 455(M+H$^+$); NMR (method f,DMSO-d6): δ 1.22(3H,d,J=6 Hz), 1.31(9H,s), 2.71(1H,dd,J=14,9 Hz), 2.86(1H,dd,J=14,9 Hz), 2.87(1H, dd,J=14,5 Hz), 3.06(1H,dd,J=14,5 Hz), 4.04(1H,brs), 4.30–4.40(2H,m), 6.65(1H,d,J=8 Hz), 6.86(1H,dd,J=8,2 Hz), 7.03(1H,d,J=2 Hz), 7.04(1H,s), 7.17–7.27(5H,m), 7.39 (1H,s), 8.01(1H,d,J=8 Hz), 8.06(3H,brs), 8.58(1H,d,J=8 Hz), 9.08(1H,s).

Example 14

Phe-Leu-Tyr(3-tBu)-NH$_2$

Substituting Fmoc-Leu-OH for the Fmoc-Ala-OH.H$_2$O used in Example 13, the procedure of Example 13 was repeated to yield a TFA salt of the titled compound in the amount of 31.6 mg.

HPLC (method e):RT20.02; FAB-MS: 497(M+H$^+$); NMR (method f,DMSO-d6): δ 0.86(3H,d,J=6 Hz), 0.89(3H,d,J=6 Hz), 1.31(9H,s), 1.43(2H,dd,J=7,7 Hz), 1.61(1H,tqq,J=7,6,6 Hz), 2.73(1H,dd,J=14,8 Hz), 2.81–2.93(2H,m), 3.09(1H,dd, J=14,5 Hz), 4.04(1H,brs), 4.31–4.42(2H,m), 6.64(1H,d,J=8 Hz), 6.85(1H,dd,J=8,2 Hz), 7.02(1H,d,J=2 Hz), 7.03(1H,s), 7.18–7.26(5H,m), 7.37(1H,s), 8.00(1H,d,J=8 Hz), 8.05(3H, brs), 8.56(1H,d,J=8 Hz), 9.08(1H,s).

Example 15

Val-Phg-Tyr(3-tBu)-NH$_2$

Substituting Fmoc-Val-OH for the Fmoc-Phe-OH used in Example 6(2) and also substituting Fmoc-Phg-OH for Fmoc-D-Hyp, the procedure of Example 6(2) was repeated (except that Fmoc-Val-OH and Fmoc-Phg-OH were coupled by method 1) to yield a TFA salt of the titled compound in the amount of 18.2 mg.

HPLC (method e):RT17.64; FAB-MS: 469(M+H$^+$); NMR (method g,DMSO-d6): δ 0.90(3H,d,J=7 Hz), 0.91(3H,d,J=7 Hz), 1.31(9H,s), 2.02(1H,m), 2.72(1H,dd,J=14,9 Hz), 2.87 (1H,dd,J=14,5 Hz), 3.77(1H,m), 4.42(1H,m), 5.61(1H,d,J=8 Hz), 6.60(1H,d,J=8 Hz), 6.80(1H,dd,J=8,2 Hz), 6.99–7.01 (2H,m), 7.25–7.45(6H,m), 8.03(3H,brs), 8.46(1H,d,J=8 Hz), 8.94(1H,d,J=8 Hz), 9.07(1H,s).

Example 16

Leu-Phg-Tyr(3-tBu)-NH$_2$

Substituting Fmoc-Leu-OH for the Fmoc-Phe-OH used in Example 6(2) and also substituting Fmoc-Phg-OH for Fmoc-D-Hyp, the procedure of Example 6(2) was repeated (except that Fmoc-Leu-OH and Fmoc-Phg-OH were coupled by method 1) to yield a TFA salt of the titled compound in the amount of 19.3 mg.

HPLC (method e):RT18.74; FAB-MS: 483(M+H$^+$); NMR (method g,DMSO-d6): δ 0.87(3H,d,J=7 Hz), 0.89(3H,d,J=7 Hz), 1.32(9H,s), 1.50–1.65(3H,m), 2.73(1H,dd,J=14,8 Hz), 2.87(1H,dd,J=14,5 Hz), 3.93(1H,m), 4.41(1H,m), 5.59(1H, d,J=8 Hz), 6.62(1H,d,J=8 Hz), 6.81(1H,dd,J=8,1 Hz), 6.99–7.01(2H,m), 7.28–7.44(6H,m), 8.06(3H,brs), 8.43(1H, d,J=8 Hz), 9.08(1H,s), 9.09(1H,d,J=8 Hz).

Example 17

Phe-Gly-Tyr(3-tBu)-NH$_2$

Substituting Fmoc-Gly-OPfp for the Fmoc-Phg-OH used in Example 5 and using 213 mg (0.1 mmol) of Rink Amide Resin (0.47 mmol/g) as a resin, the procedure of Example 5 was repeated (except that Fmoc-Gly-OPfp was coupled by method 5) to yield a TFA salt of the titled compound in the amount of 20.8 mg.

HPLC (method d):RT17.23; FAB-MS: 441(M+H$^+$); NMR (method f,DMSO-d6): δ 1.32(9H,s), 2.64(1H,dd,J=14,9 Hz), 2.88(1H,dd,J=14,5 Hz), 2.91(1H,dd,J=14,8 Hz), 3.07 (1H,dd,J=14,5 Hz), 3.65(1H,dd,J=17,6 Hz), 3.90(1H,dd,J= 17,6 Hz), 4.07(1H,brs), 4.36(1H,ddd,J=9,8,5 Hz), 6.64(1H, d,J=8 Hz), 6.85(1H,dd,J=8,1 Hz), 7.01(1H,d,J=1 Hz), 7.06 (1H,s), 7.20–7.35(5H,m), 7.45(1H,s), 8.10(3H,brs), 8.19 (1H,d,J=8 Hz), 8.62(1H,dd,J=6,6 Hz), 9.09(1H,s).

Example 18

18A: Phe-N-Me-Phg-Tyr(3-tBu)-NH$_2$

18B: Phe-N-Me-D-Phg-Tyr(3-tBu)-NH$_2$

A reaction vessel was charged with 213 mg (0.1 mmol) of Rink Amide Resin (0.47 mmol/g); after being swelled with DMF, the resin was treated with piperidine to remove Fmoc. Subsequently, Fmoc-Tyr(3-tBu)-OH was coupled by method 1. After filtering and washing with DMF, the resin was treated with piperidine to remove Fmoc. Subsequently, using α-bromophenylacetic acid and 40% aqueous methylamine, coupling was done by method 6 to construct Nα-substituted amino acid residues. After filtering and washing with DMF, Boc-Phe-OH was coupled by method 2. After the end of the reaction, filtering and washing with DMF and DCM were effected, followed by cleavage with 3 ml of 95% aqueous TFA. The reaction mixture was concentrated under reduced pressure and the residue was dissolved in 2 ml of DMF, followed by HPLC purification. The active fractions were collected, concentrated and freeze-dried to yield TFA salts of the titled compounds in respective amounts of 21.9 mg (18A) and 12.9 mg (18B).

18A HPLC (method c):RT16.64; FAB-MS: 531(M+H$^+$); NMR(method g,DMSO-d6): δ 1.27(9H,s), 2.45(3H,s), 2.62–3.11(4H,m), 4.60(2H,m), 6.07(1H,s), 6.41(2H,d,J=7 Hz), 6.56(1H,d,J=8 Hz), 6.71(1H,d,J=8 Hz), 7.05–7.32(11H, m), 8.29(3H,brs), 8.39(1H,d,J=9 Hz), 9.13(1H,s).

18B HPLC (method c):RT14.20; FAB-MS: 531(M+H$^+$); NMR(method f,DMSO-d6): δ 1.28(9H,s), 2.47(3H,s), 2.70 (1H,dd,J=14,9 Hz), 2.87(1H,dd,J=14,5 Hz), 2.96(2H,d,J=7 Hz), 4.42(1H,ddd,J=5,9,8 Hz), 4.49(1H,brs), 6.27(1H,s), 6.62(1H,d,J=8 Hz), 6.92(1H,dd,J=8,2 Hz), 7.00(1H,s), 7.05–7.36(11H,m), 7.45(1H,s), 8.14(3H,brs), 8.32(1H,d,J=8 Hz), 9.04(1H,s).

Example 19

N-benzyl-N-(4-pyridylthioacetyl)-Phg-Tyr(3-tBu)-NH$_2$

A reaction vessel was charged with 213 mg (0.1 mmol) of Rink Amide Resin (0.47 mmol/g); after being swelled with DMF, the resin was treated with piperidine to remove Fmoc. Subsequently, Fmoc-Tyr(3-tBu)-OH was coupled by method 1. After filtering and washing with DMF, the resin was treated with piperidine to remove Fmoc. Subsequently, using α-bromophenylacetic acid and benzylamine, coupling was done by method 6 to construct Nα-substituted amino acid residues. After filtering and washing with DMF, a mixture of 1.5 ml of DMF, 1.5 ml of NMM and 34 mg (0.2 mmol) of 4-pyridylthioacetic acid, and 114 mg (0.3 mmol) of HATU were added, followed by shaking for 2 hours to effect coupling. After the end of the reaction, filtering, and washing with DMF, DCM and methanol were effected and the resin was dried. Cleavage was performed with 3 ml of 95% aqueous TFA. The reaction mixture was concentrated under reduced pressure and the residue was dissolved in 2 ml of DMF, followed by HPLC purification. The active fractions were collected, concentrated and freeze-dried to yield a TFA salt of the titled compound in the amount of 19.8 mg as a mixture of diastereomers.

HPLC (method b):RT22.90,23.39; FAB-MS: 611(M+H$^+$);

Example 20

Phe-Phg-Tyr(3-tBu)-OH

Using 274 mg (0.2 mmol) of Wang Resin (0.73 mmol/g) as a resin, the procedure of Example 5 was repeated (except that Fmoc-Tyr(3-tBu)-OH was coupled by method 4) to yield a TFA salt of the titled compound in 31.2 mg.

HPLC (method b):RT20.62; FAB-MS: 518(M+H$^+$); NMR (method f,DMSO-d6): δ 1.31(9H,s), 2.82(1H,dd,J=14,8 Hz), 2.89(1H,dd,J=14,8 Hz), 2.94(1H,dd,J=14,5 Hz), 3.04 (1H,dd,J=14,5 Hz), 4.10(1H,brs), 4.35(1H,ddd,J=8,8,5 Hz), 5.61(1H,d,J=8 Hz), 6.66(1H,d,J=8Hz), 6.84(1H,dd,J=8,1 Hz), 7.04(1H,d,J=1Hz), 7.15–7.45(10H,m), ca7.9 (ambiguous,br), 8.68(1H,d,J=8 Hz), 9.02(1H,d,J=8 Hz), 9.14(1H,s).

Example 21

Phe-Tyr-Tyr(3-tBu)-NH$_2$

Substituting Fmoc-Tyr(tBu)-OH for the Fmoc-Phg-OH used in Example 5 and using 107 mg (0.05 mmol) of Rink Amide Resin (0.47 mmol/g) as a resin, the procedure of Example 5 was repeated (except that after cleavage, the reaction mixture was concentrated under reduced pressure and the residue was dissolved in 3 ml of methanol, followed by another concentrating under reduced pressure) to yield a TFA salt of the titled compound in the amount of 15.8 mg.

HPLC (method e):RT18.78; FAB-MS: 547(M+H$^+$);

Example 22

Phe-Hph-Tyr(3-tBu)-NH$_2$

Substituting Fmoc-Hph-OH for the Fmoc-Tyr(tBu)-OH used in Example 21, the procedure of Example 21 was repeated to yield a TFA salt of the titled compound in the amount of 19.4 mg.

HPLC (method e):RT21.53; FAB-MS: 545(M+H$^+$);

Example 23

Phe-Thi-Tyr(3-tBu)-NH$_2$

Substituting Fmoc-Thi-OH for the Fmoc-Tyr(tBu)-OH used in Example 21, the procedure of Example 21 was repeated to yield a TFA salt of the titled compound in 21.5 mg.

HPLC (method e):RT19.65; FAB-MS: 537(M+H$^+$);

Example 24

Phe-β-Ala-Tyr(3-tBu)-NH$_2$

Substituting Fmoc-β-Ala-OH for the Fmoc-Tyr(tBu)-OH used in Example 21, the procedure of Example 21 was repeated to yield a TFA salt of the titled compound in the amount of 29.4 mg.

HPLC (method e):RT17.51; FAB-MS: 455(M+H$^+$);

Example 25

Phe-γ-Abu-Tyr(3-tBu)-NH$_2$

Substituting Fmoc-γ-Abu-OH for the Fmoc-Tyr(tBu)-OH used in Example 21, the procedure of Example 21 was repeated to yield a TFA salt of the titled compound in the amount of 34.4 mg.

HPLC (method e):RT17.59; FAB-MS: 469(M+H$^+$);

Example 26

Phe-Aib-Tyr(3-tBu)-NH$_2$

Substituting Fmoc-Aib-OH for the Fmoc-Tyr(tBu)-OH used in Example 21, the procedure of Example 21 was repeated to yield a TFA salt of the titled compound in the amount of 27.2 mg.

HPLC (method e):RT19.82; FAB-MS: 469(M+H$^+$);

Example 27

Phe-Ile-Tyr(3-tBu)-NH$_2$

Substituting Fmoc-Ile-OPfp for the Fmoc-Tyr(tBu)-OH used in Example 21, the procedure of Example 21 was repeated (except that Fmoc-Ile-OPfp was coupled by method 5) to yield a TFA salt of the titled compound in 18.9 mg.

HPLC (method e):RT19.35; FAB-MS: 497(M+H$^+$);

Example 28

Phe-Chg-Tyr(3-tBu)-NH$_2$

Substituting Fmoc-Chg-OH for the Fmoc-Tyr(tBu)-OH used in Example 21, the procedure of Example 21 was repeated. The crude product was dissolved in DMSO and purified by HPLC; the active fractions were collected, concentrated and freeze-dried to yield a TFA salt of the titled compound in the amount of 10.1 mg.

HPLC (method e):RT20.54; FAB-MS: 523(M+H$^+$); NMR (method g,DMSO-d6): δ 0.82–1.20(5H,m), 1.31(9H,s), 1.46–1.73(6H,m), 2.70(1H,dd,J=14,9 Hz), 2.82–2.90(2H, m), 3.02(1H,dd, J=14,5 Hz), 4.10(1H,brs), 4.24(1H,t,J=8 Hz), 4.42(1H,dd,J=13,5 Hz), 6.64(1H,d,J=8 Hz), 6.86(1H, dd,J=8,1 Hz), 7.00(1H,s), 7.04(1H,d,J=1Hz), 7.18(5H,s), 7.34(1H,s), 8.01–8.04(4H,m), 8.42(1H,d,J=9 Hz), 9.07(1H, s).

Example 29

Phe-Cha-Tyr(3-tBu)-NH$_2$

Substituting Fmoc-Cha-OH for the Fmoc-Chg-OH used in Example 28, the procedure of Example 28 was repeated to yield a TFA salt of the titled compound in the amount of 10.0 mg.

HPLC (method e):RT22.35; FAB-MS: 537(M+H$^+$); NMR (method g,DMSO-d6): δ 0.81–1.25(5H,m), 1.31(9H,s), 1.40–1.77(8H,m), 2.68–2.89(3H,m), 3.09(1H,dd,J=14,4 Hz), 4.02(1H,brs), 4.33–4.38(2H,m), 6.63(1H,d,J=8 Hz), 6.85(1H,dd,J=8,1 Hz), 7.01–7.04(2H,m), 7.23(5H,s), 7.35 (1H,s), 7.98(1H,d,J=8 Hz), 8.03(3H,brs), 8.55(1H,d,J=8 Hz), 9.07(1H,s).

Example 30

Phe-Tle-Tyr(3-tBu)-NH$_2$

Substituting Fmoc-Tle-OH for the Fmoc-Tyr(tBu)-OH used in Example 21, the procedure of Example 21 was repeated to yield a TFA salt of the titled compound in the amount of 23.8 mg.

HPLC (method e):RT18.87; FAB-MS: 497(M+H$^+$);

Example 31

Phe-Asp-Tyr(3-tBu)-NH$_2$

Substituting Fmoc-Asp(OtBu)-OH for the Fmoc-Tyr (tBu)-OH used in Example 21 and using MeCN instead of methanol to dissolve the residue, the procedure of Example 21 was repeated to yield a TFA salt of the titled compound in the amount of 30.2 mg.

HPLC (method e):RT17.13; FAB-MS: 499(M+H$^+$);

Example 32

Phe-Glu-Tyr(3-tBu)-NH$_2$

Substituting Fmoc-Glu(OtBu)-OH for the Fmoc-Tyr (tBu)-OH used in Example 21 and using MeCN instead of methanol as a solvent to dissolve the residue, the procedure of Example 21 was repeated to yield a TFA salt of the titled compound in the amount of 28.2 mg.

HPLC (method e):RT17.37; FAB-MS: 513 (M+H$^+$);

Example 33

Phe-Aad-Tyr(3-tBu)-NH$_2$

Substituting Fmoc-Aad(OtBu)-OH for the Fmoc-Tyr (tBu)-OH used in Example 21 and using MeCN instead of methanol as a solvent to dissolve the residue, the procedure of Example 21 was repeated to yield a TFA salt of the titled compound in the amount of 31.8 mg.

HPLC (method e):RT17.54; FAB-MS: 527 (M+H$^+$);

Example 34

Phe-Asn-Tyr(3-tBu)-NH$_2$

Substituting Fmoc-Asn-OH for the Fmoc-Tyr(tBu)-OH used in Example 21, the procedure of Example 21 was repeated to yield a TFA salt of the titled compound in the amount of 21.5 mg.

HPLC (method e):RT17.04; FAB-MS: 498(M+H$^+$);

Example 35

Phe-Gln-Tyr(3-tBu)-NH$_2$

Substituting Fmoc-Gln-OPfp for the Fmoc-Tyr(tBu)-OH used in Example 21), the procedure of Example 21 was repeated (except that Fmoc-Gln-OPfp was coupled by method 5) to yield a TFA salt of the titled compound in the amount of 27.2 mg.

HPLC (method e):RT16.90; FAB-MS: 512(M+H$^+$);

Example 36

Phe-Cit-Tyr(3-tBu)-NH$_2$

Substituting Fmoc-Cit-OH for the Fmoc-Tyr(tBu)-OH used in Example 21, the procedure of Example 21 was repeated to yield a TFA salt of the titled compound in 25.6 mg.

HPLC (method e):RT16.68; FAB-MS: 541(M+H$^+$);

Example 37

Phe-Dab-Tyr(3-tBu)-NH$_2$

Substituting Fmoc-Dab(Boc)-OH for the Fmoc-Tyr(tBu)-OH used in Example 21, the procedure of Example 21 was repeated to yield a TFA salt of the titled compound in the amount of 29.1 mg.

HPLC (method e):RT16.07; FAB-MS: 484(M+H$^+$);

Example 38

Phe-Orn-Tyr(3-tBu)-NH$_2$

Substituting Fmoc-Orn(Boc)-OH for the Fmoc-Tyr(tBu)-OH used in Example 21), the procedure of Example 21 was repeated to yield a TFA salt of the titled compound in the amount of 33.7 mg.

HPLC (method e):RT16.04; FAB-MS: 498(M+H$^+$);

Example 39

Phe-Lys-Tyr(3-tBu)-NH$_2$

Substituting Fmoc-Lys(Boc)-OH for the Fmoc-Tyr(tBu)-OH used in Example 21), the procedure of Example 21 was repeated to yield a TFA salt of the titled compound in the amount of 29.2 mg.

HPLC (method e):RT16.49; FAB-MS: 512(M+H$^+$);

Example 40

Phe-Ser-Tyr(3-tBu)-NH$_2$

Substituting Fmoc-Ser(tBu)-OH for the Fmoc-Tyr(tBu)-OH used in Example 21, the procedure of Example 21 was repeated to yield a TFA salt of the titled compound in the amount of 25.5 mg.

HPLC (method e):RT17.31; FAB-MS: 471(M+H$^+$);

Example 41

Phe-Hse-Tyr(3-tBu)-NH$_2$

Substituting Fmoc-Hse(Trt)-OH for the Fmoc-Tyr(tBu)-OH used in Example 21, the procedure of Example 21 was repeated. After concentrating the cleavage cocktail, re-precipitation was effected with diethyl ether to yield a TFA salt of the titled compound in the amount of 7.8 mg.

HPLC (method e):RT17.64; FAB-MS: 485(M+H$^+$);

Example 42

Phe-Thr-Tyr(3-tBu)-NH$_2$

Substituting Fmoc-Thr(tBu)-OH for the Fmoc-Tyr(tBu)-OH used in Example 21, the procedure of Example 21 was repeated to yield a TFA salt of the titled compound in the amount of 24.1 mg.

HPLC (method e):RT17.40; FAB-MS: 485(M+H$^+$);

Example 43

Phe-Abu-Tyr(3-tBu)-NH$_2$

Substituting Fmoc-Abu-OH for the Fmoc-Tyr(tBu)-OH used in Example 21, the procedure of Example 21 was repeated to yield a TFA salt of the titled compound in the amount of 19.6 mg.

HPLC (method e):RT18.55; FAB-MS: 469(M+H$^+$);

Example 44

Phe-Nva-Tyr(3-tBu)-NH$_2$

Substituting Fmoc-Nva-OH for the Fmoc-Tyr(tBu)-OH used in Example 21, the procedure of Example 21 was repeated to yield a TFA salt of the titled compound in the amount of 19.8 mg.

HPLC (method e):RT18.82; FAB-MS: 483(M+H$^+$);

Example 45

Phe-Met-Tyr(3-tBu)-NH$_2$

Substituting Fmoc-Met-OH for the Fmoc-Tyr(tBu)-OH used in Example 21, the procedure of Example 21 was repeated to yield a TFA salt of the titled compound in the amount of 24.3 mg.

HPLC (method e):RT18.79; FAB-MS: 515(M+H$^+$);

Example 46

Phe-His-Tyr(3-tBu)-NH$_2$

Substituting Fmoc-His(Boc)-OH for the Fmoc-Tyr(tBu)-OH used in Example 21, the procedure of Example 21 was repeated to yield a TFA salt of the titled compound in the amount of 26.7 mg.

HPLC (method e):RT16.78; FAB-MS: 521(M+H$^+$);

Example 47

Phe-Trp-Tyr(3-tBu)-NH$_2$

Substituting Fmoc-Trp(Boc)-OH for the Fmoc-Tyr(tBu)-OH used in Example 21, the procedure of Example 21 was repeated to yield a TFA salt of the titled compound in the amount of 14.5 mg.

HPLC (method e):RT20.76; FAB-MS: 570(M+H$^+$);

Example 48

Phe-Tiq-Tyr(3-tBu)-NH$_2$

Substituting Fmoc-Tiq-OH for the Fmoc-Tyr(tBu)-OH used in Example 21, the procedure of Example 21 was repeated to yield a TFA salt of the titled compound in the amount of 23.7 mg.

HPLC (method e):RT21.87; FAB-MS: 543 (M+H$^+$);

Example 49

N-(4-pyridylthioacetyl)-Phg-Tyr(3-tBu)-NH$_2$

A reaction vessel was charged with 91 mg (0.05 mmol) of Fmoc-2,4-dimethoxy-4'-(carboxymethyloxy)-benzhydrylamine linked to Aminomethyl Resin (0.55 mmol/g); after being swelled with DMF, the resin was treated with piperidine to remove Fmoc. Subsequently, Fmoc-Tyr(3-tBu)-OH was coupled by method 1. After filtering and washing with DMF, the resin was treated with piperidine to remove Fmoc. Subsequently, Fmoc-Phg-OH was coupled by method 3. After filtering and washing with DMF, the resin was treated again with piperidine to remove Fmoc. Subsequently, a mixture of 1.5 ml of DMF, 0.5 ml of NMM and 17 mg (0.1 mmol) of 4-pyridylthioacetic acid, as well as 23 mg (0.15 mmol) of HOBT and 25 ml (0.16 mmol) of DIC were added, followed by shaking for 2 hours to effect coupling. After the end of the reaction, filtering and washing with DMF, DCM and methanol were performed and the resin was subsequently dried. Cleavage was also performed with 2 ml of 95% aqueous TFA. The reaction mixture was concentrated under reduced pressure and the residue was dissolved in 3 ml of methanol, followed by reconcentrating under reduced pressure to yield a TFA salt of the titled compound in the amount of 27.8 mg.

HPLC (method a):RT17.55; FAB-MS: 521(M+H$^+$);

Example 50

N-(1-benzocyclobutanecarbonyl)-Phg-Tyr(3-tBu)-NH$_2$

Substituting 1-benzocyclobutanecarboxylic acid for the 4-pyridylthioacetic acid used in Example 49, the procedure of Example 49 was repeated (except that 1-benzocyclobutanecarboxylic acid was coupled by method 3) to yield the titled compound in the amount of 23.8 mg as a mixture of diastereomers.

HPLC (method a):RT23.43,23.68; FAB-MS: 500(M+H$^+$);

Example 51

N-(2-indolecarbonyl)-Phg-Tyr(3-tBu)-NH$_2$

Substituting 2-indolecarboxylic acid for the 1-benzocyclobutanecarboxylic aid used in Example 50, the procedure of Example 50 was repeated to yield the titled compound in the amount of 8.0 mg.

HPLC (method a):RT24.64; FAB-MS: 513(M+H$^+$);

Example 52

Tyr-Phg-Tyr(3-tBu)-NH$_2$

A reaction vessel was charged with 91 mg (0.05 mmol) of Fmoc-2,4-dimethoxy-4'-(carboxymethyloxy)-benzhydrylamine linked to Aminomethyl Resin (0.55 mmol/g); after being swelled with DMF, the resin was treated with piperidine to remove Fmoc. Subsequently, Fmoc-Tyr(3-tBu)-OH was coupled by method 1. After filtering and washing with DMF, the resin was treated with piperidine to remove Fmoc. Subsequently, Fmoc-Phg-OH was coupled by method 3. After filtering and washing with DMF, the resin was treated with piperidine to remove Fmoc. Subsequently, Fmoc-Tyr(tBu)-OH was coupled by method 3. After filtering and washing with DMF, the resin was treated again with piperidine to remove Fmoc. After the end of the reaction, washing was effected with DCM and methanol and the resin was subsequently dried. Cleavage was performed with 2 ml of 95% aqueous TFA. The reaction mixture was concentrated under reduced pressure and the residue was dissolved in 3 ml of methanol, followed by reconcentrating under reduced pressure to yield a TFA salt of the titled compound in the amount of 26.2 mg.

HPLC (method a):RT17.43; FAB-MS: 533(M+H$^+$);

Example 53

Phg-Phg-Tyr(3-tBu)-NH$_2$

Substituting Fmoc-Phg-OH for the Fmoc-Tyr(tBu)-OH used in Example 52, the procedure of Example 52 was repeated to yield a TFA salt of the titled compound in the amount of 23.2 mg.

HPLC (method a):RT18.42; FAB-MS: 503(M+H$^+$);

Example 54

Thi-Phg-Tyr(3-tBu)-NH$_2$

Substituting Fmoc-Thi-OH for the Fmoc-Tyr(tBu)-OH used in Example 52, the procedure of Example 52 was repeated to yield a TFA salt of the titled compound in 27.4 mg.

HPLC (method a):RT18.43; FAB-MS: 523(M+H$^+$);

Example 55

Trp-Phg-Tyr(3-tBu)-NH$_2$

Substituting Fmoc-Trp(Boc)-OH for the Fmoc-Tyr(tBu)-OH used in Example 52, the procedure of Example 52 was repeated to yield a TFA salt of the titled compound in the amount of 20.9 mg.

HPLC (method a):RT19.84; FAB-MS: 556(M+H$^+$);

Example 56

His-Phg-Tyr(3-tBu)-NH$_2$

Substituting Fmoc-His(Boc)-OH for the Fmoc-Tyr(tBu)-OH used in Example 52, the procedure of Example 52 was repeated to yield a TFA salt of the titled compound in the amount of 14.4 mg.

HPLC (method a):RT15.12; FAB-MS: 507(M+H$^+$);

Example 57

N-((±)-3-phenylbutyryl)-Phg-Tyr(3-tBu)-NH$_2$

Substituting (±)-3-phenylbutyric acid for the 1-benzocyclobutanecarboxylic acid used in Example 50 and using 107 mg (0.05 mmol) of Rink Amide Resin (0.47 mmol/g) as a resin, the procedure of Example 50 was repeated (except that Fmoc-Phg-OH was coupled by method 1 and 3-phenylbutyric acid by method 2) to yield the titled compound in the amount of 18.1 mg.

HPLC (method a):RT25.19; FAB-MS: 516(M+H$^+$);

Example 58

N-(2-biphenylcarbonyl)-Phg-Tyr(3-tBu)-NH$_2$

Substituting 2-biphenylcarboxylic acid for the 3-phenylbutyric acid used in Example 57, the procedure of Example 57 was repeated to yield the titled compound in the amount of 15.1 mg.

HPLC (method a):RT26.23; FAB-MS: 550(M+H$^+$);

Example 59

β-Ala-Phg-Tyr(3-tBu)-NH$_2$

A reaction vessel was charged with 45 mg (0.025 mmol) of Fmoc-2,4-dimethoxy-4'-(carboxymethyloxy)-benzhydrylamine linked to Aminomethyl Resin (0.55 mmol/g); after being swelled with DMF, the resin was treated with piperidine to remove Fmoc. Subsequently, Fmoc-Tyr(3-tBu)-OH was coupled by method 1. After filtering and washing with DMF, the resin was treated with piperidine to remove Fmoc. Subsequently, Fmoc-Phg-OH was coupled by method 3. After washing with DMF, DCM and methanol, the resin was dried.

The dried resin was transferred into a reaction vessel of model ACT-496 MOS (product of Advanced ChemTech). After being swelled with DMF, the resin was treated with piperidine to remove Fmoc. Subsequently, 0.5 ml of a mixture of Fmoc-β-Ala-OH, HOBT and DMF (Fmoc-β-Ala-OH in 0.050 mmol and HOBT in 0.075 mmol), as well as 0.25 ml of DIC/DMF (DIC in 0.080 mmol) were added, followed by shaking for 2 hours. After filtering and washing with DMF, the resin was treated again with piperidine to remove Fmoc. After the end of the reaction, washing was effected with DCM and cleavage was performed with 1 ml of 95% aqueous TFA. After recovering the reaction mixture by filtration, another 1 ml of 95% aqueous TFA was added, followed by shaking for 30 minutes. The filtrates were combined and concentrated under reduced pressure, and the residue was dissolved in 3 ml of methanol, which was concentrated again to yield a TFA salt of the titled compound in the amount of 13.4 mg.

HPLC (method e):RT16.72; FAB-MS: 441(M+H$^+$);

Example 60

Aib-Phg-Tyr(3-tBu)-NH$_2$

Substituting Fmoc-Aib-OH for the Fmoc-β-Ala-OH used in Example 59, the procedure of Example 59 was repeated to yield a TFA salt of the titled compound in the amount of 15.3 mg.

HPLC (method e):RT17.12; FAB-MS: 455(M+H$^+$);

Example 61

Ile-Phg-Tyr(3-tBu)-NH$_2$

Substituting Fmoc-Ile-OH for the Fmoc-β-Ala-OH used in Example 59, the procedure of Example 59 was repeated to yield a TFA salt of the titled compound in the amount of 15.4 mg.

HPLC (method e):RT18.25; FAB-MS: 483(M+H$^+$);

Example 62

Chg-Phg-Tyr(3-tBu)-NH$_2$

Substituting Fmoc-Chg-OH for the Fmoc-β-Ala-OH used in Example 59, the procedure of Example 59 was repeated to yield a TFA salt of the titled compound in the amount of 12.2 mg.

HPLC (method e):RT19.61; FAB-MS: 509(M+H$^+$);

Example 63

Cha-Phg-Tyr(3-tBu)-NH$_2$

Substituting Fmoc-Cha-OH for the Fmoc-β-Ala-OH used in Example 59, the procedure of Example 59 was repeated to yield a TFA salt of the titled compound in the amount of 16.7 mg.

HPLC (method e):RT21.34; FAB-MS: 523(M+H$^+$);

Example 64

Tle-Phg-Tyr(3-tBu)-NH$_2$

Substituting Fmoc-Tle-OH for the Fmoc-β-Ala-OH used in Example 59, the procedure of Example 59 was repeated to yield a TFA salt of the titled compound in the amount of 14.9 mg.

HPLC (method e):RT18.02; FAB-MS: 483(M+H$^+$);

Example 65

Asp-Phg-Tyr(3-tBu)-NH$_2$

Substituting Fmoc-Asp(OtBu)-OPfp for the Fmoc-β-Ala-OH used in Example 59, the procedure of Example 59 was repeated (except that 0.25 ml of DIC/DMF was not added in coupling of Fmoc-Asp(OtBu)-OPfp) to yield a TFA salt of the titled compound in the amount of 18.1 mg.

HPLC (method e):RT16.42; FAB-MS: 485(M+H$^+$);

Example 66

Aad-Phg-Tyr(3-tBu)-NH$_2$

Substituting Fmoc-Aad(OtBu)-OH for the Fmoc-β-Ala-OH used in Example 59, the procedure of Example 59 was repeated to yield a TFA salt of the titled compound in the amount of 16.8 mg.

HPLC (method e):RT16.79; FAB-MS: 513(M+H$^+$);

Example 67

Asn-Phg-Tyr (3-tBu)-NH$_2$

Substituting Fmoc-Asn-OH for the Fmoc-β-Ala-OH used in Example 59, the procedure of Example 59 was repeated to yield 17.2 mg of the titled compound.

HPLC (method e):RT16.17; FAB-MS: 484(M+H$^+$);

Example 68

Gln-Phg-Tyr(3-tBu)-NH$_2$

Substituting Fmoc-Gln-OPfp for the emoc-Asp(OtBu)-OPfp used in Example 65, the procedure of Example 65 was repeated to yield a TFA salt of the titled compound in the amount of 15.9 mg.

HPLC (method e):RT16.39; FAB-MS: 498(M+H$^+$);

Example 69

Cit-Phg-Tyr(3-tBu)-NH$_2$

Substituting Fmoc-Cit-OH for the Fmoc-β-Ala-OH used in Example 59, the procedure of Example 59 was repeated to yield to yield a TFA salt of the titled compound in the amount of 15.3 mg.

HPLC (method e):RT16.36; FAB-MS: 527(M+H⁺);

Example 70

Dab-Phg-Tyr(3-tBu)-NH$_2$

Substituting Fmoc-Dab(Boc)-OH for the Fmoc-β-Ala-OH used in Example 59, the procedure of Example 59 was repeated to yield a TFA salt of the titled compound in the amount of 15.3 mg.

HPLC (method e):RT15.28; FAB-MS: 470(M+H⁺);

Example 71

Lys-Phg-Tyr(3-tBu)-NH$_2$

Substituting Fmoc-Lys(Boc)-OH for the Fmoc-β-Ala-OH used in Example 59, the procedure of Example 59 was repeated to yield a TFA salt of the titled compound in the amount of 16.8 mg.

HPLC (method e):RT15.21; FAB-MS: 498(M+H⁺);

Example 72

Ser-Phg-Tyr(3-tBu)-NH$_2$

Substituting Fmoc-Ser(tBu)-OH for the Fmoc-β-Ala-OH used in Example 59, the procedure of Example 59 was repeated to yield a TFA salt of the titled compound in the amount of 15.4 mg.

HPLC (method e):RT16.30; FAB-MS: 457(M+H⁺);

Example 73

Hse-Phg-Tyr(3-tBu)-NH$_2$

Substituting Fmoc-Hse(Trt)-OH for the Fmoc-β-Ala-OH used in Example 59, the procedure of Example 59 was repeated to yield a TFA salt of the titled compound in the amount of 24.9 mg.

HPLC (method e):RT16.50; FAB-MS: 471(M+H⁺);

Example 74

Thr-Phg-Tyr(3-tBu)-NH$_2$

Substituting Fmoc-Thr(tBu)-OH for the Fmoc-β-Ala-OH used in Example 59, the procedure of Example 59 was repeated to yield a TFA salt of the titled compound in the amount of 15.5 mg.

HPLC (method e):RT16.41; FAB-MS: 471(M+H⁺);

Example 75

Abu-Phg-Tyr(3-tBu)-NH$_2$

Substituting Fmoc-Abu-OH for the Fmoc-β-Ala-OH used in Example 59, the procedure of Example 59 was repeated to yield a TFA salt of the titled compound in the amount of 13.6 mg.

HPLC (method e):RT16.90; FAB-MS: 455(M+H⁺);

Example 76

Nva-Phg-Tyr(3-tBu)-NH$_2$

Substituting Fmoc-Nva-OH for the Fmoc-β-Ala-OH used in Example 59, the procedure of Example 59 was repeated to yield a TFA salt of the titled compound in the amount of 13.9 mg.

HPLC (method e):RT17.79; FAB-MS: 469(M+H⁺);

Example 77

Met-Phg-Tyr(3-tBu)-NH$_2$

Substituting Fmoc-Met-OH for the Fmoc-β-Ala-OH used in Example 59, the procedure of Example 59 was repeated to yield a TFA salt of the titled compound in the amount of 11.6 mg.

HPLC (method e):RT18.09; FAB-MS: 501(M+H⁺);

Example 78

Pro-Phg-Tyr(3-tBu)-NH$_2$

Substituting Fmoc-Pro-OH-AcOEt for the Fmoc-β-Ala-OH used in Example 59, the procedure of Example 59 was repeated to yield a TFA salt of the titled compound in the amount of 14.8 mg.

HPLC (method e):RT17.02; FAB-MS: 467(M+H⁺);

Example 79

Hyp-Phg-Tyr(3-tBu)-NH$_2$

Substituting Fmoc-Hyp-OH for the Fmoc-β-Ala-OH used in Example 59, the procedure of Example 59 was repeated to yield a TFA salt of the titled compound in the amount of 11.2 mg.

HPLC (method e):RT16.54; FAB-MS: 483(M+H⁺);

Example 80

Tic-Phg-Tyr(3-tBu)-NH$_2$

Substituting Fmoc-Tic-OH for the Fmoc-β-Ala-OH used in Example 59, the procedure of Example 59 was repeated to yield a TFA salt of the titled compound in the amount of 16.1 mg.

HPLC (method e):RT19.56; FAB-MS: 529(M+H⁺);

Example 81

Tiq-Phg-Tyr(3-tBu)-NH$_2$

Substituting Fmoc-Tiq-OH for the Fmoc-β-Ala-OH used in Example 59, the procedure of Example 59 was repeated to yield a TFA salt of the titled compound in the amount of 14.7 mg.

HPLC (method e):RT19.33; EAB-MS: 529(M+H⁺);

Example 82

2-Abz-Phg-Tyr(3-tBu)-NH$_2$

Substituting Fmoc-2-Abz-OH for the Fmoc-β-Ala-OH used in Example 59, the procedure of Example 59 was repeated to yield a TFA salt of the titled compound in the amount of 15.2 mg.

HPLC (method e):RT21.38; FAB-MS: 489(M+H⁺);

Example 83

Hph-Phg-Tyr(3-tBu)-NH$_2$

Substituting Fmoc-Hph-OH for the Fmoc-β-Ala-OH used in Example 59, the procedure of Example 59 was repeated to yield a TFA salt of the titled compound in the amount of 16.0 mg.

HPLC (method e):RT20.72; FAB-MS: 531(M+H⁺);

Example 84

N-(α-methylhydrocinnamoyl)-Phg-Tyr(3-tBu)-NH$_2$

Substituting α-methylhydrocinnamic acid for the Fmoc-β-Ala-OH used in Example 59, the procedure of Example 59 was repeated (except that prior to cleavage, no treatment for removing Fmoc was performed since this was unnecessary) to yield 15.2 mg of the titled compound.

HPLC (method e):RT25.22; FAB-MS: 516(M+H⁺);

Example 85

N-(α-methylcinnamoyl)-Phg-Tyr(3-tBu)-NH$_2$

Substituting α-methylcinnamic acid for the α-methylhydrocinnamic acid used in Example 84, the procedure of Example 84 was repeated to yield 16.4 mg of the titled compound.

HPLC (method e):RT26.18; FAB-MS: 514(M+H⁺);

Example 86

N-(3-quinolinecarbonyl)-Phg-Tyr(3-tBu)-NH$_2$

Substituting 3-quinolinecarboxylic acid for the α-methylhydrocinnamic acid used in Example 84, the procedure of Example 84 was repeated to yield 16.9 mg of the titled compound.

HPLC (method e):RT20.73; FAB-MS: 525(M+H⁺);

Example 87

N-(3-furanacryloyl)-Phg-Tyr(3-tBu)-NH$_2$

Substituting 3-furanacrylic acid for the α-methylhydrocinnamic acid used in Example 84, the procedure of Example 84 was repeated to yield 8.2 mg of the titled compound.

HPLC (method e):RT23.08; FAB-MS: 490(M+H⁺);

Example 88

Phe-D-Phg-Tyr(3-tBu)-NH$_2$

Substituting Fmoc-D-Phg-OH for the Fmoc-Phg-OH used in Example 5 and using 182 mg (0.1 mmol) of Fmoc-2,4-dimethoxy-4'-(carboxymethyloxy)-benzhydrylamine linked to Aminomethyl Resin (0.55 mmol/g), the procedure of Example 5 was repeated (except that Fmoc-D-Phg-OH and Boc-Phe-OH were coupled by method 3) to yield a TFA salt of the titled compound in the amount of 15.4 mg.

HPLC (method a):RT20.96; FAB-MS: 517(M+H⁺); NMR (method g,DMSO-d6): δ 1.27(9H,s), 2.57–3.06(4H,m), 4.28–4.35(2H,m), 5.63(1H,d,J=8 Hz), 6.53(1H,d,J=8 Hz), 6.70(1H,d,J=8 Hz), 6.79(2H,d,J=7 Hz), 7.00–7.29(11H,m), 7.51(1H,s), 8.20(3H,brs), 8.71(1H,d,J=8 Hz), 9.07(1H,s), 9.13 (1H,d,J=8 Hz).

Example 89

Phe-N-Me-Val-Tyr(3-tBu)-NH$_2$ (1) Synthesis of Z-Tyr(3-tBu)-NH$_2$

To a solution of 15.3 mg (39.8 mmol) of Z-Tyr(3-tBu)-OMe in 100 ml of 1,4-dioxane, 100 ml of 2 N aqueous sodium hydroxide was added and the mixture was stirred at room temperature for 2 hours and a half. The reaction mixture was rendered acidic by addition of 2 N hydrochloric acid, extracted with ethyl acetate, washed first with water, then with saturated brine. The organic layer was dried with anhydrous sodium sulfate and the solvent was distilled off under reduced pressure; the resulting residue was dissolved in 100 ml of DMF, followed by addition of NMM and ethyl chloroformate in respective amounts of 4.77 ml (43.4 mmol) and 4.15 ml (43.4 mmol) at −15° C. The reaction mixture was stirred with bubbling of ammonia gas for one hour and a half, and then left to stand at room temperature, diluted with ethyl acetate, washed first with water, then with saturated brine. The organic layer was dried with anhydrous sodium sulfate and concentrated under reduced pressure; the resulting residue was subjected to silica gel column chromatography (eluting solvent; methylene chloride:methanol=100:1) to give Z-Tyr(3-tBu)-NH$_2$ in the amount of 10.9 g (74%).

(2) Synthesis of Tyr(3-tBu)-NH$_2$

To a solution of 9.89 g (26.7 mmol) of Z-Tyr(3-tBu)-NH$_2$ in 350 ml of methanol, 3.5 g of 10% palladium carbon was added and the mixture was stirred in a hydrogen atmosphere at room temperature for 10 hours. After filtering, the filtrate was concentrated under reduced pressure and the resulting residue was subjected to silica gel column chromatography (eluting solvent; methylene chloride:methanol=20:1) to yield Tyr(3-tBu)-NH$_2$ in the amount of 5.11 g (81%). NMR(method g,CDCl$_3$): δ 1.40(9H,s), 2.64(1H,dd,J=9.6, 13.9 Hz), 3.18(1H,dd,J=4.0,13.9 Hz), 3.49(1H,s), 3.58(1H, dd,J=4.0,9.6 Hz), 5.45(1H,brs), 6.65(1H,d,J=7.9 Hz), 6.92 (1H,dd,J=2.0,12.0 Hz), 7.10(1H,d,J=2.0 Hz), 6.94(1H,d,6.6 Hz), 7.2–7.4(8H,m), 7.7–7.9(2H,m), 8.46(1H,d,7.6 Hz), 9.06(1H,d).

(3) Synthesis of Z-N-Me-Val-Tyr(3-tBu)-NH$_2$

To a solution of 400 mg (1.52 mmol) of Z-N-Me-Val-OH, 300 mg (1.27 mmol) of Tyr(3-tBu)-NH$_2$ and 230 mg (1.52 mmol) of HOBT in 7 ml of DMF, 0.24 ml (1.52 mmol) of DIC was added dropwise under cooling with ice and the mixture was stirred at room temperature for 15 hours and a half. The reaction mixture was diluted with ethyl acetate and washed with saturated brine. The organic layer was dried with anhydrous sodium sulfate and concentrated under reduced pressure; the resulting residue was subjected to silica gel column chromatography (eluting solvent consisting of methylene chloride, methanol and aqueous ammonia at a ratio of 100:3:1) to give 810 mg of Z-N-Me-Val-Tyr(3-tBu)-NH$_2$.

(4) Synthesis of Boc-Phe-N-Me-Val-Tyr(3-tBu)-NH$_2$

A mixture of 810 mg of Z-N-Me-Val-Tyr(3-tBu)-NH$_2$ and 300 mg of 10% palladium carbon in 50 ml of methanol was stirred under a hydrogen stream for 13 hours and a half. The reaction mixture was filtered and the filtrate was distilled off under reduced pressure. To a solution in DMF (12 ml) of 470 mg (1.35 mmol) of the resulting N-Me-Val-Tyr(3-tBu)-NH$_2$, 390 mg (1.48 mmol) of Boc-Phe-OH and 230 mg (1.48 mmol) of HOBT, 0.23 ml (1.48 mmol) of DIC was added dropwise under cooling with ice and the mixture was stirred at room temperature for 13 hours and a half. The reaction mixture was diluted with ethyl acetate and washed with saturated brine. The organic layer was dried with anhydrous sodium sulfate and concentrated under reduced pressure; the resulting residue was subjected to silica gel column chromatography (eluting solvent consisting of methylene chloride, methanol and aqueous ammonia at a ratio of 100:3:1) to give Boc-Phe-N-Me-Val-Tyr(3-tBu)-NH$_3$ in the amount of 380 mg (47%).

(5) Synthesis of Phe-N-Me-Val-Tyr(3-tBu)-NH$_2$

A solution of 380 mg (0.638 mmol) of Boc-Phe-N-Me-Val-Tyr(3-tBu)-NH$_2$ in 15 ml of TFA was stirred at room temperature for one hour and a half. The reaction solution was concentrated under reduced pressure and the resulting residue was diluted with ethyl acetate and washed first with saturated aqueous NaHCO$_3$, then with saturated brine. The organic layer was dried with anhydrous sodium sulfate and concentrated under reduced pressure; thereafter, the resulting residue was subjected to silica gel column chromatography (eluting solvent consisting of methylene chloride, methanol and aqueous ammonia at a ratio of 100:10:1) to give Phe-N-Me-Val-Tyr(3-tBu)-NH$_2$ in the amount of 240 mg (76%) FAB-MS: 497 (M+H$^+$); NMR(method g,CDCl$_3$): δ 0.74(2H,d,J=6.6 Hz), 0.79(1H,d,J=6.6 Hz), 0.89(1H,d,J= 6.6 Hz), 0.92(2H,d,J=6.6 Hz), 1.36(3H,s), 1.38(6H,s), 2.27–2.35(1H,m), 2.71(2H,s), 2.81(1H,s), 2.77–3.19(4H,m), 3.56–3.61(2/3H,m), 3.80–3.90(1/3H,m), 3.95(2/3H,d,J= 10.9 Hz), 4.46(1/3H,d,J=11.2 Hz), 4.55–4.65(1/3H,m), 4.70–4.85(2/3H,m), 6.60–7.40(8H,m)

Example 90

N-(α-methylhydrocinnamoyl)-N-Me-D-Phg-Tyr(3-tBu)-NH$_2$ (1) Synthesis of Z-N-Me-Phg-Tyr(3-tBu)-NH$_2$ To a solution of 3.28 g (11.0 mmol) of Z-N-Me-Phg-OH, 2.16 g (9.17 mmol) of Tyr(3-tBu)-NH$_2$ and 1.40 g (9.17 mmol) of HOBT in 60 ml of DMF, 1.42 ml (9.17 mmol) of DIC was added dropwise under cooling with ice and the mixture was stirred for 4 hours under cooling with ice. The reaction mixture was diluted with ethyl acetate and washed with saturated brine. The organic layer was dried with anhydrous sodium sulfate and concentrated under reduced pressure; the resulting residue was subjected to silica gel column chromatography (eluting solvent consisting of methylene chloride, methanol and aqueous ammonia at a ratio of 100:5:1) to give Z-N-Me-Phg-Tyr(3-tBu)-NH$_2$ in the amount of 4.03 g (85%).

(2) Synthesis of N-Me-D-Phg-Tyr(3-tBu)-NH$_2$

A mixture of Z-N-Me-Phg-Tyr(3-tBu)-NH$_2$ (4.03 g) and 10% palladium carbon (2.0 g) in methanol (200 ml) was stirred in a hydrogen atmosphere for 4 hours. The reaction mixture was filtered and the filtrate was distilled off under reduced pressure; the resulting residue was subjected to silica gel column chromatography (eluting solvent consisting of methylene chloride, methanol and aqueous ammonia at a ratio of 100:5:1) to give N-Me-Phg-Tyr(3-tBu)-NH$_2$ in 1.48 g (50%) and N-Me-D-Phg-Tyr(3-tBu)-NH$_2$ in the amount of 920 mg (31%).

(3) Synthesis of N-(α-methylhydrocinnamoyl)-N-Me-D-Phg-Tyr(3-tBu)-NH$_2$

To a solution of α-methylhydrocinnamic acid (141 mg) in 10 ml of thionyl chloride,DMF (0.01 ml) was added and the mixture was stirred at 80° C. for 1.5 hours. The reaction mixture was distilled off under reduced pressure and the resulting residue was dissolved in methylene chloride; the solution was added to a solution of 300 mg (0.78 mmol) of N-Me-D-Phg-Tyr(3-tBu)-NH$_2$ and 260 mg (3.13 mmol) of NaHCO$_3$ in 6 ml of H$_2$O and the mixture was stirred at room temperature for 45 minutes. The reaction mixture was diluted with ethyl acetate and washed first with water, then with saturated brine. The organic layer was dried with anhydrous sodium sulfate and concentrated under reduced pressure; the resulting residue was subjected to silica gel column chromatography (eluting solvent; ethyl acetate:n-hexane=4:1) to yield N-(α-methylhydrocinnamoyl)-N-Me-D-Phg-Tyr( 3-tBu)-NH$_2$ in the amount of 210 mg (51%).

EI-MS: 529(M$^+$); NMR(method g,CDCl$_3$): δ 1.18(3/2H,d, J=6.3 Hz), 1.25(3/2H,d,J=6.9 Hz), 1.35(9H,s), 2.64–3.14 (6H,m), 2.73(3/2H,s), 2.81(3/2H,s), 4.67(1H,dd,J=7.4,14.0 Hz), 5.09(1/2H,s), 5.38(1H, brd,J=8.9 Hz), 5.47(1/2H,s), 5.75(1/2H,s), 5.77(1/2H,s), 5.86(1/2H,s), 6.06(1/2H, brd,J= 7.9 Hz), 6.48–6.72(2H,m), 6.86–7.00(2H,m), 7.14–7.34(9H, m).

Example 91

Phe-Val-N-Me-Tyr(3-tBu)-NH$_2$ (1) Synthesis of Z-Phe(3-tBu-4-benzyloxy)-OMe

To a solution of 1.05 g (2.73 mmol) of Z-Tyr(3-tBu)-OMe in 10 ml of DMF, 120 mg (3.00 mmol) of sodium hydride (60% in oil) and 0.357 ml (3.00 mmol) of benzyl bromide were added under cooling with ice and the mixture was stirred for 4 hours. After neutralization with saturated aqueous ammonium chloride, the reaction mixture was extracted with ethyl acetate and washed first with water, then with saturated brine. The organic layer was dried with anhydrous magnesium sulfate and concentrated under reduced pressure; the resulting residue was subjected to silica gel column chromatography (eluting solvent; ethyl acetate:n-hexane= 1:5) to give Z-Phe(3-tBu-4-benzyloxy)-OMe in the amount of 688 mg (53%).

(2) Synthesis of Z-N-Me-Phe(3-tBu-4-benzyloxy)-OMe

To a solution of 680 mg (1.43 mmol) of Z-Phe(3-tBu-4-benzyloxy)-OMe in 8 ml of DMF, 74.4 mg (1.86 mmol) of sodium hydride (60% in oil) and 0.134 ml (2.15 mmol) of methyl iodide were added under cooling with ice and the mixture was stirred for 1 hour. After neutralization with saturated aqueous ammonium chloride, the reaction mixture was extracted with ethyl acetate and washed first with water, then with saturated brine. The organic layer was dried with anhydrous magnesium sulfate and concentrated under reduced pressure; the resulting residue was subjected to silica gel column chromatography (eluting solvent; ethyl acetate:n-hexane=1:4) to give Z-N-Me-Phe(3-tBu-4-benzyloxy)-OMe in the amount of 659 mg (94%).

(3) Synthesis of N-Me-Tyr(3-tBu)-NH$_2$

To a solution of 655 mg (1.34 mmol) of Z-N-Me-Phe(3-tBu-4-benzyloxy)-OMe in 8 ml of 1,4-dioxane, 2 ml of 2 N aqueous sodium hydroxide was added under cooling with ice and the mixture was stirred at room temperature for 1 hour. The reaction mixture was rendered acidic by addition of 2 N hydrochloric acid, extracted with chloroform and washed first with water, then with saturated brine. The organic layer was dried with anhydrous magnesium sulfate and the solvent was distilled off under reduced pressure; the resulting residue was dissolved in 5 ml of DMF and 0.183 ml (1.66 mmol) of NMM and 0.159 ml (1.66 mmol) of ethyl chloroformate were added to the solution at −15° C., followed by stirring for 20 minutes. The reaction mixture was stirred with bubbling of ammonia gas for additional 30 minutes, left to stand at room temperature, diluted with ethyl acetate and washed first with water, then with saturated brine. The organic layer was dried with anhydrous magnesium sulfate and the solvent was distilled off under reduced pressure; the resulting residue was dissolved in 7 ml of methanol and after addition of 20% palladium hydroxide on carbon (100 mg), the mixture was stirred in a hydrogen atmosphere at room temperature for 4 hours. After filtering, the filtrate was concentrated under reduced pressure to give N-Me-Tyr(3-tBu)-NH$_2$ in the amount of 314 mg (94%).

(4) Synthesis of Boc-Val-N-Me-Tyr(3-tBu)-NH$_2$

To a solution of 120 mg (0.480 mmol) of N-Me-Tyr(3-tBu)-NH$_2$,156 mg (0.718 mmol) of Boc-Val-OH and 110 mg (0.718 mmol) of HOBT in 2 ml of DMF, 0.111 ml (0.718 mmol) of DIC was added under cooling with ice and the mixture was stirred overnight at room temperature. The reaction mixture was diluted with ethyl acetate and washed first with saturated aqueous NaHCO$_3$, then with water, and finally with saturated brine. The organic layer was dried with anhydrous magnesium sulfate and concentrated under reduced pressure; the resulting residue was subjected to silica gel column chromatography (eluting solvent; ethyl acetate:n-hexane=2:1) to give Boc-Val-N-Me-Tyr(3-tBu)-NH$_2$ in the amount of 147 mg (68%).

(5) Synthesis of Z-Phe-Val-N-Me-Tyr(3-tBu)-NH$_2$

To a solution of 146 mg (0.325 mmol) of Boc-Val-N-Me-Tyr(3-tBu)-NH$_2$ in 2 ml of methylene chloride, 1 ml of TFA was added and the mixture was stirred at room temperature for 30 minutes. The solvent was distilled off under reduced pressure. To a solution of the resulting TFA salt of Val-N-Me-Tyr(3-tBu)-NH$_2$ in 2 ml of DMF, 0.1 ml of TEA, 219 mg (0.348 mmol) of Z-Phe-ONp and 93.5 mg (0.765 mmol) of DMAP were added and the mixture was stirred at room temperature for 2 hours. The reaction mixture was diluted with ethyl acetate and washed first with saturated aqueous NaHCO$_3$, then with water and finally with saturated brine. The organic layer was dried with anhydrous magnesium sulfate and concentrated under reduced pressure; the resulting residue was subjected to silica gel column chromatography (eluting solvent; ethyl acetate:n-hexane=1:1) to give Z-Phe-Val-N-Me-Tyr(3-tBu)-NH$_2$ in the amount of 189 mg (92%).

(6) Synthesis of Phe-Val-N-Me-Tyr(3-tBu)-NH$_2$

To a solution of 183 mg (0.290 mmol) of Z-Phe-Val-N-Me-Tyr(3-tBu)-NH$_2$ in 3 ml of methanol, 100 mg of 10% palladium carbon was added and the mixture was stirred in a hydrogen atmosphere at room temperature for 5 hours. After filtering, the filtrate was concentrated under reduced pressure and the resulting residue was subjected to silica gel column chromatography (eluting solvent; ethyl acetate:methanol=10:1) to yield Phe-Val-N-Me-Tyr(3-tBu)-NH$_2$ in the amount of 108 mg (75%). NMR(method g,CDCl$_3$): δ 0.69(3H,dd,J=6.9,17.8 Hz), 0.89(3H,dd,J=6.9, 14.5 Hz), 1.36(9/2H,s), 1.39(9/2H,s), 2.67(1H,dd,J=9.6,13.5 Hz), 2.78–2.94(1H,m), 2.97(3/2H,s), 3.09(3/2H,s), 3.12–3.40(2H,m), 3.59(1H,ddd,J=3.6,9.3,10.2 Hz), 4.34–4.42(1/2H,m), 4.68(1/2H,dd,J=6.6,11.1 Hz), 4.79(1/2H,dd,J=7.9,8.9 Hz), 5.18–5.26(1/2H,m), 5.35(1/2H,brs), 5.49(1/2H,brs), 6.60(1H,dd,J=7.9,12.2 Hz), 6.86(1H,ddd,J=1.6,6.3,6.3 Hz), 7.06(1H,s), 7.16–7.34(5H,m), 7.76(1/2H, brs), 7.85(1/2H,d,J=8.9 Hz), 7.95(1/2H,d,J=7.9 Hz).

Example 92

Phe-Phg-Tyr(3-tBu)-NHMe (1) Synthesis of Tyr(3-tBu)-NHMe

To a solution of 10.6 g (42.0 mmol) of Tyr(3-tBu)-OMe in 80 ml of methanol, 80 ml of a solution of 40% methylamine in methanol and 0.41 g of sodium cyanide were added and the mixture was stirred at room temperature for 4 hours. The reaction mixture was concentrated under reduced pressure and the resulting residue was dissolved in methylene chloride, followed by washing first with water, then with saturated brine. The organic layer was dried with anhydrous sodium sulfate and concentrated under reduced pressure; the resulting residue was subjected to silica gel column chromatography (eluting solvent consisting of chloroform, methanol and aqueous ammonia at a ratio of 20:1:0.1) to give Tyr(3-tBu)-NHMe in the amount of 7.3 g (70%).

(2) Synthesis of Phe-Phg-Tyr(3-tBu)-NHMe

To a solution of 150 mg (0.597 mmol) of Boc-Phg-OH, 136 mg (0.542 mmol) of Tyr(3-tBu)-NHMe, 110 mg (0.813 mmol) of HOBT and 99 mg (0.813 mmol) of DMAP in 3 ml of DMF, 156 mg (0.813 mmol) of WSCI.HCl was added under cooling with ice and the mixture was stirred at room temperature for 4 hours. The reaction mixture was diluted with ethyl acetate and washed first with saturated aqueous NaHCO$_3$, then with water, and finally with saturated brine. After drying the organic layer with anhydrous magnesium sulfate, the solvent was distilled off under reduced pressure and the resulting residue was dissolved in 3 ml of methylene chloride, followed by addition of 2 ml of TFA. After being stirred at room temperature for 15 minutes, the reaction mixture was distilled off under reduced pressure and the resulting residue was dissolved in methylene chloride, followed by washing with saturated aqueous NaHCO$_3$, then with saturated brine. The organic layer was dried with anhydrous magnesium sulfate and the solvent was distilled off under reduced pressure to give a TFA salt of Phg-Tyr(3-tBu)-NHMe. To a solution of 0.44 g of this TFA salt, 158 mg (0.597 mmol) of Boc-Phe-OH, 110 mg (0.813 mmol) of HOBT and 165 mg (1.36 mmol) of DMAP in 5 ml of DMF, 156 mg (0.813 mmol) of WSCI.HCl was added under cooling with ice and the mixture was stirred at room temperature for 2 hours. The reaction mixture was diluted with ethyl acetate and washed first with saturated aqueous NaHCO$_3$, then with water and finally with saturated brine. The organic layer was dried with anhydrous magnesium sulfate and the solvent was distilled off under reduced pressure; the resulting residue was dissolved in 4 ml of methylene chloride and after adding 4 ml of TFA, the mixture was stirred at room temperature for 40 minutes. The reaction mixture was distilled off under reduced pressure and the resulting residue was dissolved in methylene chloride, followed by washing first with saturated aqueous NaHCO$_3$, then with saturated brine. The organic layer was dried with anhydrous magnesium sulfate and concentrated under reduced pressure; the resulting residue was subjected to silica gel column chromatography (eluting solvent consisting of chloroform, methanol and aqueous ammonia at a ratio of 20:1:0.1) to yield Phe-Phg-Tyr(3-tBu)-NHMe in the amount of 158 mg (55% in four steps).

FAB-MS: 531(M+H$^+$); NMR(method g,DMSO-d6): δ 1.30(9H,s), 1.78(1H,brs), 2.6–3.0(4H,m), 3.17(3H,d,J=4.6 Hz), 3.45–3.50(1H,m), 4.05–4.15(1H,m), 4.3–4.4(1H,m), 5.48(1H,s), 6.64(1H,d,J=8.3 Hz), 6.81(1H,dd,J=2.0,8.3 Hz), 6.97(1H,d,J=2.0 Hz), 7.17–7.28(10H,m), 7.71(1H,m), 8.45 (1H,brs), 8.48(1H,d,J=8.2 Hz), 9.11(1H,s).

Example 93

Phe-Apc-Tyr(3-tBu)-NHMe (1) Synthesis of Z-Apc-Tyr(3-tBu)-NHMe

To a solution of 206 mg (0.877 mmol) of Z-Apc-OH, 219 mg (0.876 mmol) of Tyr(3-tBu)-NHMe, 178 mg (1.32 mmol) of HOBT and 214 mg (1.75 mmol) of DMAP in 3 ml of DMF, 252 mg (1.31 mmol) of WSCI.HCl was added and the mixture was stirred at room temperature for 2 hours. The reaction mixture was diluted with ethyl acetate and washed first with saturated aqueous NaHCO$_3$, then with water and finally with saturated brine. The organic layer was dried with anhydrous magnesium sulfate and concentrated under reduced pressure; the resulting residue was subjected to silica gel column chromatography (eluting solvent; ethyl acetate:n-hexane=1:1) to give 205 mg (50%) of Z-Apc-Tyr(3-tBu)-NHMe.

(2) Synthesis of Boc-Phe-Apc-Tyr(3-tBu)-NHMe

To a solution of 201 mg (0.430 mmol) of Z-Apc-Tyr(3-tBu)-NHMe in 3 ml of methanol, 100 mg of 10% palladium carbon was added and the mixture was stirred in a hydrogen atmosphere at room temperature for 2 hours. After filtering, the filtrate was distilled off under reduced pressure and the resulting residue was dissolved in 3 ml of DMF; to the solution under cooling with ice, 228 mg (0.859 mmol) of Boc-Phe-OH, 380 mg (0.859 mmol) of BOP and 0.472 ml (4.30 mmol) of NMM were added and the mixture was stirred at room temperature for 3 days. The reaction mixture was diluted with ethyl acetate and washed first with saturated aqueous $NaHCO_3$, then with water and finally with saturated brine. The organic layer was dried with anhydrous magnesium sulfate and concentrated under reduced pressure; the resulting residue was subjected to silica gel column chromatography (eluting solvent; hexane:ethyl acetate=1:1) to give Boc-Phe-Apc-Tyr(3-tBu)-NHMe in the amount of 108 mg (43%).

(3) Synthesis of Phe-Apc-Tyr(3-tBu)-NHMe

To a solution of 103 mg (0.178 mmol) of Boc-Phe-Apc-Tyr(3-tBu)-NHMe in 2 ml of methylene chloride, 1 ml of TFA was added. After being stirred at room temperature for 1 hour, the reaction mixture was concentrated under reduced pressure and the resulting residue was dissolved in methylene chloride, followed by washing first with saturated aqueous $NaHCO_3$, then with saturated brine. The organic layer was dried with anhydrous magnesium sulfate and concentrated under reduced pressure; the resulting residue was subjected to silica gel column chromatography (eluting solvent consisting of chloroform, methanol and aqueous ammonia at a ratio of 10:1:0.1) to yield Phe-Apc-Tyr(3-tBu)-NHMe in the amount of 68.4 mg (80%).

NMR(method g,$CDCl_3$): δ 1.10–1.40(4H,m), 1.36(9H,s), 2.83(3H,d,J=4.6 Hz), 2.80–3.15(2H,m), 3.30–3.70(3H,m), 4.91(1H,dd,J=7.6,9.7 Hz), 5.56(1H,brs), 6.56(1H,d,J=7.9 Hz), 6.73(1H,brs), 6.89(1H,dd,J=2.0,7.9 Hz), 7.02(1H,d,J=2.0 Hz), 7.10–7.40(6H,m).

Example 94

Phe-Ahc-Tyr(3-tBu)-NHMe (1) Synthesis of Z-Ahc-Tyr(3-tBu)-NHMe

To a solution of 400 mg (1.44 mmol) of Z-Ahc-OH, 360 mg (1.44 mmol) of Tyr(3-tBu)-NHMe, 389 mg (2.88 mmol) of HOBT and 351 mg (2.88 mmol) of DMAP in 5 ml of DMF, 552 mg (2.88 mmol) of WSCI.HCl was added under cooling with ice and the mixture was stirred at room temperature for 2 hours. The reaction mixture was diluted with ethyl acetate and washed first with saturated aqueous $NaHCO_3$, then with water and finally with saturated brine. The organic layer was dried with anhydrous magnesium sulfate and concentrated under reduced pressure; the resulting residue was subjected to silica gel column chromatography (eluting solvent; ethyl acetate:n-hexane=1:2) to give Z-Ahc-Tyr(3-tBu)-NHMe in the amount of 203 mg (28%).

(2) Synthesis of Z-Phe-Ahc-Tyr(3-tBu)-NHMe

To 192 mg (0.377 mmol) of Z-Ahc-Tyr(3-tBu)-NHMe in a mixture of methanol (2 ml) and 1,4-dioxane (1 ml), 100 mg of 10% palladium carbon was added and the mixture was stirred overnight in a hydrogen atmosphere at room temperature. After filtering, the filtrate was concentrated under reduced pressure and the resulting residue was dissolved in 2 ml of DMF; to the solution under cooling with ice, 190 mg (0.452 mmol) of Z-Phe-ONp and 69.1 mg (0.566 mmol) of DMAP were added and the mixture was stirred overnight at room temperature. The reaction mixture was diluted with ethyl acetate and washed first with saturated aqueous $NaHCO_3$, then with water and finally with saturated brine. The organic layer was dried with anhydrous magnesium sulfate and concentrated under reduced pressure; the resulting residue was subjected to silica gel column chromatography (eluting solvent; ethyl acetate:n-hexane=2:1) to give Z-Phe-Ahc-Tyr(3-tBu)-NHMe in the amount of 217 mg (88%).

(3) Synthesis of Phe-Ahc-Tyr(3-tBu)-NHMe

To a solution of 192 mg (0.320 mmol) of Z-Phe-Ahc-Tyr(3-tBu)-NHMe in 2 ml of methanol, 100 mg of 10% palladium carbon was added and the mixture was stirred overnight in a hydrogen atmosphere at room temperature. After filtering, the filtrate was concentrated under reduced pressure and the resulting residue was subjected to silica gel column chromatography (eluting solvent; chloroform:methanol=10:1) to yield Phe-Ahc-Tyr(3-tBu)-NHMe in the amount of 136 mg (81%).

EI-MS: 523 ($M^+$+1); NMR(method g,$CDCl_3$): δ 1.00–1.90(10H,m), 1.37(9H,s), 2.64–2.80(1H,m), 2.75(3H,d,J=4.6 Hz), 2.90–3.15(2H,m), 3.22–3.40(2H,m), 4.52–4.62 (1H,m), 6.19(1H,d,J=8.3 Hz), 6.77(1H,d,J=7.9 Hz), 6.83 (1H,d,J=7.9 Hz), 6.98(1H,s), 7.12–7.38(7H,m), 7.96(1H,s).

Example 95

N-acetyl-transHyp(O-benzyl)-Tyr(3-tBu)-NHMe (1) Synthesis of Boc-transHyp(O-benzyl)-Tyr(3-tBu)-OMe To a solution of 300 mg (0.933 mmol) of Boc-transHyp (O-benzyl)-OH, 281 mg (1.12 mmol) of Tyr(3-tBu)-OMe, 189 mg (1.40 mmol) of HOBT and 171 mg (1.40 mmol) of DMAP in 7 ml of DMF, 268 mg (1.40 mmol) of WSCI.HCl was added under cooling with ice and the mixture was stirred at room temperature for 1 hour. The reaction mixture was diluted with ethyl acetate and washed first with saturated aqueous $NaHCO_3$, then with water and finally with saturated brine. The organic layer was dried with anhydrous magnesium sulfate and concentrated under reduced pressure; the resulting residue was subjected to silica gel column chromatography (eluting solvent; ethyl acetate:n-hexane= 1:1) to give Boc-transHyp(O-benzyl)-Tyr(3-tBu)-OMe in the amount of 505 mg (97%).

(2) Synthesis of transHyp(O-benzyl)-Tyr(3-tBu)-NHMe

To a solution of 500 mg (0.901 mmol) of Boc-transHyp (O-benzyl)-Tyr(3-tBu)-OMe in 5 ml of methanol, 5 ml of a solution of 40% methylamine in methanol and 10 mg of sodium cyanide were added and the mixture was stirred overnight at room temperature. The reaction mixture was concentrated under reduced pressure and the resulting residue was dissolved in methylene chloride, followed by washing first with water, then with saturated brine. The organic layer was dried with anhydrous magnesium sulfate and the solvent was distilled off under reduced pressure; the resulting residue was dissolved in 5 ml of methylene chloride and 3 ml of TFA was added. After being stirred at room temperature for 15 minutes, the reaction mixture was concentrated under reduced pressure and the resulting residue was dissolved in methylene chloride, followed by washing first with saturated aqueous $NaHCO_3$, then with saturated brine. The organic layer was dried with anhydrous magnesium sulfate and the solvent was distilled off under reduced pressure to give transHyp(O-benzyl)-Tyr(3-tBu)-NHMe in the amount of 380 mg (93%).

(3) Synthesis of N-acetyl-transHyp(O-benzyl)-Tyr(3-tBu)-NHMe

To a solution of 104 mg (0.229 mmol) of transHyp(O-benzyl)-Tyr(3-tBu)-NHMe in 1 ml of methylene chloride, 1 ml of pyridine and 0.024 ml (0.344 mmol) of acetyl chloride were added under cooling with ice and the mixture was stirred for 40 minutes. The reaction mixture was diluted with methylene chloride and washed with saturated aqueous $NaHCO_3$; then, the organic layer was dried with anhydrous magnesium sulfate and the solvent was distilled off under reduced pressure. The resulting residue was subjected to silica gel column chromatography (eluting solvent consisting of chloroform, methanol and aqueous ammonia at a ratio of 20:1:0.1) to yield N-acetyl-transHyp(O-benzyl)-Tyr(3-tBu)-NHMe in the amount of 94 mg (83%).

FAB-MS: 496(M+H$^+$); NMR(method g,CDCl$_3$): δ 1.36 (9H,s), 1.93(3H,s), 2.23(2H,dd,J=7.2,6.9 Hz), 2.74(3H,d,J=5.0 Hz), 2.98(1H,dd,J=6.9,14 Hz), 3.10(1H,dd,J=6.5,14 Hz), 3.50(2H,m), 4.18(1H,m), 4.4–4.6(4H,m), 5.88(1H,s), 6.28 (1H,m), 6.60(1H,d,J=7.9 Hz), 6.62(1H,s), 6.81(1H,dd,J=2.0, 5.2 Hz), 6.99(1H,d,J=2.0 Hz), 7.26–7.38(5H,m).

Example 96

Phe-Cha-Phe(3-tBu)-NH$_2$ (1) Synthesis of N-[bis(methylthio)methylene]-3-t-butyphenylalanine To a solution of 1.78 g (15.8 mmol) of potassium t-butoxide in 30 ml of THF, a solution of 3.28 g (15.8 mmol) of N-[bis(methylthio)methylene]glycine ethyl ester (Angew. Chem. Internat. Edit., 14, 426 (1975)) and 2.39 g (10.5 mmol) of 3-t-butylbenzyl bromide (Eur. J. Med. Chem., 23, 477 (1988)) in 10 ml of THF was added at −78° C. and the mixture was stirred at room temperature for 1 hour. Under cooling with ice, 10 ml of water was added, then 5 ml of 2 N aqueous sodium hydroxide was added and the mixture was stirred at room temperature for another 1 hour. Under cooling with ice, 2 N hydrochloric acid was added to the reaction mixture to render it acidic; the reaction mixture was extracted with chloroform and washed first with water, then with saturated brine. The organic layer was dried with anhydrous magnesium sulfate and concentrated under reduced pressure; the resulting residue was subjected to silica gel column chromatography (eluting solvent; ethyl acetate) to give N-[bis(methylthio)methylene]-3-t-butylphenylalanine in the amount of 577 mg (16%).

(2) Synthesis of Phe(3-tBu)-NH$_2$

To a solution of 492 mg (1.51 mmol) of N-[bis-(methylthio)methylene]-3-t-butylphenylalanine in 5 ml of DMF, 0.183 ml (1.66 mmol) of NMM and 0.159 ml (1.66 mmol) of ethyl chloroformate were added at −15° C. and the mixture was stirred for 30 minutes. The reaction mixture was stirred with bubbling of ammonia gas for another 30 minutes, left to stand at room temperature, diluted with ethyl acetate and washed first with water, then with saturated brine. The organic layer was dried with anhydrous magnesium sulfate and the solvent was distilled off under reduced pressure; the resulting residue was dissolved in 3 ml of 1,4-dioxane and, after adding 1 ml of 2 N hydrochloric acid, the solution was stirred at room temperature for 3 days. Under cooling with ice, the solution was neutralized with saturated aqueous NaHCO$_3$, extracted with chloroform, and washed first with water, then with saturated brine. The organic layer was dried with magnesium sulfate and concentrated under reduced pressure; the resulting residue was subjected to silica gel column chromatography (eluting solvent; chloroform:methanol=10:1) to give Phe(3-tBu)-NH$_2$ in the amount of 210 mg (63%).

EI-MS: 221(M$^+$+1); NMR(g method, CDCl$_3$): δ 1.32(9H, s), 2.69(1H,dd,J=9.6,13.5 Hz), 3.29(1H,dd,J=4.0,13.5 Hz), 3.62(1H,dd,J=4.0,9.6 Hz), 5.38(1H,brs), 7.00–7.38(4H,m).

(3) Synthesis of Boc-Cha-Phe(3-tBu)-NH$_2$

To a solution of 205 mg (0.932 mmol) of Phe(3-tBu)-NH$_2$, 351 mg (1.21 mmol) of Boc-Cha-OH, 164 mg (1.21 mmol) of HOBT and 148 mg (1.21 mmol) of DMAP in 4 ml of DMF, 232 mg (1.21 mmol) of WSCI.HCl was added under cooling with ice and the mixture was stirred at room temperature for 1 hour. The reaction mixture was diluted with ethyl acetate and washed first with saturated aqueous NaHCO$_3$, then with water and finally with saturated brine. The organic layer was dried with anhydrous magnesium sulfate and concentrated under reduced pressure; the resulting residue was subjected to silica gel column chromatography (eluting solvent; ethyl acetate:n-hexane=2:1) to give Boc-Cha-Phe(3-tBu)-NH$_2$ in the amount of 326 mg (74%).

(4) Synthesis of Z-Phe-Cha-Phe(3-tBu)-NH$_2$

To a solution of 322 mg (0.681 mmol) of Boc-Cha-Phe (3-tBu)-NH$_2$ in 2 ml of methylene chloride, 1 ml of TFA was added and the mixture was stirred at room temperature for 2 hours. The solvent was distilled off under reduced pressure to give a TFA salt of Cha-Phe(3-tBu)-NH$_2$; to a solution of the TFA salt in 2 ml of DMF, 0.1 ml of TEA, 343 mg (0.817 mmol) of Z-Phe-ONp and 125 mg (1.02 mmol) of DMAP were added and the mixture was stirred at room temperature for 3 hours. The reaction mixture was diluted with ethyl acetate and washed first with saturated aqueous NaHCO$_3$, then with water and finally with saturated brine. The organic layer was dried with anhydrous magnesium sulfate and concentrated under reduced pressure; the resulting residue was subjected to silica gel column chromatography (eluting solvent; chloroform:methanol=10:1) to give Z-Phe-Cha-Phe (3-tBu)-NH$_2$ in the amount of 192 mg (43%).

(5) Synthesis of Phe-Cha-Phe(3-tBu)-NH$_2$

To a solution of 188 mg (0.287 mmol) of Z-Phe-Cha-Phe (3-tBu)-NH$_2$ in 3 ml of methanol, 100 mg of 10% palladium carbon was added and the mixture was stirred overnight in a hydrogen atmosphere at room temperature. After filtering, the filtrate was concentrated under reduced pressure and the resulting residue was subjected to silica gel column chromatography (eluting solvent, chloroform:methanol=10:1) to yield Phe-Cha-Phe(3-tBu)-NH$_2$ in the amount of 69.0 mg (46%).

EI-MS: 520(M$^+$); NMR(method g,CDCl$_3$): δ 0.80–1.75 (13H,m)1.29(9H,s), 2.70(1H,dd,J=8.6,13.5 Hz), 3.00–3.28 (3H,m), 3.40(1H,dd,J=4.0,8.6 Hz), 4.18–4.32(1H,m), 4.66 (1H,dd,J=6.9,6.9 Hz), 5.32(1H,brs), 6.20(1H,brs), 6.50(1H, d,J=7.9 Hz), 7.01(1H,d,J=6.3 Hz), 7.12–7.38(7H,m), 7.58 (1H,d,J=6.9 Hz).

Example 97

N-(benzylaminocarbonyl)-N-Me-D-Phg-Tyr(3-tBu)-NH$_2$

To a solution of benzylamine (27 mg) in methylene chloride (2 ml), 74 mg (0.25 mmol) of triphosgene and 0.04 ml of DIEA were added under cooling with ice and the mixture was stirred at room temperature for 45 minutes. The reaction mixture was distilled off under reduced pressure and the resulting residue was dissolved in methylene chloride and added to a solution of 100 mg (0.26 mmol) of N-Me-D-Phg-Tyr(3-tBu)-NH$_2$ and 84 mg (0.99 mmol) of NaHCO$_3$ in 2 ml of H$_2$O, and the mixture was stirred at room temperature for 5 hours. The reaction mixture was diluted with methylene chloride and washed first with water, then with saturated brine. The organic layer was dried with anhydrous sodium sulfate and the solvent was distilled off under reduced pressure; the resulting residue was subjected to silica gel column chromatography (eluting solvent consisting of chloroform, methanol and aqueous ammonia at a ratio of 100:10:1) to yield N-(benzylaminocarbonyl)-N-Me-D-Phg-Tyr(3-tBu)-NH$_2$ in 70 mg (54%).

EI-MS: 498 (M$^+$-18); NMR(method g,CDCl$_3$): δ 1.34 (9H,s), 2.72(3H,s), 2.93(1H,dd,J=7.6,14.3 Hz), 3.05(1H,dd, J=5.8,14.3 Hz), 4.40(2H, brd,J=5.3 Hz), 4.68(1H,dd,J=7.6, 13.9 Hz), 4.99–5.12(1H,m), 5.70–5.38(1H,m), 5.40(1H,brs), 6.14–6.32(2H,m), 6.55(1H,d,J=7.9 Hz), 6.66(1H,dd,J=1.8, 8.1 Hz), 6.97(1H, d,J=10.2 Hz), 7.07–7.16(1H,m), 7.25–7.36(10H,m).

Example 98

N-(benzyloxycarbonyl)-Phg-Tyr(3-tBu)-NHMe (1) Synthesis of Z-Phg-Tyr(3-tBu)-OMe

To a solution of Z-Phg-OSu (640 mg) in DMF (10 ml), 463 mg (1.84 mmol) of Tyr(3-tBu)-OMe and 408 mg (3.34 mmol) of DMAP were added and the mixture was stirred at room temperature for 1 hour. The reaction mixture was diluted with ethyl acetate and washed first with saturated aqueous $NaHCO_3$, then with water and finally with saturated brine. The organic layer was dried with anhydrous magnesium sulfate and concentrated under reduced pressure; the resulting residue was subjected to silica gel column chromatography (eluting solvent; ethyl acetate:n-hexane=1:1) to give Z-Phg-Tyr(3-tBu)-OMe in the amount of 905 mg (quantitative).

(2) Synthesis of N-(benzyloxycarbonyl)-Phg-Tyr(3-tBu)-NHMe

To a solution of 900 mg (1.73 mmol) of Z-Phg-Tyr(3-tBu)-OMe in 10 ml of methanol, 10 ml of a solution of 40% methylamine in methanol and 10 mg of sodium cyanide were added and the mixture was stirred overnight at room temperature. The reaction mixture was concentrated under reduced pressure and the resulting residue was dissolved in methylene chloride, followed by washing first with water, then with saturated brine. The organic layer was dried with anhydrous magnesium sulfate and concentrated under reduced pressure; the resulting residue was subjected to silica gel column chromatography (eluting solvent; ethyl acetate:n-hexane=2:1) to yield N-(benzyloxycarbonyl)-Phg-Tyr(3-tBu)-NHMe in the amount of 737 mg (82%).

FAB-MS: 518(M+H$^+$); NMR(method g,DMSO-d6): δ 1.30(9H,s), 2.57(3H,d,J=4.3 Hz), 2.5–2.9(2H,m)3.30(1H,d, J=5.3 Hz), 4.0–4.1(1H,m), 4.2–4.4(1H,m), 5.03(2H,s), 5.28 (1H,d,J=8.5 Hz), 6.5–6.8(2H,m), 6.94(1H,d,6.6 Hz), 7.2–7.4 (8H,m), 7.7–7.9(2H,m), 8.46(1H,d,7.6 Hz), 9.06(1H,d).

Example 99

N-(benzyloxycarbonyl)-N-Me-Val-Tyr(3-tBu)-NH$_2$

To a solution of 1.70 g (7.20 mmol) of Tyr(3-tBu)-NH$_2$, 2.10 g (7.92 mmol) of Z-N-Me-Val-OH, 1.07 g (7.92 mmol) of HOBT and 970 mg (7.94 mmol) of DMAP in 20 ml of DMF, 1.52 g (7.93 mmol) of WSCI.HCl was added under cooling with ice and the mixture was stirred at room temperature for 2 hours. The reaction mixture was diluted with ethyl acetate and washed first with saturated aqueous $NaHCO_3$, then with water and finally with saturated brine. The organic layer was dried with anhydrous magnesium sulfate and concentrated under reduced pressure; the resulting residue was subjected to silica gel column chromatography (eluting solvent; ethyl acetate:n-hexane=2:1) to yield N-(benzyloxycarbonyl)-N-Me-Val-Tyr(3-tBu)-NH$_2$ in 3.30 g (95%).

FAB-MS: 484(M+H$^+$); NMR(method g,CDCl$_3$): δ 0.83 (3H,d,J=6.6 Hz), 0.88(3H,d,J=6.6 Hz), 1.36(9H,s), 2.15–2.30(1H,m), 2.75(3H,s), 2.80–3.05(2H,m), 4.02(1H,d, J=10.9 Hz), 4.52–4.64(1H,m), 5.13(2H,s), 5.39(1H,brs), 5.88(1H,brs), 6.40–6.84(3H,m), 7.08(1H,s), 7.28–7.42(5H, m).

Example 100

N-((R)-3-phenylbutyryl)-Phg-Tyr(3-tBu)-NH$_2$

A reaction vessel was charged with 182 mg (0.1 mmol) of Fmoc-2,4-dimethoxy-4-(carboxymethyloxy)- benzhydrylamine linked to Aminomethyl Resin (0.55 mmol/g); after being swelled with DMF, the resin was treated with piperidine to remove Fmoc. Subsequently, Fmoc-Tyr(3-tBu)-OH was coupled by method 1. After filtering and washing with DMF, the resin was treated with piperidine to remove Fmoc. Subsequently, Fmoc-Phg-OH was coupled by method 3. After filtering and washing with DMF, the resin was treated again with piperidine to remove Fmoc. Subsequently, (R)-3-phenylbutyric acid was coupled by method 3. After the end of the reaction, filtering and washing with DMF and DCM were effected, followed by drying of the resin. Cleavage was effected with 3 ml of 95% aqueous TFA. The reaction solution was concentrated under reduced pressure and the residue was dissolved in 1 ml of DMF, followed by HPLC purification. The active fractions were collected, concentrated and freeze-dried to yield 15.6 mg of the titled compound.

HPLC (method a):RT22.96; FAB-MS: 516(M+H$^+$); NMR (method f,DMSO-d6): δ 1.16(3H,d,J=7 Hz), 1.32(9H,s), 2.41(1H,dd,J=14,8 Hz), 2.56(1H,dd,J=14,8 Hz), 2.74(1H, dd,J=14,9 Hz), 2.89(1H,dd,J=14,5 Hz), 3.15(1H,ddq,J=8,8,7 Hz), 4.38(1H,ddd,J=9,8,5 Hz), 5.42(1H,d,J=8 Hz), 6.63(1H, d,J=8 Hz), 6.81(1H,dd,J=8,2 Hz), 7.01(2H,brs), 7.05–7.30 (11H,m), 8.30(1H,d,J=8 Hz), 8.31(1H,d,J=8 Hz), 9.08(1H, s).

Example 101

N-((S)-3-phenylbutyryl)-Phg-Tyr(3-tBu)-NH$_2$

Substituting (S)-3-phenylbutyric acid for the (R)-3-phenylbutyric acid used in Example 100, the procedure of Example 100 was repeated to yield 13.3 mg of the titled compound.

HPLC (method a):RT23.00; FAB-MS: 516(M+H$^+$); NMR (method f,DMSO-d6): δ 1.11(3H,d,J=8 Hz), 1.30(9H,s), 2.40(1H,dd,J=14,6 Hz), 2.52(1H,dd,J=14,10 Hz), 2.69(1H, dd,J=14,9 Hz), 2.89(1H,dd,J=14,5 Hz), 3.13(1H,ddq,J=10, 6,8 Hz), 4.36(1H,ddd,J=9,8,5 Hz), 5.47(1H,d,J=8 Hz), 6.62 (1H,d,J=8 Hz), 6.79(1H,dd,J=8,2 Hz), 6.99(1H,d,J=2 Hz), 7.00(1H,s), 7.10–7.30(11H,m), 8.20(1H,d,J=8 Hz), 8.43(1H, d,J=8 Hz), 9.08(1H,s)

Example 102

N-((R)-3-phenylbutyryl)-D-Phg-Tyr(3-tBu)-NH$_2$

Substituting Fmoc-D-Phg-OH for the Fmoc-Phg-OH used in Example 100, the procedure of Example 100 was repeated to yield 7.2 mg of the titled compound.

HPLC (method a):RT23.07; FAB-MS: 516(M+H$^+$); NMR (method g,DMSO-d6): δ 1.13(3H,d,J=7 Hz), 1.27(9H,s), 2.38–2.64(3H,m), 2.88(1H,dd,J=14,4 Hz), 3.15(1H,m), 4.26 (1H,m), 5.50(1H,d,J=8 Hz), 6.53(1H,d,J=8 Hz), 6.69(1H, dd,J=8,1 Hz), 6.98(1H,brs), 7.10–7.42(12H,m), 8.48(1H,d, J=8 Hz), 8.54(1H,d,J=8 Hz), 9.06(1H,s).

Example 103

N-((S)-3-phenylbutyryl)-D-Phg-Tyr(3-tBu)-NH$_2$

Substituting Fmoc-D-Phg-OH for the Fmoc-Phg-OH used in Example 101, the procedure of Example 101 was repeated to yield 16.1 mg of the titled compound.

HPLC (method a):RT22.98; FAB-MS: 516(M+H$^+$); NMR (method g,DMSO-d6): δ 1.17(3H,d,J=7 Hz), 1.27(9H,s), 2.39–2.65(3H,m), 2.91(1H,dd,J=14,3 Hz), 3.16(1H,m), 4.28 (1H,m), 5.42(1H,d,J=8 Hz), 6.55(1H,d,J=8 Hz), 6.73(1H, dd,J=8,1 Hz), 6.80–7.44(13H,m), 8.37(1H,d,J=8 Hz), 8.58 (1H,d,J=8 Hz), 9.07(1H,s).

Example 104

L-α-(3-methyl-2-butenyl)glycyl-N-Me-Val-Tyr(3-tBu)-NH$_2$

To a solution in 6 ml of DMF of 228 mg (0.653 mmol) of the N-Me-Val-Tyr(3-tBu)-NH$_2$ prepared in Example 89, 340 mg (1.40 mmol) of Boc-L-α-(3-methyl-2-butenyl)glycine (Bioorg. Med. Chem. Lett., 2, 387 (1992)) and 189 mg (1.40 mmol) of HOBT, 0.22 ml (1.40 mmol) of DIC was added under cooling with ice. After being stirred at room temperature for a day, the reaction mixture was diluted with ethyl acetate and washed first with saturated aqueous NaHCO$_3$, then with water and finally with saturated brine. The organic layer was dried with anhydrous magnesium sulfate and concentrated under reduced pressure; the resulting residue was subjected to silica gel column chromatography (eluting solvent consisting of chloroform, methanol and aqueous ammonia at a ratio of 50:1:0.1) to give Boc-L-α-(3-methyl-2-butenyl)-glycyl-N-Me-Val-Tyr(3-tBu)-NH$_2$ in the amount of 0.17 g (45%).

Subsequently, 1 ml of TFA was added to a solution of Boc-L-α-(3-methyl-2-butenyl)glycyl-N-Me-Val-Tyr(3-tBu)-NH$_2$ (0.17 g) in methylene chloride (2 ml) and the mixture was stirred at room temperature for 10 minutes. The reaction mixture was concentrated under reduced pressure and the resulting residue was diluted with methylene chloride. The solution was washed with saturated aqueous NaHCO$_3$ and concentrated under reduced pressure. The resulting residue was subjected to silica gel column chromatography (eluting solvent consisting of chloroform, methanol and aqueous ammonia at a ratio of 20:1:0.1) to yield L-α-(3-methyl- 2-butenyl)glycyl-N-Me-Val-Tyr(3-tBu)-NH$_2$ in the amount of 131 mg (93%).

FAB-MS: 475(M+H$^+$); NMR(method g,CDCl$_3$): δ 0.79 (2H,d,J=6.6 Hz), 0.82(1H,d,J=6.6 Hz), 0.89(1H,d,J=6.3 Hz), 0.95(2H,d,J=6.3 Hz), 1.36(6H,s), 1.38(3H,s), 1.62(3H,s), 1.69(3H,s), 2.2–2.4(3H,m), 2.67(2H,s), 2.9–3.1(2H,m), 2.97 (1H,s), 3.40(6.5/10H,m), 3.65(3.5/10H,m), 4.00(6.5/10H,d, J=10.9 Hz), 4.39(3.5/10H,d,J=10.9 Hz), 4.50–4.80(1H,m), 4.95–5.10(1H,m), 5.57(1H,brs), 5.91(3/10H,brs), 6.07(7/10H,brs), 6.60–6.72(23/10H,m), 6.87–6.96(1H,m), 7.03(7/10H,s), 7.09(3/10H,s), 9.19(7/10H,d,J=7.6 Hz).

Example 105

α-(4-pentynyl)glycyl-N-Me-Val-Tyr(3-tBu)-NH$_2$ (1) Synthesis of Boc-DL-α-(4-pentynyl)glycine To a solution of 0.45 g (4.00 mmol) of potassium t-butoxide in 6 ml of THF, 690 mg (3.33 mmol) of N-[bis (methylthio)methylene]glycine ethyl ester in 2 ml of THF was added at −78° C. in a nitrogen atmosphere. After stirring for 15 minutes, a solution of 777 mg (4.00 mmol) of 5-iodo-1-pentyne (J. Chem. Soc. Perkin Trans. I, 2909 (1990)) in 2 ml of THF was added and the mixture was stirred at room temperature for 1.5 hours. To the reaction mixture, saturated aqueous NaHCO$_3$ was added and extraction was effected with ethyl acetate. The organic layer was washed with saturated brine, dried with anhydrous magnesium sulfate and the solvent was distilled off under reduced pressure. The resulting residue was dissolved in a mixture of dioxane (2 ml) and water (4 ml) and, after adding 4 ml of a solution of 10% hydrochloric acid in methanol, the reaction mixture was stirred overnight at room temperature. Thereafter, 2 N aqueous NaOH was added to the reaction mixture to make it alkaline and it was extracted with methylene chloride; then, dioxane (5 ml) and di-tert-butyl dicarbonate (1.5 g) were added to the aqueous layer. After being stirred overnight, the aqueous layer was rendered acidic by addition of 2 N hydrochloric acid, extracted with methylene chloride and dried with anhydrous magnesium sulfate; thereafter, the solvent was distilled off under reduced pressure to give 0.46 g of Boc-DL-α-(4-pentynyl) glycine in crude form. NMR(method g,CDCl$_3$): δ 1.45(9H, s), 1.60–1.70(2H,m), 1.80(1H,m), 1.97(1H,t,J=2.6 Hz), 1.98 (1H,m), 2.25(2H,dt,J=2.6,6.9 Hz), 4.35(1H,brs), 5.02(1H, brs).

(2) Synthesis of Boc-α-(4-pentynyl)glycyl-N-Me-Val-Tyr (3-tbu)-NH$_2$

To a solution in DMF (5 ml) of 0.34 g (1.41 mmol) of the crude Boc-DL-α-(4-pentynyl)glycine, 200 mg (0.572 mmol) of N-Me-Val-Tyr(3-tBu)-NH$_2$ prepared in accordance with Example 89 and 150 mg (1.14 mmol) of HOBT, 0.18 ml (1.14 mmol) of DIC was added under cooling with ice. After being stirred at room temperature for 19 hours, the reaction mixture was diluted with ethyl acetate and washed with saturated aqueous NaHCO$_3$, water and saturated brine. The organic layer was dried with anhydrous magnesium sulfate and concentrated under reduced pressure; the resulting residue was subjected to silica gel column chromatography (eluting solvent consisting of chloroform, methanol and aqueous ammonia at a ratio of 50:1:0.1) to give Boc-α-(4-pentynyl)glycyl-N-Me-Val-Tyr(3-tBu)-NH$_2$ both as a compound of low polarity in an amount of 202 mg (61%) and as a compound of high polarity in an amount of 65 mg (20%).

(3) Synthesis of α-(4-pentynyl)glycyl-N-Me-Val-Tyr(3-tBu)-NH$_2$

Each of the above-mentioned compounds of low polarity (195 mg) and high polarity (60 mg) was dissolved in 2 ml of methylene chloride and, after adding 1 ml of TFA, the mixtures were stirred at room temperature for 15 minutes. The solvent was distilled off under reduced pressure and the resulting residue was diluted with methylene chloride. The organic layer was washed with saturated aqueous NaHCO$_3$ and concentrated under reduced pressure. The resulting residue was subjected to silica gel column chromatography (eluting solvent consisting of chloroform, methanol and aqueous ammonia at a ratio of 20:1:0.1) to yield α-(4-pentynyl)glycyl-N-Me-Val-Tyr(3-tBu)-NH$_2$ from the compound of low polarity in an amount of 101 mg (63%) and from the compound of high polarity in an amount of 17 mg (34%).

Compound of low polarity; FAB-MS: 473(M+H$^+$); NMR (method g,CDCl$_3$): δ 0.75(3H,d,J=6.6 Hz), 0.91(3H,d,J=6.3 Hz), 1.37(9H,s), 1.4–1.8(4H,m), 1.93(1H,t,J=2.5 Hz), 2.17–2.27(3H,m), 2.69(3H,s), 2.82(1H,dd,J=10.1,14.2 Hz), 3.18(1H,dd,J=5.6,14.2 Hz), 3.53(1H,m), 4.52(1H,d,J=10.9 Hz), 4.63(1H,m), 5.90(1H,brs), 6.31(1H,brs), 6.64(1H,d,J= 7.3 Hz), 6.65(1H,d,J=7.9 Hz), 6.78(1H,d,J=7.9 Hz), 7.06 (1H,s).

Compound of high polarity; FAB-MS: 473(M+H$^+$); NMR (method g,CDCl$_3$): δ 0.78–0.97(6H,m), 1.37(6H,s), 1.39 (3H,s), 1.4–1.8(4H,m), 1.96(1H,m), 2.17–2.22(2H,m), 2.33 (1H,m), 2.66(2H,s), 2.87–3.11(2H,m), 2.97(1H,s), 3.43–3.69(14/10H,m), 3.98(7/10H,d, J=10.9 Hz), 4.42(3/10H, d,J=10.9 Hz), 4.48–4.76(1H,m), 5.43(1H,brs), 5.81(3/10H,brs), 6.08(7/10H,brs), 6.62–6.77(2H,m), 6.81(3/10H,d, J=7.9 Hz), 6.90(7/10H,d,J=7.9 Hz), 7.03(7/10H,s), 7.10(3/10H,s), 9.03 (6/10H,d,J=7.3 Hz).

Example 106

α-(2-butynyl)glycyl-N-Me-Val-Tyr(3-tBu)-NH$_2$ (1) Synthesis of Boc-DL-α-(2-butynyl)glycine ethyl ester To a solution of 0.40 g (3.55 mmol) of potassium t-butoxide in 6 ml of THF, 610 mg (2.96 mmol) of N-[bis (methylthio)methylene]glycine ethyl ester in 2 ml of THF was added at −78° C. After stirring for 20 minutes, a solution of 640 mg (3.55 mmol) of 1-iodo-2-butyne (Chem. Lett., 621 (1981)) in 2 ml of THF was added and the resulting mixture was stirred at room temperature for 30 minutes. Saturated aqueous $NaHCO_3$ was added to the reaction mixture, which was extracted with ethyl acetate. The organic layer was washed with saturated brine, dried with anhydrous magnesium sulfate and the solvent was distilled off under reduced pressure. The resulting residue was dissolved in a mixture of dioxane (2 ml) and water (4 ml) and, after adding 10% hydrochloric acid in methanol (4 ml), the mixture was stirred overnight at room temperature. Thereafter, the reaction mixture was neutralized with 2 N aqueous NaOH, rendered alkaline with saturated aqueous $NaHCO_3$, extracted with methylene chloride, dried with anhydrous sodium carbonate and the solvent was distilled off under reduced pressure.

To a solution of the resulting residue in 5 ml of methylene chloride, di-tert-butyl bicarbonate (0.65 g) was added and the mixture was stirred for 1 hour. The reaction mixture was washed with water, dried with anhydrous magnesium sulfate and concentrated under reduced pressure; the resulting residue was subjected to silica gel column chromatography (eluting solvent; ethyl acetate:n-hexane=1:6) to give Boc-DL-α-(2-butynyl)glycine ethyl ester in the amount of 575mg (76%). NMR(method g,$CDCl_3$): δ 1.29(3H,t,J=7.3 Hz) 1.46(9H,s), 1.77(3H,t,J=2.6 Hz), 2.56–2.77(2H,m), 4.18–4.27(2H,m), 4.38(1H,m), 5.30(1H,brs).

(2) Synthesis of Boc-α-(2-butynyl)glycyl-N-Me-Val-Tyr(3-tBu)-$NH_2$

To a solution of 570 mg (2.23 mmol) of Boc-DL-α-(2-butynyl)glycine ethyl ester in a solvent system of methanol (6 ml) and water (2 ml), 140 mg (3.35 mmol) of lithium hydroxide monohydrate was added and the mixture was stirred at room temperature for 2 hours. The mixture was rendered acidic with 2 N hydrochloric acid under cooling with ice, extracted with methylene chloride, dried with anhydrous magnesium sulfate and the solvent was distilled off under reduced pressure to give Boc-DL-α-(2-butynyl) glycine in the amount of 0.50 g (quantitative).

To a solution in DMF (4 ml) of 123 mg (0.541 mmol) of the Boc-DL-α-(2-butynyl)glycine, 378 mg (1.08 mmol) of N-Me-Val-Tyr(3-tBu)-$NH_2$ prepared in accordance with Example 89 and 146 mg (1.08 mmol) of HOBT, 0.13 ml (0.811 mmol) of DIC was added under cooling with ice. After being stirred overnight at room temperature, the reaction mixture was diluted with ethyl acetate and washed with saturated aqueous $NaHCO_3$, water and saturated brine. The organic layer was dried with anhydrous magnesium sulfate and concentrated under reduced pressure; the resulting residue was subjected to silica gel column chromatography (eluting solvent consisting of chloroform, methanol and aqueous ammonia at a ratio of 50:1:0.1) to give Boc-α-(2-butynyl)glycyl-N-Me-Val-Tyr(3-tBu)-$NH_2$ both as a compound of low polarity in an amount of 138 mg and as a compound of high polarity in an amount of 59 mg.

(3) Synthesis of α-(2-butynyl)glycyl-N-Me-Val-Tyr(3-tBu)-$NH_2$

Each of the above-mentioned compounds of low polarity (138 mg) and high polarity (59 mg) was dissolved in 2 ml of methylene chloride and, after adding 1 ml of TFA, the mixtures were stirred at room temperature for 15 minutes. The solvent was distilled off under reduced pressure and the resulting residue was diluted with methylene chloride, followed by washing with saturated aqueous $NaHCO_3$. The organic layer was concentrated under reduced pressure and the resulting residue was subjected to silica gel column chromatography (eluting solvent consisting of chloroform, methanol and aqueous ammonia at a ratio of 20:1:0.1) to yield α-(2-butynyl) glycyl-N-Me-Val-Tyr(3-tBu)-$NH_2$ from the compound of low polarity in an amount of 80 mg and from the compound of high polarity in an amount of 47 mg.

Compound of low polarity; FAB-MS: 459(M+H$^+$); NMR (method g,$CDCl_3$): δ 0.75(3H,d,J=6.6 Hz), 0.90(3H,d,J=6.6 Hz), 1.38(9H,s), 1.77(3H,s), 2.1–2.5(6H,m), 2.74(3H,s), 2.81(1H,dd,J=9.9,14.2 Hz), 3.18(1H,dd,J=5.6,14.2 Hz), 3.66(1H,dd,J=5.0,7.6 Hz), 4.47(1H,d,J=11.2 Hz), 4.57(1H, m), 5.66(1H,brs), 6.26(1H,brs), 6.47(1H,d,J=7.3 Hz), 6.64 (1H,d,J=7.9 Hz), 6.78(1H,d,J=7.9 Hz), 7.05(1H,s).

Compound of high polarity; FAB-MS: 459(M+H$^+$); NMR (method g,$CDCl_3$): δ 0.78–0.96(6H,m), 1.38(6H,s), 1.39 (3H,s), 1.78(3H,s), 2.30–2.45(4H,m), 2.68(2H,s), 2.92–3.13 (2H,m), 2.97(1H,s), 3.48(1H,dd,J=4.3,9.2 Hz), 3.98(7/10H, d,J=11.2 Hz), 4.42(3/10H,d,J=11.2 Hz), 4.53–4.78(1H,m), 5.52(1H,brs), 6.14(1H,brs), 6.62–6.70(2H,m), 6.81(3/10H, d,J=7.9 Hz), 6.90(7/10H,d,J=7.9 Hz), 7.04(7/10H,s), 7.10(3/ 10H,s), 9.10(1H,d,J=7.3 Hz).

Example 107

N-((S)-3-phenylbutyryl)-N-Me-Val-Tyr(3-tBu)-$NH_2$

To a solution in DMF (3 ml) of 0.11 ml (0.736 mmol) of (S)-3-phenyl-n-butyric acid, 234 mg (0.670 mmol) of N-Me-Val-Tyr(3-tBu)-$NH_2$ prepared in accordance with Example 89, and 99 mg (0.736 mmol) of HOBT, 0.11 ml (0.736 mmol) of DIC was added under cooling with ice. After being stirred at room temperature for 25 hours, the reaction mixture was diluted with ethyl acetate and washed with saturated $NaHCO_3$, water and saturated brine. The organic layer was dried with anhydrous magnesium sulfate and concentrated under reduced pressure; the resulting residue was subjected to silica gel column chromatography (eluting solvent consisting of chloroform, methanol and aqueous ammonia at a ratio of 50:1:0.1) to yield N-((S)-3-phenylbutyryl)-N-Me-Val-Tyr(3-tBu)-$NH_2$ in the amount of 259 mg (78%).

EI-MS: 496(M$^+$); NMR(method g,$CDCl_3$): δ 0.76(3H,d, J=6.6 Hz), 0.89(3H,d,J=6.3 Hz), 1.27(3H,d,J=6.9 Hz), 1.34 (9H,s), 2.17–2.31(1H,m), 2.38–2.57(2H,m), 2.72(3H,s), 2.81(1H,dd,J=8.2,14.2 Hz), 2.96(1H,dd,J=6.3,14.2 Hz), 3.34(1H,m), 4.46(1H,d,J=11.2 Hz), 4.56(1H,m), 5.50(1H,s), 5.59(1H,brs), 6.00(1H,brs), 6.45(1H,d,J=7.9 Hz), 6.66(1H, d,J=7.6 Hz), 6.78(1H,dd,J=1.7,7.9 Hz), 7.05(1H,d,J=1.7 Hz), 7.20–7.36(5H,m).

Example 108

N-((R)-3-phenylbutyryl)-N-Me-Val-Tyr(3-tBu)-$NH_2$

To a solution in DMF (3 ml) of 0.085 ml (0.558 mmol) of (R)-3-phenyl-n-butyric acid, 150 mg (0.429 mmol) of N-Me-Val-Tyr(3-tBu)-$NH_2$ prepared in accordance with Example 89, and 75 mg (0.558 mmol) of HOBT, 0.087 ml (0.558 mmol) of DIC was added under cooling with ice. After being stirred at room temperature for 25 hours, the reaction mixture was diluted with ethyl acetate and washed with saturated $NaHCO_3$, water and saturated brine. The organic layer was dried with anhydrous magnesium sulfate and concentrated under reduced pressure; the resulting residue was subjected to silica gel column chromatography (eluting solvent consisting of chloroform, methanol and aqueous ammonia at a ratio of 50:1:0.1) to yield N-((R)-3-phenylbutyryl)-N-Me-Val-Tyr(3-tBu)-NH$_2$ in the amount of 186 mg (87%).

EI-MS: 497(M$^+$+1); NMR(method g,CDCl$_3$): δ 0.51(3H, d,J=6.6 Hz), 0.82(3H,d,J=6.6 Hz), 1.31(3H,d,J=7.3 Hz), 1.38(9H,s), 2.04–2.23(1H,m), 2.38(1H,dd,J=7.3,14.8 Hz), 2.65(1H,dd,J=7.6,14.8 Hz), 2.73(3H,s), 2.90(1H,dd,J=7.9, 14.2 Hz), 3.00(1H,dd,J=6.3,14.2 Hz), 3.30(1H,m), 4.36(1H, d,J=10.9 Hz), 4.60(1H,m), 5.67(1H,brs), 5.99(1H,brs), 6.15 (1H,brs), 6.63(1H,d,J=8.3 Hz), 6.76(1H,d,J=7.9 Hz), 6.82 (1H,d,J=7.9 Hz), 7.07(1H,s), 7.17–7.29(5H,m).

Example 109

N-(β-aminohydrocinnamoyl)-N-Me-Val-Tyr(3-tBu)-NH$_2$

To a mixture of 0.67 g (4.05 mmol) of β-aminohydrocinnamic acid, 0.45 g (4.26 mmol) of sodium carbonate, 2.5 ml of 2 N aqueous NaOH, 8 ml of water and 8 ml of dioxane, 0.93 g (4.26 mmol) of di-tert-butyl dicarbonate was added and the resulting mixture was stirred at room temperature for 3 hours. Under cooling with ice, the reaction mixture was rendered acidic with conc. hydrochloric acid, extracted with methylene chloride, dried with anhydrous magnesium sulfate and the solvent was distilled off under reduced pressure to give 1.14 g of N-Boc-β-aminohydrocinnamic acid.

To a solution in DMF (5 ml) of 0.27 g (1.03 mmol) of N-Boc-β-aminohydrocinnamic acid, 0.24 g (0.687 mmol) of N-Me-Val-Tyr(3-tBu)-NH$_2$ prepared in accordance with Example 89 and 0.23 g (1.72 mmol) of HOBT, 0.27 ml (1.72 mmol) of DIC was added under cooling with ice. After being stirred at room temperature for a day, the reaction mixture was diluted with ethyl acetate and washed with saturated aqueous NaHCO$_3$, water and saturated brine. The organic layer was dried with anhydrous magnesium sulfate and concentrated under reduced pressure; the resulting residue was subjected to silica gel column chromatography (eluting solvent consisting of chloroform, methanol and aqueous ammonia at a ratio of 60:1:0.1) to give N-(N-boc-β-aminohydrocinnamoyl)-N-Me-Val-Tyr(3-tBu)-NH$_2$ in the amount of 291 mg (71%).

A portion (285 mg) of the N-(N-Boc-β-aminohydrocinnamoyl)-N-Me-Val-Tyr(3-tBu)-NH$_2$ was dissolved in 2 ml of methylene chloride and, after adding 1 ml of TFA, the mixture was stirred at room temperature for 15 minutes. The solvent was distilled off under reduced pressure and the resulting residue was diluted with methylene chloride and washed with saturated aqueous NaHCO$_3$. The organic layer was concentrated under reduced pressure and the resulting residue was subjected to silica gel column chromatography (eluting solvent consisting of chloroform, methanol and aqueous ammonia at a ratio of 20:1:0.1) to yield N-(β-aminohydro-cinnamoyl)-N-Me-Val-Tyr (3-tBu)-NH$_2$ in the amount of 197 mg (83%).

FAB-MS: 497(M+H$^+$).

Example 110

N-(2-amino-3-phenylpropyl)-Phg-Tyr(3-tBu)-NH$_2$

To a solution of 120 mg (0.325 mmol) of Phg-Tyr(3-tBu)-NH$_2$ and 112 mg (0.396 mmol) of Z-phenylalaninal (J. Org. Chem., 57, 28 (1992)) in 3 ml of MeCN, 0.1 ml of acetic acid and 41.5 mg (0.661 mmol) of sodium cyanoborohydride were added under cooling with ice and the resulting mixture was stirred for 2 hours. After adding water, the reaction mixture was extracted with ethyl acetate and washed with water and saturated brine. The organic layer was dried with magnesium sulfate and concentrated under reduced pressure; the resulting residue was subjected to silica gel column chromatography (eluting solvent; chloroform:methanol=20:1) to give N-(2-benzoxycarbonylamino-3-phenylpropyl)-Phg-Tyr(3-tBu)-NH$_2$ in the amount of 187 mg (89%).

To a solution of 40.0 mg (0.0664 mmol) of N-(2-benzoxycarbonylamino-3-phenylpropyl)-Phg-Tyr(3-tBu)-NH$_2$ in methanol (1 ml), 10% palladium carbon (15.0 mg) was added and the mixture was stirred overnight in a hydrogen atmosphere at room temperature. After filtering, the filtrate was concentrated under reduced pressure and the resulting residue was subjected to silica gel column chromatography (eluting solvent consisting of chloroform, methanol and aqueous ammonia at a ratio of 10:1:0.1) to yield N-(2-amino-3-phenylpropyl)-Phg-Tyr (3-tBu)-NH$_2$ in the amount of 29.0 mg (92%).

EI-MS: 503(M$^+$+1); NMR(method g,CDCl$_3$): δ 1.36(9H, s), 2.20–3.05(7H,m), 3.47(1H,s) 4.08(1H,d,J=4.6 Hz), 4.54–4.72(1H,m), 5.56(1H,brs), 6.56(1H,d,J=7.9 Hz), 6.81 (1H,d,J=7.9 Hz), 7.02–7.30(11H,m), 8.01(1H,d,J=8.4 Hz).

Example 111

N-(2-amino-3-phenylpropyl)-N-Me-Phg-Tyr(3-tBu)-NH$_2$

To a solution of 60.0 mg (0.0943 mmol) of N-(2-benzoxycarbonylamino-3-phenylpropyl)-Phg-Tyr(3-tBu)-NH$_2$ in MeCN (1 ml), 0.081 ml (0.94 mmol) of 35% aqueous formaldehyde, 0.1 ml of acetic acid and 18.7 mg (0.283 mmol) of sodium cyanoborohydride were added under cooling with ice and the resulting mixture was stirred for 2 hours. The reaction mixture was diluted with water, extracted with chloroform and washed with saturated brine. The organic layer was dried with magnesium sulfate and the solvent was distilled off under reduced pressure. The resulting residue was dissolved in methanol (1 ml) and, after adding palladium carbon (15.0 mg), the solution was stirred at room temperature for 3 days in a hydrogen atmosphere. After filtering, the filtrate was concentrated under reduced pressure and the resulting residue was subjected to silica gel column chromatography (eluting solvent consisting of chloroform, methanol and aqueous ammonia at a ratio of 10:1:0.1) to yield N-(2-amino-3-phenylpropyl)-N-Me-Phg-Tyr(3-tBu)-NH$_2$ in the amount of 29.7 mg (61%).

FAB-MS: 517(M+H$^+$); NMR(method g,CDCl$_3$): δ 1.38 (9H,s), 2.07(2H,s), 2.16–3.20(7H,m), 3.47(3H,s), 4.13(1H, s), 4.60–4.80(1H,m), 5.46–5.60(1H,m), 6.52–7.32(13H,m), 8.15(1H,d,J=7.9 Hz).

Example 112

N-(phenylpyruvinoyl)-N-Me-Val-Tyr(3-tBu)-NH$_2$

To a solution of 179 mg (1.09 mmol) of phenylpyruvic acid in methylene chloride (2 ml), 0.079 ml (1.1 mmol) of thionyl chloride was added and the resulting mixture was stirred at 60° C. for 1 hour. The reaction mixture was distilled off under reduced pressure and the resulting residue was dissolved in methylene chloride (2 ml); to the solution, 190 mg (0.544 mmol) of N-Me-Val-Tyr(3-tBu)-NH$_2$ and 0.152 ml (1.09 mmol) of triethylamine were added under cooling with ice. After stirring at room temperature for 2 hours, water was added to the reaction mixture, which was then extracted with chloroform and washed with saturated brine. The organic layer was dried with magnesium sulfate and concentrated under reduced pressure; the resulting residue was subjected to silica gel column chromatography (eluting solvent consisting of methylene chloride, methanol and aqueous ammonia at a ratio of 20:1:0.1) to yield N-(phenylpyruvinoyl)-N-Me-Val-Tyr(3-tBu)-NH$_2$ in the amount of 50.7 mg (19%).

NMR(method g,CDCl$_3$): δ 0.97(3H,d,J=6.6 Hz), 0.99(3H, d,J=6.6 Hz), 1.37(9H,s), 2.30–2.52(1H,m), 2.85(3H,s), 2.92–3.16(2H,m), 4.53(1H,d,J=10.9 Hz), 4.63(1H,dd,J=7.3, 7.3 Hz), 5.46(2H,brs), 5.84(1H,brs), 6.59(1H,d,J=7.9 Hz), 6.95(1H,d,J=6.9 Hz), 7.12(1H,s), 7.44(2H, t,J=7.6 Hz), 7.60–7.70(1H,m), 7.95(2H,d,J=7.6 Hz).

Example 113

N-phenyl-Gly-N-Me-Val-Tyr(3-tBu)-NH$_2$

To a solution of 108 mg (0.430 mmol) of Boc-N-phenyl-Gly in THF (1 ml), 0.048 ml (0.44 mmol) of N-methylmorpholine, 0.056 ml (0.43 mmol) of isobutyl chloroformate, a solution of 100 mg (0.287 mmol) of N-Me-Val-Tyr(3-tBu)-NH$_2$ in DMF (1 ml), and 0.060 ml (0.43 mmol) of triethylamine were added at −15° C. and the resulting mixture was stirred at room temperature for 2 hours. The reaction mixture was diluted with ethyl acetate and washed successively with saturated NaHCO$_3$, water and saturated brine. The organic layer was dried with magnesium sulfate and concentrated under reduced pressure; the resulting residue was subjected to silica gel column chromatography (eluting solvent; ethyl acetate:n-hexane=1:1) to give Boc-N-phenyl-Gly-N-Me-Val-Tyr(3-tBu)-NH$_2$ in the amount of 139 mg (83%).

To a solution of 130 mg (0.223 mmol) of Boc-N-phenyl-Gly-N-Me-Val-Tyr(3-tBu)-NH$_2$ in methylene chloride (1 ml), TFA (1 ml) was added and the resulting mixture was stirred at room temperature for 1 hour. The reaction mixture was concentrated under reduced pressure and the resulting residue was dissolved in methylene chloride, followed by successive washing with saturated aqueous NaHCO$_3$ and saturated brine. The organic layer was dried with magnesium sulfate and concentrated under reduced pressure; the resulting residue was subjected to silica gel column chromatography (eluting solvent consisting of chloroform, methanol and aqueous ammonia at a ratio of 10:1:0.1) to yield N-phenyl-Gly-N-Me-Val-Tyr(3-tBu)-NH$_2$ in the amount of 69.7 mg (65%).

FAB-MS: 483(M+H$^+$); NMR(method g,CDCl$_3$): δ 0.78 (3H,d,J=6.6 Hz), 0.94(3H,d,J=6.3 Hz), 1.35(9H,s), 2.16–2.36(1H,m), 2.66(3H,s), 2.78(1H,dd,J=10.2,14.2 Hz), 3.13(1H,dd,J=5.5,14.2 Hz), 3.42(1H,d,J=16.5 Hz), 3.74(1H, d,J=16.5 Hz), 4.48–4.64(2H,m), 4.86(1H,brs), 5.39(1H,brs), 6.07(1H,brs), 6.27(1H,d,J=8.3 Hz), 6.34(1H,d,J=7.2 Hz), 6.67(2H,d,J=8.3 Hz), 6.74–6.84(1H,m), 7.05(1H,s), 7.24–7.30(1H,m).

Example 114

N-Me-N-phenyl-Gly-N-Me-val-Tyr(3-tBu)-NH$_2$

To a solution of 184 mg (0.646 mmol) of Z-N-phenyl-Gly in THF (2 ml), 0.071 mg (0.65 mmol) of NMM, 0.084 ml (0.65 mmol) of isobutyl chloroformate, a solution of 150 mg (0.430 mmol) of N-Me-Val-Tyr(3-tBu)-NH$_2$ in DMF (2 ml) and 0.090 ml (0.65 mmol) of triethylamine were added under cooling with ice and the resulting mixture was stirred at room temperature for 3 hours. The reaction mixture was diluted with ethyl acetate and washed successively with saturated aqueous NaHCO$_3$, water and saturated brine. The organic layer was dried with magnesium sulfate and the solvent was distilled off under reduced pressure; the resulting residue was subjected to silica gel column chromatography (eluting solvent; ethyl acetate:n-hexane=2:1) to give Z-N-(phenyl)-Gly-N-Me-Val-Tyr(3-tBu)-NH$_2$ in the amount of 186 mg (70%).

To a solution of 180 mg (0.292 mmol) of Z-N-phenyl-Gly-N-Me-Val-Tyr(3-tBu)-NH$_2$ in methanol (2 ml), 10% palladium carbon (100 mg) was added and the mixture was stirred overnight in a hydrogen atmosphere at room temperature. To the reaction mixture, 0.50 ml (5.83 mmol) of 35% formaldehyde was added and the mixture was stirred for additional 3 hours in a hydrogen atmosphere at room temperature. After filtering, water was added to the filtrate and the mixture was extracted with chloroform and washed with saturated brine. The organic layer was dried with magnesium sulfate and concentrated under reduced pressure; the resulting residue was subjected to silica gel column chromatography (eluting solvent; ethyl acetate:n-hexane= 2:1) to yield N-Me-N-phenyl-Gly-N-Me-Val-Tyr(3-tBu)-NH$_2$ in 32.0 mg (22%).

FAB-MS: 497(M+H$^+$); NMR(method g,CDCl$_3$): δ 0.78 (3H,d,J=6.9 Hz), 0.88(3H,d,J=6.3 Hz), 1.37(9H,s), 2.18–2.36(1H,m), 2.63(1H,d,J=4.6 Hz), 2.84(3H,s), 2.88–2.96(1H,m), 2.99(3H,s), 3.92(1H,d,J=16.5 Hz), 4.06 (1H,d,J=16.5 Hz), 4.12(1H,d,J=7.3 Hz), 4.62(1H,dd,J=6.6, 7.9 Hz), 5.35(2H,brs), 5.92(1H,brs), 6.56(1H,d,J=7.9 Hz), 6.64(2H,d,J=7.9 Hz), 6.74(1H,t,J=7.9 Hz), 6.82(1H,d,7.9 Hz), 7.08(1H,s), 7.21(2H,t,J=7.9 Hz), 7.35(1H,d,J=4.0 Hz).

Example 115

N-(3-phenylbutyl)-Val-Tyr(3-tBu)-NH$_2$

To a solution of 330 mg (0.985 mmol) of Val-Tyr(3-tBu)-NH$_2$ and 146 mg (0.986 mmol) of 3-phenylbutylaldehyde in MeCN (2 ml), 0.1 ml of acetic acid and 124 mg (1.97 mmol) of sodium cyanoborohydride were added under cooling with ice and the resulting mixture was stirred at room temperature for 3 hours. Water was added to the reaction mixture, which was extracted with ethyl acetate and washed with saturated brine. The organic layer was dried with magnesium sulfate and concentrated under reduced pressure; the resulting residue was subjected to silica gel column chromatography (eluting solvent; chloroform:methanol=10:1) to yield N-(3-phenylbutyl)-Val-Tyr(3-tBu)-NH$_2$ in the amount of 236 mg (51%).

FAB-MS: 468(M+H$^+$); NMR(method g,CDCl$_3$): δ 0.57 (4/3H,d,J=6.9 Hz), 0.62(5/3H,d,J=6.9 Hz), 0.75(4/3H,d,J= 6.6 Hz), 0.62(5/3H,d,J=6.6 Hz), 1.23(3H,d,J=6.9 Hz), 1.38 (9H,s), 1.56–1.76(2H,m), 1.86–2.02(1H,m), 2.20–2.32(1H, m), 2.36(4/9H,d,J=6.9 Hz), 2.39(5/9H,d,J=6.9 Hz), 2.64–2.74(1H,m), 2.76(1H,d,J=4.3 Hz), 2.94–3.08(2H,m), 4.50–4.64(1H,m), 5.10–5.28(1H,m), 5.88(5/9H,brs), 6.00(4/ 9H,brs), 6.59(1H,d,J=7.9 Hz), 6.93(1H,d,J=7.9 Hz), 7.06 (1H,s), 7.10–7.36(5H,m), 7.64–7.76(1H,m).

Example 116

N-(2-amino-3-phenylpropyl)-Val-Tyr(3-tBu)-NH$_2$

To a solution of 106 mg (0.316 mmol) of Val-Tyr(3-tBu)-NH$_2$ and 90.0 mg (0.318 mmol) of Z-phenylalaninal in THF (2 ml), 300 mg of magnesium sulfate and 40.0 mg (0.637 mmol) of sodium cyanoborohydride were added under cooling with ice and the resulting mixture was stirred at room temperature for 2 hours. After filtering, water was added to the filtrate, which was extracted with chloroform and washed with saturated brine. The organic layer was dried with magnesium sulfate and concentrated under reduced pressure; the resulting residue was subjected to silica gel column chromatography (eluting solvent; chloroform:methanol=20:1) to give N-[2-benzoxycarbonylamino)-3-phenylpropyl]-Val-Tyr(3-tBu)-NH$_2$ in the amount of 95.7 mg (50%).

To a solution of 94.1 mg (0.156 mmol) of N-[2-(benzoxycarbonylamino)-3-phenylpropyl]-Val-Tyr(3-tBu)-NH$_2$ in methanol (2 ml), palladium carbon (50.0 mg) was added and the mixture was stirred overnight in a hydrogen atmosphere at room temperature. After filtering, the filtrate was concentrated under reduced pressure and the resulting residue was subjected to silica gel column chromatography (eluting solvent consisting of chloroform, methanol and aqueous ammonia at a ratio of 10:1:0.1) to yield N-(2-amino-3-phenylpropyl)-Val-Tyr(3-tBu)-NH$_2$ in the amount of 47.0 mg (64%).

FAB-MS: 469(M+H$^+$); NMR(method g,CDCl$_3$): δ 0.75 (3H,d,J=6.9 Hz), 0.87(3H,d,J=6.9 Hz), 1.38(9H,s), 1.90–2.08(1H,m), 2.38–2.54(3H,m), 2.66–2.78(1H,m), 2.81 (1H,d,J=4.6 Hz), 2.92–3.08(2H,m), 4.60–4.72(1H,m), 5.20–5.36(1H,m), 6.55(1H,brs), 6.61(1H,d,J=7.9 Hz), 6.92 (1H,d,J=7.9 Hz), 7.07(1H,s), 7.13(2H,d,J=6.9 Hz), 7.16–7.36(3H,m), 7.74(1H,d,J=8.2 Hz).

Example 117

2-[(2-amino-3-phenylpropyl)amino]-N-[2-amino-1-[( 3-tert-butyl-4-hydroxyphenyl)methyl]ethyl]-3-methyl butanamide (1) Synthesis of N-[2-(benzoxycarbonylamino)-1-[(3-tert-butyl-4-hydroxyphenyl)methyl]ethyl]-2-(tert-butoxycarbonylamino)-3-methyl butanamide To a solution of 2.00 g (7.97 mmol) of Tyr(3-tBu)-OMe in a mixture of 1,4-dioxane (15 ml) and water (15 ml), 929 mg (8.76 mmol) of sodium carbonate and 1.91 g (8.75 mmol) of di-tert-butyl dicarbonate were added under cooling with ice and the resulting mixture was stirred for 2 hours. Under cooling with ice, saturated aqueous NH$_4$Cl was added and the mixture was extracted with chloroform and washed with saturated brine. The organic layer was dried with magnesium sulfate and the solvent was distilled off under reduced pressure; the resulting residue was dissolved in a mixture of ethanol (20 ml) and THF (20 ml); under cooling with ice, 520 mg (23.9 mmol) of lithium borohydride was added to the solution and the mixture was stirred for 4 hours. To the reaction mixture, 2 N aqueous HCl was added, followed by extraction with chloroform and washing with water and saturated brine. The organic layer was dried with magnesium sulfate and concentrated under reduced pressure; the resulting residue was subjected to silica gel column chromatography (eluting solvent; ethyl acetate:n-hexane= 1:1) to give [1-[(3-tert-butyl-4-hydroxyphenyl)methyl]-2-hydroxyethyl]carbamic acid tert-butyl ester in the amount of 2.26 g (88%).

To a solution of 2.26 g (7.00 mmol) of the [1-[(3-tert-butyl-4-hydroxyphenyl)methyl]-2-hydroxyethyl]carbamic acid tert-butyl ester in THF (25 ml), 3.67 g (14.0 mmol) of triphenylphosphine, 2.06 g (14.0 mmol) of phthalimide and 2.76 ml (14.0 mmol) of diiosopropyl azodicarboxylate were added under cooling with ice and the resulting mixture was stirred for 1 hour. After adding water, the reaction mixture was extracted with ethyl acetate and washed with saturated brine. The organic layer was dried with magnesium sulfate and concentrated under reduced pressure; the resulting residue was subjected to silica gel column chromatography (eluting solvent; ethyl acetate:n-hexane=1:2) to give a mixture containing [1-[(3-tert-butyl-4-hydroxyphenyl)methyl]-2-(1,3-dioxo-1,3-dihydroisoindol-2-yl)ethyl]carbamic acid tert-butyl ester.

To a solution in methanol (15 ml) of the mixture containing [1-[(3-tert-butyl-4-hydroxyphenyl)methyl]-2-(1,3-dioxo-1,3-dihydroisoindol-2-yl)ethyl]carbamic acid tert-butyl ester, hydrazine monohydrate (2 ml) was added and the resulting mixture was stirred at room temperature for 4 hours. After filtering, the filtrate was concentrated under reduced pressure and the resulting residue was subjected to silica gel column chromatography (eluting solvent consisting of chloroform, methanol and aqueous ammonia at a ratio of 10:1:0.1) to give [2-amino-1-[(3-tert-butyl-4-hydroxyphenyl)methyl]ethyl]carbamic acid tert-butyl ester in the amount of 1.55 g (69%).

To a solution of 1.53 g (4.75 mmol) of [2-amino-1-[(3-tert-butyl-4-hydroxyphenyl)methyl]ethyl]carbamic acid tert-butyl ester in methylene chloride (20 ml), 0.725 ml (5.23 mmol) of triethylamine and 0.746 ml (5.23 mmol) of benzyl chloroformate were added and the resulting mixture was stirred for 15 minutes. Under cooling with ice, saturated aqueous NaHCO$_3$ was added and the mixture was extracted with methylene chloride and washed with saturated brine. The organic layer was dried with magnesium sulfate and concentrated under reduced pressure; the resulting residue was subjected to silica gel column chromatography (eluting solvent; ethyl acetate:n-hexane=1:1) to give [2-(benzoxycarbonylamino)-1-[(3-tert-butyl-4-hydroxyphenyl) methyl]ethyl]carbamic acid tert-butyl ester in the amount of 1.78 g (82%).

NMR(method g,CDCl$_3$): δ 1.39(9H,s), 1.40(9H,s), 2.60–2.80(2H,m), 3.08–3.38(2H,m), 3.80–3.94(1H,m), 4.58–4.72(1H,m), 5.10(2H,s), 5.28(1H,brs), 6.59(1H,d,J= 7.9 Hz), 6.85(1H,d,J=7.9 Hz), 7.02(1H,s), 7.34(5H,brs).

To a solution of 402 mg (0.882 mmol) of [2-(benzoxycarbonylamino)-1-[(3-tert-butyl-4-hydroxyphenyl)-methyl]ethyl]carbamic acid tert-butyl ester in methylene chloride (2 ml), TFA (2 ml) was added and the mixture was stirred at room temperature for 30 minutes. The reaction mixture was distilled off under reduced pressure and the resulting residue was dissolved in DMF (3 ml); to the solution, 287 mg (1.32 mmol) of Boc-Val, 179 mg (1.32 mmol) of HOBT, 162 mg (1.33 mmol) of DMAP and 254 mg (1.32 mmol) of WSCI.HCl were added and the resulting mixture was stirred at room temperature for 4 hours. The reaction mixture was diluted with ethyl acetate and washed successively with saturated aqueous NaHCO$_3$, water and saturated brine. The organic layer was dried with magnesium sulfate and concentrated under reduced pressure; the resulting residue was subjected to silica gel column chromatography (eluting solvent; ethyl acetate:n-hexane=1:1) to give N-[2-(benzoxycarbonylamino)-1-[(3-tert-butyl-4-hydroxyphenylmethyl]ethyl]-2-(tertbutoxycarbonylamino)-3-methyl butanamide in 363 mg (74%).

(2) Synthesis of 2-[(2-amino-3-phenylpropyl)amino]-N-[2-amino-1-[(3-tert-butyl-4-hydroxyphenyl)methyl]ethyl]-3-methyl butanamide.

To a solution of 436 mg (0.786 mmol) of N-[2-(benzoxycarbonylamino)-1-[(3-tert-butyl-4-hydroxyphenyl) methyl]ethyl]-2-(tert-butoxycarbonylamino)-3-methyl butanamide in methylene chloride (2 ml), TFA (2 ml) was added and the mixture was stirred at room temperature for 30 minutes. The reaction mixture was concentrated under reduced pressure and to the residue, saturated aqueous NaHCO$_3$ was added under cooling with ice and the mixture was extracted with chloroform and washed with saturated brine. The organic layer was dried with magnesium sulfate and the solvent was distilled off under reduced pressure; the resulting residue was dissolved in MeCN (3 ml) and under cooling with ice, 245 mg (0.866 mmol) of Z-phenylalaninal, 0.1 ml of acetic acid and 98.8 mg (1.57 mmol) of sodium cyanoborohydride were added to the solution, which was then stirred for 3 hours. After adding water, the solution was extracted with chloroform and washed with saturated brine. The organic layer was dried with magnesium sulfate and concentrated under reduced pressure; the resulting residue was subjected to silica gel column chromatography (eluting solvent; ethyl acetate:n-hexane=1:1) to give N-[2-benzoxycarbonylamino-1-[(3-tert-butyl-4-hydroxyphenyl)methyl]ethyl]-2-[[2-(benzoxycarbonylamino)-3-phenylpropyl]-amino]-3-methyl butanamide in the amount of 282 mg (50%).

To a solution of 132 mg (0.183 mmol) of N-[2-benzoxycarbonylamino-1-[(3-tert-butyl-4-hydroxyphenyl)methyl]ethyl]-2-[[2-(benzoxycarbonylamino)-3-phenylpropyl]amino]-3-methyl butanamide in methanol (2 ml), 10% palladium carbon (80 mg) was added and the mixture was stirred in a hydrogen atmosphere at room temperature for 2 days. After filtering, the filtrate was concentrated under reduced pressure and the resulting residue was subjected to silica gel column chromatography (eluting solvent consisting of chloroform, methanol and aqueous ammonia at a ratio of 10:1:0.1) to yield 2-[(2-amino-3-phenylpropyl)amino]-N-[2-amino-1-[(3-tert-butyl-4-hydroxyphenyl)methyl]ethyl]-3-methyl butanamide in the amount of 24.2 mg (29%).

FAB-MS: 455(M+H$^+$); NMR(method g,CDCl$_3$): δ 0.70 (3H,dd,J=2.0,6.6 Hz), 0.84(3H,d,J=6.9 Hz), 1.37(9H,s), 1.98–2.04(1H,m), 2.24–2.86(9H,m), 2.94–3.12(1H,m), 4.10–4.26(1H,m), 6.62(1H,d,J=7.9 Hz), 6.87(1H,d,J=7.9 Hz), 7.00(1H,s), 7.12–7.34(5H,m).

Example 118

N-[2-(3-tert-butyl-4-hydroxyphenyl)-1-methylethyl]-3-methyl-2-(N-methyl-N-phenylalanylamino) butanamide (1) Synthesis of Z-N,O-dibenzyl-Tyr(3-tBu)-OMe To a solution of 3.0 g (7.78 mmol) of Z-Tyr(3-tBu)-OMe in DMF (20 ml), 0.68 g (17.1 mmol) of sodium hydride was added under cooling with ice and the mixture was stirred for 15 minutes; thereafter, 2.3 ml (19.5 mmol) of benzyl bromide was added. After stirring for additional 3 hours, saturated aqueous NaHCO$_3$ was added to the reaction mixture, which was extracted with ethyl acetate and washed with water and saturated brine. The organic layer was dried with anhydrous magnesium sulfate and concentrated under reduced pressure; the resulting residue was subjected to silica gel column chromatography (eluting solvent; ethyl acetate:n-hexane=1:5) to give Z-N,O-dibenzyl-Tyr(3-tBu)-OMe in 4.14 g (94%).

(2) Synthesis of N-benzyl-2-(4-benzyloxy-3-tert-butylphenyl)-1-methyl-N-(benzyloxycarbonyl)ethylamine To a solution of 4.14 g (7.32 mmol) of Z-N,O-dibenzyl-Tyr(3-tBu)-OMe in a mixture of ethanol (36 ml) and THF (6 ml), 11.0 ml (22.0 mmol) of a solution of 2 M lithium borohydride in THF was added under cooling with ice and the resulting mixture was stirred overnight at room temperature. After adding water, the reaction mixture was extracted with ethyl acetate, washed with saturated brine, dried with anhydrous magnesium sulfate and the solvent was distilled off under reduced pressure. The resulting residue was dissolved in methylene chloride (50 ml) and under cooling with ice, 2.0 ml (14.4 ml) of triethylamine and 0.72 ml (9.36 mmol) of methanesulfonyl chloride were added in succession and the resulting mixture was stirred for 30 minutes. The reaction mixture was washed with saturated aqueous NaHCO$_3$ and the organic layer was dried with anhydrous magnesium sulfate and the solvent was distilled off under reduced pressure; there-after, the resulting residue was dissolved in THF (10 ml) and 28.0 ml (28.0 mmol) of a solution of 1 M lithium triethylborohydride in THF was added. After stirring the mixture for 3 hours, water was added under cooling with ice and extraction was effected with methylene chloride. The organic layer was dried with anhydrous magnesium sulfate and concentrated under reduced pressure; the resulting residue was subjected to silica gel column chromatography (eluting solvent; ethyl acetate:n-hexane=1:5) to give N-benzyl-2-(4-benzyloxy-3-tert-butylphenyl)-1-methyl-N-(benzyloxycarbonyl)ethylamine in the amount of 2.35 g (61%).

(3) Synthesis of 2-(3-tert-butyl-4-hydroxyphenyl)-1-methylethylamine

A suspension of 2.35 g (4.50 mmol) of N-benzyl-2-(4-benzyloxy-3-tert-butylphenyl)-1-methyl-N-(benzyloxycarbonyl)ethylamine and 0.50 g of a 20% palladium hydride on carbon catalyst in methanol (30 ml) was stirred overnight in a hydrogen atmosphere. After filtering off the catalyst, the solvent was distilled off under reduced pressure to give 2-(3-tert-butyl-4-hydroxyphenyl)-1-methylethylamine in the amount of 0.90 g (96%).

NMR(method g,CDCl$_3$): δ 1.16(3H,d,J=6.6 Hz), 1.39(9H, s), 2.45(1H,dd,J=4.9,13.3 Hz), 2.69(1H,dd,J=4.9,13.3 Hz), 3.15(1H,m), 3.5(2H,brs), 6.58(1H,d,J=7.9 Hz), 6.83(1H,dd, J=1.6,7.9 Hz), 7.03(1H,d,J=1.6 Hz).

(4) Synthesis of N-[2-(3-tert-butyl-4-hydroxyphenyl)-1-methylethyl]-3-methyl-2-(methylamino)butanamide To a solution of 0.31 g (1.50 mmol) of 2-(3-tert-butyl-4-hydroxyphenyl)-1-methylethylamine, 0.40 g (1.50 mmol) of Z-N-Me-Val-OH and 0.30 g (2.25 mmol) of HOBT in DMF (5 ml), 0.35 ml (2.25 mmol) of DIC was added under cooling with ice. After being stirred at room temperature for 2 hours, the reaction mixture was diluted with ethyl acetate and washed successively with saturated aqueous NaHCO$_3$, water and saturated brine. The organic layer was dried with anhydrous magnesium sulfate and concentrated under reduced pressure; the resulting residue was subjected to silica gel column chromatography (eluting solvent; chloroform:methanol=125:1) to give 2-[N-(benzyloxycarbonyl)-N-methylamino]-N-[2-(3-tert-butyl-4-hydroxyphenyl)-1-methylethyl]-3-methylbutanamide in the amount of 0.55 g (81%).

A suspension of 0.54 g (1.19 mmol) of 2-[N-(benzyloxycarbonyl)-N-methylamino]-N-[2-(3-tert-butyl-4-hydroxyphenyl)-1-methylethyl]-3-methylbutanamide and 0.10 g of a 20% palladium hydroxide on carbon catalyst in methanol (8 ml) was stirred in a hydrogen atmosphere for 2 hours. After filtering off the catalyst, the solvent was distilled off under reduced pressure to give N-[2-(3-tert-butyl-4-hydroxyphenyl)-1-methylethyl]-3-methyl-2-(methylamino) butanamide in the amount of 0.36 g (95%).

(5) N-[2-(3-tert-butyl-4-hydroxyphenyl)-1-methylethyl]-3-methyl-2-(N-methyl-N-phenylalanylamino)butanamide To a solution of 0.36 g (1.12 mmol) of N-[2-(3-tert-butyl-4-hydroxyphenyl)-1-methylethyl]-3-methyl-2-(methylamino)butanamide, 0.75 g (2.81 mmol) of Boc-Phe-OH and 0.38 g (2.81 mmol) of HOBT in DMF (5 ml), 0.44 ml (2.81 mmol) of DIC was added under cooling with ice. After being stirred at room temperature for 2.5 days, the reaction mixture was diluted with ethyl acetate and washed successively with saturated aqueous NaHCO$_3$, water and saturated brine. The organic layer was dried with anhydrous magnesium sulfate and concentrated under reduced pressure; the resulting residue was subjected to silica gel column chromatography (eluting solvent; chloroform:methanol= 80:1) to give N-[2-(3-tert-butyl-4-hydroxyphenyl)-1-methylethyl]-2-[N-(N-Boc-phenyl-alanyl)-N-methylamino]-3-methylbutanamide in 333 mg (52%).

The N-[2-(3-tert-butyl-4-hydroxyphenyl)-1-methylethyl]-2-[N-(N-Boc-phenylalanyl)-N-methylamino]-3-methylbutanamide (333 mg) was dissolved in methylene chloride (4 ml) and, after adding TFA (2 ml), the solution was stirred at room temperature for 10 minutes. The solvent was distilled off under reduced pressure and the resulting residue was diluted with methylene chloride and washed with saturated aqueous NaHCO$_3$. The resulting organic layer was concentrated under reduced pressure and the residue was subjected to silica gel column chromatography (eluting solvent consisting of chloroform, methanol and aqueous ammonia at a ratio of 75:1:0.1) to yield N-[2-(3-tert-butyl-4-hydroxyphenyl)-1-methylethyl]-3-methyl-2-(N-methyl-N-phenylalanylamino)butanamide in the amount of 164 mg (60%).

EI-MS: 468(M$^+$+1); NMR(method g,CDCl$_3$): δ 0.72(3/2H,d,J=6.6 Hz), 0.81(3/2H,d,J=6.6 Hz), 0.93(3/2H,d,J=6.6 Hz), 0.94(3/2H,d,J=6.3 Hz), 1.07(3/2H,d,J=6.6 Hz), 1.08(3/2H,d,J=6.6 Hz), 1.37(4H,s), 1.40(5H,s), 2.23–2.42(1H,m), 2.43–2.90(3H,m), 2.75(5/3H,s), 2.84(4/3H,s), 3.19(1/2H,dd,J=4.3,13.8 Hz), 3.62(1/2H,m), 3.82–3.88(1H,m), 4.23(1H,m), 4.47(2/5H,d,J=10.9 Hz), 6.00(3/5H,d,J=8.2 Hz), 6.61(2/5H,d,J=7.9 Hz), 6.66(3/5H,dd,J=2.0,7.9 Hz), 6.77(3/5H,d,J=7.9 Hz), 6.83(2/5H,dd,J=2.0,7.9 Hz), 6.99(3/5H,d,J=2.0 Hz), 7.05(2/5H,d,J=2.0 Hz), 7.1–7.4(7H,m), 8.22(3/5H,d,J=8.3 Hz).

Example 119

Phe-N-Me-Val-N-Me-Tyr(3-tBu)-NH$_2$ (1) Synthesis of Z-N-Me-Val-N-Me-Tyr(3-tBu)-OMe To a solution of 3.25 g of Z-N-Me-Val-OH, 2.2 g of N-Me-Tyr(3-tBu)-OMe and 1.88 g of HOBT in DMF (30 ml), DIC (1.9 ml) was added under cooling with ice and the mixture was stirred at room temperature for 23 hours. Water was added to the reaction mixture and extraction was effected with ether. The extract was washed with saturated brine and the organic layer was dried with sodium sulfate. After distilling off the solvent under reduced pressure, the resulting residue was subjected to silica gel column chromatography (eluting solvent consisting of chloroform, methanol and aqueous ammonia at a ratio of 100:10:1) to give Z-N-Me-Val-N-Me-Tyr(3-tBu)-OMe in the amount of 1.96 g (47%).

(2) Synthesis of Z-N-Me-Val-N-Me-Tyr(3-tBu)-NH$_2$

To a solution of 1.96 g of Z-N-Me-Val-N-Me-Tyr(3-tBu)-OMe in 1,4-dioxane (40 ml), 2 N NaOH (5 ml) was added at room temperature and the mixture was stirred for 2 hours. The reaction mixture was adjusted to pH 3 with dilute hydrochloric acid and extracted with ethyl acetate. The extract was washed with saturated brine and the organic layer was dried with sodium sulfate. The solvent was distilled off under reduced pressure to give Z-N-Me-Val-N-Me-Tyr(3-tBu)-OH. To a solution of this Z-N-Me-Val-N-Me-Tyr(3-tBu)-OH in THF (20 ml), ethyl chloroformate (0.40 ml) and NMM (0.46 ml) were added under cooling with ice and the mixture was stirred for 15 minutes. Subsequently, ammonia gas was bubbled into the reaction mixture for 5 minutes. The solvent was distilled off under reduced pressure and the precipitating salt was filtered off and washed with ethyl acetate. The solvent was distilled off under reduced pressure and the resulting residue was subjected to silica gel column chromatography (eluting solvent; n-hexane:ethyl acetate=2:3) to give Z-N-Me-Val-N-Me-Tyr(3-tBu)-NH$_2$ in the amount of 1.17 g (61%).

(3) Synthesis of N-Me-Val-N-Me-Tyr(3-tBu)-NH$_2$

A mixture of Z-N-Me-Val-N-Me-Tyr(3-tBu)-NH$_2$ (1.17 g) and 20% palladium hydroxide on carbon (0.24 g) in methanol (20 ml) was stirred at room temperature in a hydrogen atmosphere for 1 hour. The reaction mixture was filtered and washed with methanol. The solvent was distilled off under reduced pressure and the resulting residue was subjected to silica gel column chromatography (eluting solvent consisting of chloroform, methanol and aqueous ammonia at a ratio of 100:10:1) to give N-Me-Val-N-Me-Tyr(3-tBu)-NH$_2$ in the amount of 609 mg (71%).

(4) Synthesis of Z-Phe-N-Me-Val-N-Me-Tyr(3-tBu)-NH$_2$

To a solution of Z-Phe-OH (742 mg) in THF (3 ml), isobutyl chloroformate (0.32 ml) and NMM (0.27 ml) were added under cooling with ice and the mixture was stirred for 15 minutes. Subsequently, a solution of N-Me-Val-N-Me-Tyr(3-tBu)-NH$_2$ (600 mg) in THF (3 ml) was added and the mixture was stirred at room temperature for 10 hours. Water was added to the reaction mixture and extraction was effected with ethyl acetate. The extract was washed with saturated brine, dried with sodium sulfate, and concentrated under reduced pressure. The resulting residue was subjected to silica gel column chromatography (eluting solvent; n-hexane:acetone=3:2) to give Z-Phe-N-Me-Val-N-Me-Tyr(3-tBu)-NH$_2$ in the amount of 611 mg (58%).

(5) Synthesis of Phe-N-Me-Val-N-Me-Tyr(3-tBu)-NH$_2$

A mixture of Z-Phe-N-Me-Val-N-Me-Tyr(3-tBu)-NH$_2$ (610 mg) and 10% palladium carbon (100 mg) in methanol (15 ml) was stirred at room temperature in a hydrogen atmosphere for 17 hours. The reaction mixture was filtered and washed with methanol. The solvent was distilled off under reduced pressure and the resulting residue was subjected to silica gel column chromatography (eluting solvent; ethyl acetate) to yield Phe-N-Me-Val-N-Me-Tyr(3-tBu)-NH$_2$ in the amount of 431 mg (89%).

EI-MS: 511(M$^+$+1); NMR(method g,CDCl$_3$): δ 0.50(9/10H,d,J=6.3 Hz), 0.75(9/10H,d,J=6.6 Hz), 0.79(21/10H,d,J=6.9 Hz), 0.93(21/10H,d,J=6.6 Hz), 1.34(63/10H,s), 1.39(27/10H,s), 2.15–2.99(46/10H,m), 2.46(21/10H,s), 2.78(21/10H,s), 3.02(9/10H,s), 3.03(9/10H,s), 3.15(7/10H,dd,J=14.9,5.9 Hz), 3.33(3/10H,dd,J=13.9,6.9 Hz), 3.72(7/10H,dd,J=8.9,5.0 Hz), 3.91(3/10H,dd,J=8.1,5.1 Hz), 4.92(3/10H,d,J=10.9 Hz), 5.02–5.09(14/10H,m), 5.29(7/10H,brs), 5.49(7/10H,dd,J=10.7,5.8 Hz), 5.98(7/10H,brs), 6.32(7/10H,d,J=7.9 Hz), 6.60–6.67(6/10H,m), 6.72(7/10H,dd,J=7.9,2.0 Hz), 6.97(3/10H,dd,J=7.9,2.0 Hz), 7.10–7.39(67/10H,m).

Example 120

N-[2-(3-tert-butyl-4-hydroxyphenyl)-1-methylethyl]-3-methyl-2-[N-methyl-N-(N-Me-phenylalanyl)amino]butanamide To a solution of 115 mg (0.359 mmol) of N-[2-(3-tert-butyl-4-hydroxyphenyl)-1-methylethyl]-3-methyl-2-(methylamino)butanamide and 170 mg (0.610 mmol) of Boc-N-Me-Phe-OH in methylene chloride (1.5 ml), 318 mg (0.718 mmol) of BOP and 0.10 ml (0.718 mmol) of TEA were added in succession under cooling with ice. After being stirred at room temperature for 2 days, the reaction mixture was diluted with methylene chloride and washed with water. The organic layer was dried with anhydrous magnesium sulfate and the solvent was distilled off under reduced pressure; the resulting residue was subjected to silica gel column chromatography (eluting solvent; chloroform:methanol=150:1) to give N-[2-(3-tert-butyl-4-hydroxyphenyl)-1-methylethyl]-2-[N-(N-Boc-N-Me-phenylalanyl)-N-methylamino]- 3-methylbutanamide in the amount of 149 mg (71%).

A portion (145 mg) of the N-[2-(3-tert-butyl-4-hydroxyphenyl)-1-methylethyl]-2-[N-(N-Boc-N-Me-phenylalanyl)-N-methylamino]-3-methylbutanamide was dissolved in methylene chloride (2 ml) and, after adding TFA (1 ml), the solution was stirred at room temperature for 15 minutes. The solvent was distilled off under reduced pressure and the resulting residue was diluted with methylene chloride and washed with saturated aqueous $NaHCO_3$. The organic layer was concentrated under reduced pressure and the resulting residue was subjected to silica gel column chromatography (eluting solvent consisting of chloroform, methanol and aqueous ammonia at a ratio of 80:1:0.1) to yield N-[2-(3-tert-butyl-4-hydroxyphenyl)-1-methylethyl]-3-methyl-2-[N-methyl-N-(N-Me-phenylalanyl)amino] butanamide in the amount of 86 mg (72%).

EI-MS: 481($M^+$); NMR(method g,$CDCl_3$): δ 0.52(1H,d,J=6.6 Hz), 0.78(2H,d,J=6.6 Hz), 0.93(3H,d,J=6.3 Hz), 1.08 (1H,d,J=6.6 Hz), 1.13(2H,d,J=6.6 Hz), 1.36(5H,s), 1.39(4H, s), 2.1–2.3(1H,m), 2.25(2H,s), 2.32(1H,s), 2.5–2.9(3H,m), 2.59(2H,s), 2.62(1H,s), 3.08(1/2H,d,J=6.6 Hz), 3.58(1/2H, t,J=6.3 Hz), 3.65–3.73(1/2H,m), 4.07–4.25(3/5H,m), 4.46 (2/5H,d,J=11.2 Hz), 5.62(1/2H,brs), 6.06(1/2H,d,J=8.3 Hz), 6.59–6.64(1H,m), 6.75–6.94(1H,m), 7.01–7.12(1H,m), 7.2–7.4(6H,m), 8.18(1/2H,d,J=8.3 Hz).

Example 121

N-[2-(3-tert-butyl-4-hydroxyphenyl)-1-methylethyl]-N-Me- 3-methyl-2-(N-methyl-N-phenylalanylamino)butanamide (1) Synthesis of 2-(4-benzyloxy-3-tert-butylphenyl)-N-(benzyloxycarbonyl)-N-Me-1-methylethylamine To a solution in ethanol (18 ml) and THF (3 ml) of 1.60 g (3.27 mmol) of Z-N-Me-Phe(3-tBu-4-benzyloxy)-OMe prepared in accordance with Example 91, 4.9 ml (9.80 mmol) of a solution of 2 M lithium borohydride in THF was added under cooling with ice and the mixture was stirred overnight at room temperature. After addition of water, the reaction mixture was extracted with ethyl acetate and the extract was washed with saturated brine, dried with anhydrous magnesium sulfate, and the solvent was distilled off under reduced pressure. The resulting residue was dissolved in methylene chloride (15 ml); after adding 0.88 ml (6.32 mmol) of triethylamine and 0.27 ml (3.47 mmol) of methanesulfonyl chloride successively under cooling with ice, the solution was stirred for 30 minutes. The reaction mixture was washed with saturated aqueous $NaHCO_3$ and the organic layer was dried with anhydrous magnesium sulfate and concentrated under reduced pressure. The resulting residue was then subjected to silica gel column chromatography (eluting solvent; ethyl acetate:n-hexane=1:2) to give mesylate in the amount of 0.88 g (50% in two steps). To a solution of the mesylate (0.88 g, 1.62 mmol) in THF (5 ml), 5.8 ml (5.8 mmol) of a solution of 1 M lithium triethylborohydride in THF was added. After stirring for 1.5 hours, water was added to the reaction mixture under cooling with ice and it was then extracted with methylene chloride. The organic layer was dried with anhydrous magnesium sulfate and concentrated under reduced pressure; the resulting residue was subjected to silica gel column chromatography (eluting solvent; ethyl acetate:n-hexane=1:5) to give 2-(4-benzyloxy-3-tert-butyl-phenyl)-N-(benzyloxycarbonyl)-N-Me-1-methylethylamine in 0.50 g (68%).

(2) Synthesis of 2-(3-tert-butyl-4-hydroxyphenyl)-N-Me-1-methylethylamine

A suspension of 0.49 g (1.09 mmol) of 2-(4-benzyloxy-3-tert-butylphenyl)-N-(benzyloxycarbonyl)-N-Me-1-methylethylamine and 0.10 g of a 20% palladium hydroxide on carbon catalyst in methanol (5 ml) was stirred in a hydrogen atmosphere for 2.5 hours. After filtering off the catalyst, the solvent was distilled off under reduced pressure to give 2-(3-tert-butyl-4-hydroxyphenyl)-N-Me-1-methylethylamine in 0.23 g (96%).

NMR(method g,$CDCl_3$): δ 1.12(3H,d,J=6.3 Hz), 1.38(9H, s), 2.42(s, 3H), 2.64(2H,d,J=6.6 Hz), 2.75–2.90(1H,m), 6.55 (1H,d,J=7.9 Hz), 6.84(1H,dd,J=1.6,7.9 Hz), 7.04(1H,d,J= 1.6 Hz).

(3) Synthesis of N-[2-(3-tert-butyl-4-hydroxyphenyl)-1-methylethyl]-N-Me-3-methyl-2-methylaminobutanamide To a solution of 0.22 g (0.994 mmol) of 2-(3-tert-butyl-4-hydroxyphenyl)-N-Me-1-methylethylamine, 0.55 mg (2.09 mmol) of Z-N-Me-Val-OH and 0.30 g (1.99 mmol) of HOBT in DMF (3 ml), 0.31 ml (1.99 mmol) of DIC was added under cooling with ice. After being stirred at room temperature for 38 hours, the reaction mixture was diluted with ethyl acetate and washed with saturated aqueous $NaHCO_3$, water and saturated brine. The organic layer was dried with anhydrous magnesium sulfate and concentrated under reduced pressure. The resulting residue was subjected to silica gel column chromatography (eluting solvent; ethyl acetate:n-hexane=1:4) to give 2-[N-(benzyloxycarbonyl)-N-methylamino]-N-[2-(3-tert-butyl-4-hydroxyphenyl)-1-methylethyl]-N-Me-3-methylbutanamide in the amount of 155 mg (33%).

A solution of 150 mg (0.320 mmol) of 2-[N-(benzyloxycarbonyl)-N-methylamino]-N-[2-(3-tert-butyl-4-hydroxyphenyl)-1-methylethyl]-N-Me-3-methylbutanamide and 0.02 g of a 20% palladium hydroxide on carbon catalyst in methanol (2 ml) was stirred in a hydrogen atmosphere for 3 hours. After filtering off the catalyst, the solvent was distilled off under reduced pressure to give N-[2-(3-tert-butyl-4-hydroxyphenyl)-1-methylethyl]-N-Me-3-methyl-2-(methylamino)butanamide in the amount of 97 mg (92%).

(4) Synthesis of N-[2-(3-tert-butyl-4-hydroxyphenyl)-1-methylethyl]-N-Me-3-methyl-2-(N-methyl-N-phenylalanyl-amino)butanamide To a solution of 93 mg (0.278 mmol) of N-[2-(3-tert-butyl-4-hydroxyphenyl)-1-methylethyl]-N-Me-3-methyl-2-(methylamino)butanamide and 125 mg (0.473 mmol) of Boc-Phe-OH in methylene chloride (1.5 ml), 246 mg (0.556 mmol) of BOP and 0.077 ml (0.556 mmol) of TEA were successively added under cooling with ice. After being stirred at room temperature for 2.5 days, the reaction mixture was diluted with methylene chloride and washed with water. The organic layer was dried with anhydrous magnesium sulfate and concentrated under reduced pressure; the resulting residue was subjected to silica gel column chromatography (eluting solvent; chloroform:methanol=150:1) to give N-[2-(3-tert-butyl-4-hydroxyphenyl)-1-methylethyl]-2-[N-(N-Boc-phenylalanyl)-N-methylamino]-N-Me-3-methylbutanamide in the amount of 108 mg (67%).

The thus obtained N-[2-(3-tert-butyl-4-hydroxyphenyl)-1-methylethyl]-2-[N-(N-Boc-phenylalanyl)-N-methylamino]-N-Me-3-methylbutanamide (108 mg) was dissolved in methylene chloride (2 ml) and, after adding TFA (1 ml), the solution was stirred at room temperature for 15 minutes. The solvent was distilled off under reduced pressure and the resulting residue was diluted with methylene chloride and washed with saturated aqueous NaHCO$_3$. The organic layer was concentrated under reduced pressure and the resulting residue was subjected to silica gel column chromatography (eluting solvent consisting of chloroform, methanol and aqueous ammonia at a ratio of 60:1:0.1) to yield N-[2-(3-tert-butyl-4-hydroxyphenyl)-1-methylethyl]-N-Me-3-methyl-2-(N-methyl-N-phenylalanylamino) butanamide in the amount of 71 mg (80%).

EI-MS: 481(M$^+$); NMR(method g,CDCl$_3$): δ 0.41(3H,d, J=6.6 Hz), 0.74(3H,d,J=6.6 Hz), 1.08(3H,d,J=6.6 Hz), 1.36 (9H,s), 2.07–2.24(1H,m), 2.55–2.76(2H,m), 2.81(3H,s), 2.86–3.00(2H,m), 2.90(3H,s), 3.94(1H,t,J=6.6 Hz), 4.94 (1H,d,J=10.9 Hz), 5.02–5.11(1H,m), 6.61(1H,d,J=8.3 Hz), 6.89(1H,dd,J=2.0,7.9 Hz), 7.00(1H,d,J=1.7 Hz), 7.10–7.35 (6H,m).

Test 1
Motilin Receptor Binding Test

A motilin receptor binding test was conducted in the following manner [Bormans et al., Regul. Peptides, 15, 143 (1986)]. The duodenum was extracted from a slaughtered rabbit, had the mucous membrane separated and homogenized in 50 mM Tris-HCl buffer to prepare a receptor sample. The sample was incubated together with $^{125}$I motilin 25 pM and thereafter the radioactivity bound to the receptor was measured. Specific binding was defined as the difference between the radioactivity in the case of adding 1% DMSO in place of the compounds of the examples and that in the case of adding a great excess amount of motilin (10$^{-7}$ M). The activity of each compound was expressed by IC$_{50}$ (in nM), as the concentration sufficient to reduce the specific binding by 50%. The results are shown in Table C-1.

Test 2
Action on the Contraction of a Specimen of Longitudinal Muscle in the Duodenum Extracted from a Rabbit The action on the motilin-induced contraction of a specimen of longitudinal muscle in the duodenum extracted from a rabbit was investigated by the following method. A duodenum specimen extracted from a slaughtered rabbit (3×10 mm) was suspended in an organ bath (10 ml) such that the longitudinal muscle would run vertically; the bath was filled with a Krebs solution kept at 28° C. A mixed gas (95% O$_2$ and 5% CO$_2$) was continuously bubbled into the Krebs solution and the contraction of the duodenum specimen was recorded isotonically (with a 1-g load) via an isotonic transducer (TD-111T of Nihon Koden, K.K.) The degree of contraction was expressed in relative values, with the contraction by acetylcholine at a dose of 10$^{-4}$ M being taken as 100%. The activity of each compound was calculated as pA$_2$ value indicating its effect on the dose-dependent muscle contraction by the motilin put into the organ bath. The results are shown in Table C-1.

TABLE C-1

| Example No. | Motilin receptor binding test, IC$_{50}$ (nM) | Contraction suppressing test, pA$_2$ |
|---|---|---|
| 5 | 12 | 7.81 |
| 18B | 3.7 | 8.58 |
| 118 | 1.9 | 8.43 |
| 119 | 4.3 | 8.59 |

Industrial Applicability

The compounds of the invention typically function as a motilin receptor antagonist and are useful as medicines including therapeutics of irritable bowel syndrome.

What is claimed is:
1. A compound represented by formula (1), a hydrate thereof or a pharmaceutically acceptable salt thereof:

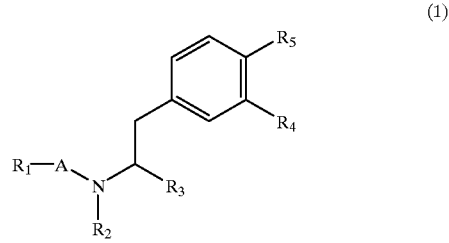

wherein A is an amino acid residue or an Nα-substituted amino acid residue, provided that A binds with —NR$_2$— to form an amide;

R$_1$ is R$_6$—CO—, an optionally substituted straight-chained or branched alkyl group having 2–7 carbon atoms, an optionally substituted straight-chained or branched alkenyl group having 3–8 carbon atoms, or an optionally substituted straight-chained or branched alkynyl group having 3–8 carbon atoms;

R$_2$ is a hydrogen atom or an optionally substituted straight-chained or branched alkyl group having 1–3 carbon atoms;

R$_3$ is —CO—R$_7$, an optionally substituted straight-chained or branched alkyl group having 1–5 carbon atoms, an optionally substituted straight-chained or branched alkenyl group having 2–5 carbon atoms or an optionally substituted straight-chained or branched alkynyl group having 2–5 carbon atoms;

R$_4$ is a straight-chained or branched alkyl group having 1–6 carbon atoms, a straight-chained or branches alkenyl group having 2–6 carbon atoms, a straight-chained or branched alkynyl group having 2–6 carbon atoms, or the formula (2):

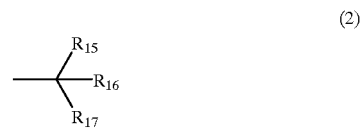

R$_5$ is a hydrogen atom or —OR$_8$;

R$_6$ is an optionally substituted straight-chained or branched alkyl group having 1–6 carbon atoms, an optionally substituted straight-chained or branched alkenyl group having 2–7 carbon atoms, an optionally substituted alkynyl group having 2–7 carbon atoms, a cycloalkyl group having 3–7 carbon atoms that may be fused to a benzene ring or a heterocyclic ring, an aromatic ring having 6–12 carbon atoms, and being optionally substituted with one or more substituents independently selected from the group consisting of a hydroxyl group, a methoxy group, a phenoxy group, a benzyloxy group,a tert-butyloxy group, an amino group, a methylamino group, a dimethylamino group, an ethylamino group, a carboxyl group, a methoxycarbonyl group and a phenyl group, an optionally substituted saturated or unsaturated heterocyclic ring having 3–12 carbon atoms, —N(R$_9$)R$_{10}$ or —OR$_{11}$;

R$_7$ is a hydrogen atom, an optionally substituted straight-chained or branched alkyl group having 1–5 carbon atoms, a cycloalkyl group having 3–7 carbon atoms, —N(R$_{12}$)R$_{13}$ or —OR$_{14}$;

$R_8$ is a hydrogen atom or a straight-chained alkyl group having 1–4 carbon atoms;

$R_9$ and $R_{10}$, which may be the same or different, each represent a hydrogen atom, an optionally substituted straight-chained or branched alkyl group having 1–5 carbon atoms, an optionally substituted straight-chained or branched alkenyl group having 2–6 carbon atoms, an optionally substituted straight-chained or branched alkynyl group having 2–6 carbon atoms, a cycloalkyl group having 3–6 carbon atoms that may be fused to a benzene ring or a heterocyclic ring, or an optionally substituted aromatic ring having 6–12 carbon atoms;

$R_{11}$ is an optionally substituted straight-chained or branched alkyl group having 1–5 carbon atoms, an optionally substituted straight-chained or branched alkenyl group having 2–6 carbon atoms, an optionally substituted straight-chained or branched alkynyl group having 2–6 carbon atoms, a cycloalkyl group having 3–6 carbon atoms that may be fused to a benzene ring or a heterocyclic ring, or an optionally substituted aromatic ring having 6–12 carbon atoms;

$R_{12}$ and $R_{13}$, which may be the same or different, each represent a hydrogen atom, a straight-chained or branched alkyl group having 1–4 carbon atoms or a cycloalkyl group having 3–7 carbon atoms;

$R_{14}$ is a hydrogen atom, a straight-chained or branched alkyl group having 1–6 carbon atoms, or a cycloalkyl group having 3–7 carbon atoms;

$R_{15}$ is a hydrogen atom or a methyl group;

$R_{16}$ and $R_{17}$ are taken together and represent a cycloalkyl or cycloalkenyl group having 3–7 carbon atoms.

2. The compound according to claim 1, a hydrate thereof or a pharmaceutically acceptable salt thereof, wherein A in the general formula (1) is valine (Val), leucine (Leu), isoleucine (Ile), phenylalanine (Phe), tyrosine (Tyr), tryptophan (Trp), phenylglycine (Phg), hydroxyproline (Hyp), homophenylalanine (Hph), cyclohexylglycine (Chg), cyclohexylalanine (Cha), tert-leucine (Tle), 2-thienylalanine (Thi), N-methylvaline (N-Me-Val), N-methylleucine (N-Me-Leu), N-methylisoleucine (N-Me-Ile), N-methylphenylalanine (N-Me-Phe), N-methylphenylglycine (N-Me-Phg), N-methylcyclohexylalanine (N-Me-Cha) or N-methyl-tert-leucine (N-Me-Tle).

3. The compound according to claim 1, a hydrate thereof or a pharmaceutically acceptable salt thereof, wherein $R_1$ in the general formula (1) is a phenylalanl group, a N-Me-phenylalanl group, a β-(3-indolyl)alaninoyl group, a tyrosinoyl group, a β-(2-thienyl)alaninoyl group, a β-(2-furyl)alaninoyl group, a β-cyclohexylalaninoyl group, a 3-phenylbutyryl group, a 1-benzocyclobutylcarbonyl group, a benzylaminocarbonyl group or a benzyloxycarbonyl group.

4. The compound according to claim 1, a hydrate thereof or a pharmaceutically acceptable salt thereof, wherein $R_2$ in the general formula (1) is a hydrogen atom or a methyl group.

5. The compound according to claim 1, a hydrate thereof or a pharmaceutically acceptable salt thereof, wherein $R_3$ in the general formula (1) is an amido group, an N-methylamido group, a methyl group or an aminomethyl group.

6. The compound according to claim 1, a hydrate thereof or a pharmaceutically acceptable salt thereof, wherein $R_4$ in the general formula (1) is an isopropyl group, a tert-butyl group (tBu), a 1,1-dimethylpropyl group or a 1,1-dimethyl-2-propenyl group.

7. The compound according to claims 1, a hydrate thereof or a pharmaceutically acceptable salt thereof, wherein $R_5$ in the general formula (1) is a hydroxyl group or a methoxy group.

8. The compound according to claim 1, a hydrate thereof or a pharmaceutically acceptable salt thereof, wherein A in the general formula (1) is valine (Val), leucine (Leu), isoleucine (Ile), phenylalanine (Phe), tyrosine (Tyr), tryptophan (Trp), phenylglycine (Phg), hydroxyproline (Hyp), homophenylalanine (Hph), cyclohexylglycine (Chg), cyclohexylalanine (Cha), tert-leucine (Tle), 2-thienylalanine (Thi), N-methylvaline (N-Me-Val), N-methylleucine (N-Me-Leu), N-methylisoleucine (N-Me-Ile), N-methylphenylalanine (N-Me-Phe), N-methylphenylglycine (N-Me-Phg), N-methylcyclohexylalanine (N-Me-Cha) or N-methyl-tert-leucine (N-Me-Tle); $R_1$ is a phenylalaninoyl group, a N-Me-phenylalaninoyl group, a β-(3-indolyl)alaninoyl group, a tyrosinoyl group, a β-(2-thienyl)alaninoyl group, a β-(2-furyl)alaninoyl group, a β-cyclohexylalaninoyl group, a 3-phenylbutyryl group, a 1-benzocyclobutylcarbonyl group, a benzylaminocarbonyl group or a benzyloxycarbonyl group; $R_2$ is a hydrogen atom or a methyl group; $R_3$ is an amido group, an N-methylamido group, a methyl group or an aminomethyl group; $R_4$ is an isopropyl group, a tert-butyl group (tBu), a 1,1-dimethylpropyl group or a 1,1-dimethyl-2-propenyl group; and $R_5$ is a hydroxyl group or a methoxy group.

9. The compound according to claim 1, a hydrate thereof or a pharmaceutically acceptable salt thereof which are selected from the group of compounds consisting of Phe-Phg-Tyr(3-tBu)-NH$_2$, Phe-N-Me-D-Phg-Tyr(3-tBu)-NH$_2$, Phe-Phe-Tyr(3-tBu)-NH$_2$, Phe-Cha-Tyr(3-tBu)-NH$_2$, Phe-Val-Tyr(3-tBu)-NH$_2$, Phe-Leu-Tyr(3-tBu)-NH$_2$, Phe-Tyr-Tyr(3-tBu)-NH$_2$, Phe-Hph-Tyr(3-tBu)-NH$_2$, Phe-Ile-Tyr(3-tBu)-NH$_2$, Trp-Phg-Tyr(3-tBu)-NH$_2$, Cha-Phg-Tyr(3-tBu)-NH$_2$, Phe-Val-N-Me-Tyr(3-tBu)-NH$_2$, Phe-Phg-Tyr(3-tBu)-NHMe, N-(benzylaminocarbonyl)-N-Me-D-Phe-Tyr(3-tBu)-NH$_2$, N-(S)-3-phenylbutyryl-Phg-Tyr(3-tBu)-NH$_2$, N-(2-amino-3-phenylpropyl)-Phg-Tyr(3-tBu)-NH$_2$, N-(2-amino-3-phenylpropyl)-Val-Tyr(3-tBu)-NH$_2$, N-{2-(3-tert-butyl-4-hydroxyphenyl)-1-methylethyl}-3-methyl-2-(N-methyl-N-phenylalaninoylamino)butanamide, Phe-N-Me-Val-N-Me-Tyr(3-tBu)-NH$_2$, and N-{2-(3-tert-butyl-4-hydroxyphenyl)-1-methylethyl}-3-methyl-2-{N-methyl-N-(N-Me-phenyl-alaninoyl)amino}butanamide.

10. A medicine containing the compound according to claim 1 as an active ingredient.

11. A motilin receptor antagonist composition containing the compound according to claim 1.

12. A gastrointestinal motility suppressor composition containing the compound according to claim 1 as an active ingredient.

13. A therapeutic of hypermotilinemia containing the compound according to claim 1 as an active ingredient.

14. A compound represented by formula (1), a hydrate thereof or a pharmaceutically acceptable salt thereof:

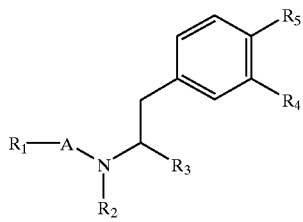

wherein A is an amino acid residue or an Nα-substituted amino acid residue other than an N-substituted glycine, provided that A binds with —NR$_2$— to form an amide;

- R$_1$ is R$_6$—CO—, an optionally substituted straight-chained or branched alkyl group having 2–7 carbon atoms, an optionally substituted straight-chained or branched alkenyl group having 3–8 carbon atoms, or an optionally substituted straight-chained or branched alkynyl group having 3–8 carbon atoms;
- R$_2$ is a hydrogen atom or an optionally substituted straight-chained or branched alkyl group having 1–3 carbon atoms;
- R$_3$ is —CO—R$_7$, an optionally substituted straight-chained or branched alkyl group having 1–5 carbon atoms, an optionally substituted straight-chained or branched alkenyl group having 2–5 carbon atoms or an optionally substituted straight-chained or branched alkynyl group having 2–5 carbon atoms;
- R$_4$ is a straight-chained or branched alkyl group having 1–6 carbon atoms, a straight-chained or branched alkenyl group having 2–6 carbon atoms, a straight-chained or branched alkynyl group having 2–6 carbon atoms, or formula (2):

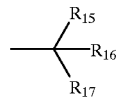

- R$_5$ is a hydrogen atom or —OR$_8$;
- R$_6$ is an optionally substituted straight-chained or branched alkyl group having 1–6 carbon atoms, an optionally substituted straight-chained or branched alkenyl group having 2–7 carbon atoms, an optionally substituted alkynyl group having 2–7 carbon atoms, a cycloalkyl group having 3–7 carbon atoms that may be fused to a benzene ring or a heterocyclic ring, an optionally substituted aromatic ring having 6–12 carbon atoms, an optionally substituted saturated or unsaturated heterocyclic ring having 3–12 carbon atoms, —N(R$_9$)R$_{10}$ or —OR$_{11}$;
- R$_7$ is a hydrogen atom, an optionally substituted straight-chained or branched alkyl group having 1–5 carbon atoms, a cycloalkyl group having 3–7 carbon atoms, —N(R$_{12}$)R$_{13}$ or —OR$_{14}$;
- R$_8$ is a hydrogen atom or a straight-chained alkyl group having 1–4 carbon atoms;
- R$_9$ and R$_{10}$, which may be the same or different, each represent a hydrogen atom, an optionally substituted straight-chained or branched alkyl group having 1–5 carbon atoms, an optionally substituted straight-chained or branched alkenyl group having 2–6 carbon atoms, an optionally substituted straight-chained or branched alkynyl group having 2–6 carbon atoms, a cycloalkyl group having 3–6 carbon atoms that may be fused to a benzene ring or a heterocyclic ring, or an optionally substituted aromatic ring having 6–12 carbon atoms;
- R$_{11}$ is an optionally substituted straight-chained or branched alkyl group having 1–5 carbon atoms, an optionally substituted straight-chained or branched alkenyl group having 2–6 carbon atoms, an optionally substituted straight-chained or branched alkynyl group having 2–6 carbon atoms, a cycloalkyl group having 3–6 carbon atoms that may be fused to a benzene ring or a heterocyclic ring, or an optionally substituted aromatic ring having 6–12 carbon atoms;
- R$_{12}$ and R$_{13}$, which may be the same or different, each represent a hydrogen atom, a straight-chained or branched alkyl group having 1–4 carbon atoms or a cycloalkyl group having 3–7 carbon atoms;
- R$_{14}$ is a hydrogen atom, a straight-chained or branched alkyl group having 1–6 carbon atoms, or a cycloalkyl group having 3–7 carbon atoms;
- R$_{15}$ is a hydrogen atom or a methyl group;
- R$_{16}$ and R$_{17}$ are taken together and represent a cycloalkyl or cycloalkenyl group having 3–7 carbon atoms.

* * * * *